United States Patent [19]

Maravetz

[11] Patent Number: 4,806,145

[45] Date of Patent: Feb. 21, 1989

[54] HERBICIDAL ARYL TRIAZOLINONES

[75] Inventor: Lester L. Maravetz, Westfield, N.J.

[73] Assignee: FMC Corporation, Philadelphia, Pa.

[21] Appl. No.: 824,696

[22] PCT Filed: Oct. 21, 1985

[86] PCT No.: PCT/US85/02065

§ 371 Date: Oct. 21, 1985

§ 102(e) Date: Oct. 21, 1985

[87] PCT Pub. No.: WO86/02642

PCT Pub. Date: May 9, 1986

Related U.S. Application Data

[63] Continuation-in-part of Ser. No. 666,933, Oct. 31, 1984, abandoned.

[51] Int. Cl.$^4$ .................. A01N 43/653; C07D 249/12

[52] U.S. Cl. .................................. 71/92; 548/263; 548/265

[58] Field of Search ..................... 548/265, 263, 264; 71/92

[56] References Cited

U.S. PATENT DOCUMENTS 4,318,731 3/1982 Kajioka et al. .................... 548/265

FOREIGN PATENT DOCUMENTS 6053662 5/1981 Japan .................................. 548/265

57-181069 11/1982 Japan .................................. 548/263

0225070 12/1983 Japan .................................. 548/265

2162511A 2/1986 United Kingdom ................ 548/263

*Primary Examiner*—Glennon H. Hollrah

*Assistant Examiner*—P. L. Morris

*Attorney, Agent, or Firm*—Robert M. Kennedy; H. Robinson Ertelt; William Schmonsees

[57] ABSTRACT

Herbicidal aryl triazolinones include the compounds of the formula

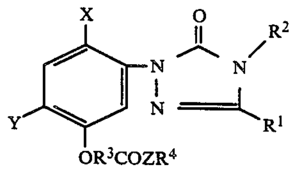

where X is preferably halogen such as fluorine, Y is preferably halogen such as chlorine, $R^1$ is preferably methyl, $R^2$ is preferably $CHF_2$, $R^3$ is preferably $CH(CH_3)$. Z is oxygen or sulfur. $R^4$ may be alkyl, substituted alkyl, alkenyl, alkynyl, monovalent cyclic having a ring of 5 or 6 atoms or $ZR^4$ may be a residue of an amine, a sulfonamide, or an oxime.

3 Claims, No Drawings

HERBICIDAL ARYL TRIAZOLINONES

This application is a continuation-in-part of Ser. No. 666,933, filed Oct. 31, 1984, now abandoned.

The invention described in this application pertains to weed control in agriculture, horticulture, and other fields where there is a desire to control unwanted plant growth. More specifically, the present application describes certain herbicidal aryl triazolinones, compositions of them, methods of preparing them, and methods for preventing or destroying undesired plant growth by preemergence or postemergence application of the herbicidal compositions to the locus where control is desired. The present compounds may be used to effectively control a variety of bothh grassy and broadleaf plant species. The present invention is particularly useful in agriculture; a number of the compounds described herein show a selectivity favorable to certain crops at application levels which inhibit the growth of or destroy a variety of weeds.

One aspect of this invention relates to herbicidal compounds of the general formula

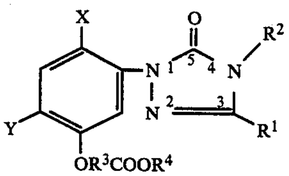

(Formula I)

wherein $R^2$ is $CHF_2$ or $CH_2F$;

X is bromine, chlorine, or fluorine or haloalkyl (e.g. $CF_3$);

$R^1$ may be halogen (e.g. chlorine), alkyl (e.g. of 1 to 5 carbon atoms), haloalkyl (e.g. of 1 to 5 carbon atoms such as difluoromethyl), alkoxyalkyl (e.g. of 2 to 6 carbon atoms such as methoxymethyl), cyanoalkyl (e.g. of 2 to 6 carbon atoms such as cyanomethyl), arylalkyl such as benzyl, alkylthio (e.g. of 1 to 3 carbon atoms such as methylthio) or the corresponding alkylsulfinyl or alkylsulfonyl, or alkylthioalkyl (e.g., of 1 to 3 carbon atoms independently with respect to each alkyl, such as methylthiomethyl) or the corresponding alkylsulfinylalkyl or alkylsulfonylalkyl.

Y is bromine, chlorine, fluorine, methyl, haloalkyl (e.g. $FCH_2$), a radical of the formula $R^8OCH_2$—, $R^8SCH_2$—, $R^8SOCH_2$— or $R^8SO_2CH_2$— where $R^8$ is $C_1$-$C_3$alkyl, $C_2$-$C_5$alkenyl, or $C_3$-$C_5$alkynyl (e.g., $CH_3OCH_2$—, $CH_3SCH_2$—, $CH_2{=}CHCH_2OCH_2$—, $CH_2{=}CHCH_2SCH_2$—, $CH{\equiv}CCH_2OCH_2$—, or $CH{\equiv}C{-}CH_2SCH_2$—); $R_8$ may also be phenyl (or phenyl substituted with e.g., halogen, alkyl, haloalkyl; see, e.g. compound 50, below).

$R^3$ is an alkylene radical (e.g. a lower alkylene such as —$CH_2$— or —$CH(CH_3)$—) or a haloalkylene radical (e.g. —CHF—) and $R^4$ is an alkyl radical (e.g. $CH_3$, $C_2H_5$, $C_3H_7$, $C_4H_9$).

It is preferred that $R^1$ be methyl and $R^2$ be $CHF_2$ and particularly that X be chlorine or (more preferably) fluorine and Y be chlorine.

Some of the compounds described above differ from otherwise similar compounds disclosed in U.S. Pat. No. 4,318,731 in that $R^2$ of that patent is hydrogen, an alkyl group, or an alkenyl group. It has been found now that the replacement of an alkyl group by a $CHF_2$ or $CH_2F$ group yields compounds of much greater herbicidal activity. This is shown, for instance, in Table I below which gives the results of tests of the following two compounds, each applied at the rate of 0.125 kg. per hectare:

A. A compound in which $R^2$ is $CHF_2$ (compound No. 5 described below).

B. An otherwise identical compound in which $R^2$ is $C_2H_5$ (compound 62 of the aforesaid U.S. patent).

Representative compounds according to this aspect of the invention are given in Table 2 below.

The herbicidal esters of the aspect of the invention described above may be hydrolyzed to produce the corresponding acids, i.e., to compounds of the foregoing formula in which the substituent para to "X" is —$OR^3COOH$ (i.e. carboxyalkoxy). I have found that these acids are also effective herbicides, somewhat less potent than the corresponding esters. The acids are also useful as intermediates for the preparation (as by esterification or amide formation) of other herbicidal compounds. The acids may be converted to their salts, such as their sodium, potassium, ammonium, calcium, magnesium, or mono, di or trialkylammonium salts, which may be used as herbicides.

Representative acids and salts are shown in Table 3 below.

In another aspect of this invention it has now been found that compounds of the following formula are effective herbicidal compounds:

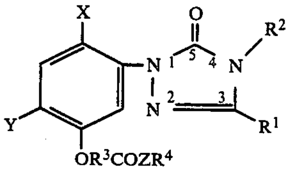

(Formula II)

wherein $R^4$ is a substituted alkyl group, an alkenyl group (e.g. allyl or methallyl) or an alkynyl group (e.g., propargyl) or a monovalent cyclic group having a ring of 5 or 6 atoms (e.g. an aromatic or heterocyclic or alicyclic ring) whose valence is on a carbon atom of said ring, and Z is O or S. Corresponding compounds in which Z is sulfur and $R^4$ is unsubstituted alkyl (e.g. of 1-4 carbon atoms) have also been found to be effective herbicides. With respect to $R^4$, examples of suitable substituents on the alkyl group are:

nitro;

halo (Cl, F, Br);

furyl or tetrahydrofuryl;

acetyl ($CH_3CO$);

—CO—$N(R^{II})(R^{III})$ where —$N(R^{II})(R^{III})$ is the residue (minus hydrogen) of ammonia or of a primary or secondary amine (e.g. methylamine, dimethylamine or other lower alkylamine);

cyano;

—$COOR^{IV}$ where $R^{IV}$ is the residue of an alcohol (such as the residue of a lower alkanol, e.g. a methyl or ethyl radical);

phenyl or substituted phenyl;

alkylamino, dialkylamino or a trialkylammonium salt (such as that shown in compound no. B20 below);

alkoxy, alkylthio, alkylsulfinyl or alkylsulfonyl (in which radicals the alkyl is preferably methyl or other lower alkyl) or phenoxy, phenylthio, phenylsulfinyl, or phenylsulfonyl (in which radicals the phenyl moiety may be substituted or unsubstituted).

When $R^4$ is alkenyl or alkynyl it may be substituted with one of the foregoing substituents.

For the substituted phenyls mentioned above the substituents may be, for instance, alkyl, haloalkyl, alkoxy, alkylthio, alkylsulfinyl, alkylsulfonyl, halogen, cyano, nitro, hydroxy, amino or alkyl or dialkylamino or carboxyl.

It is preferred that X, Y, $R^1$ and $R^2$ be as defined above for Formula I, and particularly that X be chlorine or (more preferably) fluorine, Y be chlorine, $R^1$ be methyl and $R^2$ be $CHF_2$. However, within the broader scope of this aspect of the invention $R^2$ substituents may be alkyl (e.g. of 1 to 5 carbon atoms), haloalkyl (e.g. of 1 to 5 carbon atoms, such as $CHF_2$), alkenyl of 2 to 5 carbon atoms (e.g. allyl), alkynyl of 3 to 5 carbon atoms (e.g. propargyl), cyanoalkyl (e.g. $CH_2CN$ or $CH_2CH_2CN$), thiocyanoalkyl (e.g. $CH_2SCN$) or a group of the formula -alkylene-$Y^1$-$R^5$ in which said alkylene group (e.g. $—CH_2—$) has 1 to 5 carbon atoms, $Y^1$ being oxygen or $S(O)_r$ in which r is 0 to 2, and $R^5$ being alkyl (e.g. of 1 to 5 carbon atoms such as methyl), alkenyl of 2 to 5 carbon atoms (e.g. allyl) or alkynyl of 3 to 5 carbon atoms (such as propargyl).

Representative compounds according to this aspect of the invention are shown in Table 4 below.

In still another aspect of this invention it has now been found that compounds of the following formula are effective herbicidal compounds:

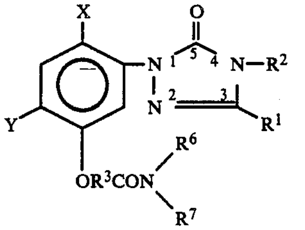

(Formula III)

in which $R^3$ is an alkylene radical (e.g. $—CH_2—$ or $—CH(CH_3)—$) or a haloalkylene radical (e.g. $—CHF—$), and

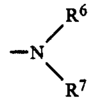

is $—NH_2$ or the residue of a primary or secondary amine or of a sulfonamide. For instance, $R^6$ and $R^7$ may be, each, independently, H, alkyl, alkenyl, alkynyl, cycloalkyl, aryl, alkoxy, alkylsulfonyl, haloalkylsulfonyl, cycloalkylsulfonyl, arylsulfonyl (including heteroarylsulfonyl such as thienylsulfonyl), aralkylsulfonyl, aminosulfonyl, dialkylaminosulfonyl, alkylaminosulfonyl, alkenylsulfonyl, phenylalkenylsulfonyl. $R^6$ may be bicyclic or polycyclic such as benzofuranyl, dihydrobenzofuranyl benzofuransulfonyl, dihydrobenzofuransulfonyl, naphthalenesulfonyl, benzodioxosulfonyl, anthraquinonesulfonyl. Any of $R^6$, $R^7$ may carry one or more substituents such as halogen, nitro, amino, alkoxy, alkyl, haloalkoxy, alkenyloxy, haloalkenyloxy, alkoxyalkoxy, alkoxyalkylthio, cyano, aminocarbonyloxy, alkylaminocarbonyloxy or dialkylaminocarbonyloxy, acylamino, alkoxycarbonyl, aminocarbonyl, alkylaminocarbonyl, dialkylaminocarbonyl or hydroxycarbonyl (but when one of $R^6$, $R^7$ is connected to the nitrogen of formula III by an oxygen or sulfur atom, then the other of $R^6$, $R^7$ is H or a group connected to that nitrogen by a carbon-nitrogen linkage or a salt-forming group, such as indicated below). $R^6$ and $R^7$ may together comprise a divalent group, such as an alkylene or haloalkylene or alkyloxyalkylene group or thioether, or its corresponding sulfine or sulfone, (e.g. such that $NR^6R^7$ together comprise a pyrrolidino, piperidino, morpholino, or thiazolidino ring), any of which may also carry a carboxylic ester or amide substituent. The salt-forming group (e.g. when $R^6$ is alkylsulfonyl, cycloalkylsulfonyl or arylsulfonyl) may be a metal (e.g. Na, K or Ca) or ammonium (e.g. $NH_4$ or lower alkyl-substituted ammonium). $R^6$ and $R^7$ may comprise a divalent group such that $NR^6R^7$ together constitute, for instance, a saccharin ring structure, e.g.

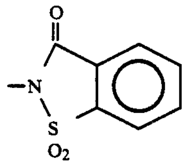

which is an active herbicide (such as compound C62 below) and which upon hydrolysis, can lead to other active herbicides such as compounds C58 and C59.

Compound C62 for example is obtainable by reaction of saccharin

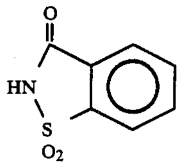

with the appropriate acid chloride.

In this (Formula III) aspect of the invention, X, Y and $R^1$ may be as defined above for Formula I, and $R^2$ may be as defined above for Formula II. It is preferred that $R^1$ be methyl and $R^2$ be $CHF_2$ and particularly that X be chlorine or (more preferably) fluorine and Y be chlorine.

Representative compounds according to this aspect of the invention are shown in Table 5 below.

Still another aspect of this invention relates to herbicidal compounds of the formula

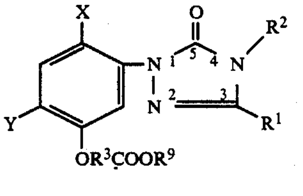

(Formula IV)

where $—OR^9$ is the residue of an oxime, such as a ketoxime of the formula

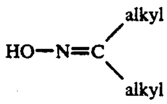 or 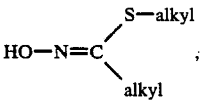 ;

each alkyl group preferably being lower alkyl such as methyl. X, Y, $R^1$ and $R^2$ have the meanings given in connection with Formula I (for X, Y and $R^1$) and Formula II (for $R^2$). Preferably X is chlorine or (more preferably) fluorine, Y is chlorine, $R^1$ is methyl and $R^2$ is $CHF_2$; in some typical compounds of this kind the radical $OR^3COOR^9$ is

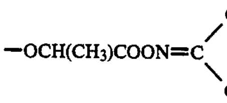

or

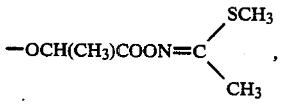

,

X is fluorine, Y is chlorine, $R^1$ is methyl and $R^2$ is $CHF_2$; other typical compounds are identical with those except that Y is Br or $CF_3$. Compounds of Formula IV may be prepared by reacting the corresponding acid chloride (i.e. the compound in which the substituent at the 5-position of the benzene ring is $-OR^3COCl$) with the corresponding oxime in the presence of an acceptor for HCl such as triethylamine or sodium carbonate or sodium hydroxide.

In each aspect of the invention, it is often preferable that any alkyl, alkenyl, alkynyl or alkylene radical have less than 6 carbon atoms.

The compounds of this invention may be prepared by methods generally described in the literature or by methods analogous or similar thereto and within the skill of the art. One type of method starts with an intermediate in which the substituent para to "X" is hydroxyl. For instance, one may use the intermediate described in "Synthetic Process Example 6" of UK patent application No. GB 2 090 250 published July 7, 1982, in which X and Y are Cl, $R^1$ is $CH_3$ and $R^2$ is $CHF_2$ (the corresponding compound in which $R^2$ is $CH_2F$ is made by substituting chlorofluoromethane for the chlorodifluoromethane used in "Synthetic Process Example 1" of that published patent application). The OH group of the intermediate may then be converted to the desired substituent, as by a conventional etherification reaction, e.g., by reacting it with the appropriate bromide in the presence of a known acceptor of HBr such as NaH or a mixture of $K_2CO_3$ and NaI.

As illustrated in Examples 2 and 3 below, the synthesis may employ a substituted phenylhydrazine, whose hydrazine portion is then modified to form a triazolinone ring. Such modification (which in Examples 2 and 3 is effected by reaction with pyruvic acid and then with a phosphoryl azide) may also be effected by other techniques, such as by treating the substituted phenylhydrazine with any of the following four types of reagents:

(a) an inner salt of a 3-(1-iminoalkylmercapto)-1-propanesulfonic acid (which may be prepared according to Reid and Schmidt, Ann. Chem. 676, 114 (1964) from 1,3-propanesultone and a thioamide), to form an amidrazone followed by reaction with a source of phosgene, as by the following reaction sequence (which is also illustrated in Example 15 below),

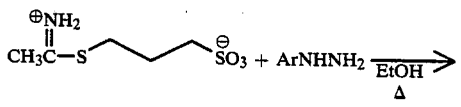

-continued

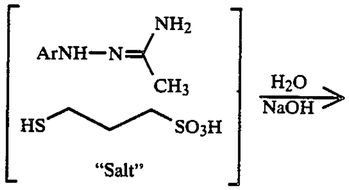

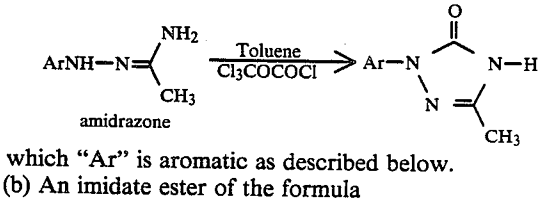

amidrazone in which "Ar" is aromatic as described below.

(b) An imidate ester of the formula

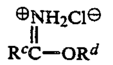

to form the corresponding amidrazone (as described, for instance, in the article by Neilson et al "The Chemistry of Amidrazones: Chem. Rev. 70, 151(1970) at page 156), followed by reaction with a source of phosgene, as in (a) above, $R^c$ and $R^d$ being alkyl or other suitable radical.

(c) A compound of the formula

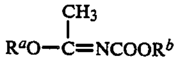

or

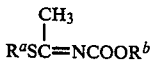

(where $R^a$ and $R^b$ are lower alkyl) in the presence of a base according to the following sequence:

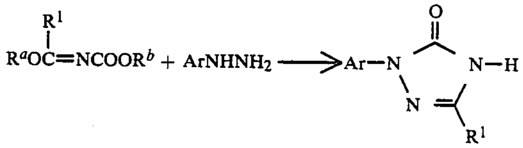

in which $R^1$ is as defined above, e.g. methyl;

(d) A haloalkylnitrile (e.g. a fluoroalkyl, fluorochloroalkyl or fluorobromoalkyl nitrile such as $ClCF_2CN$, followed by reaction with a source of phosgene, so that the reaction may proceed along the following lines, for instance (and as also illustrated in Example 16 below), to form the aryl 3-haloalkyl triazoline, thus:

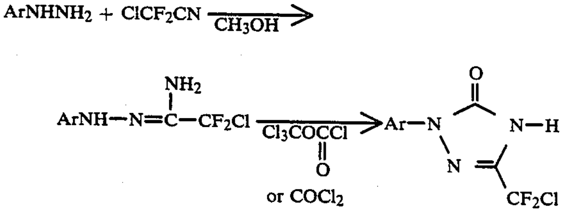

In Examples 2 and 3 below the "Ar" portion of the aryl hydrazine (whose hydrazine portion is then modified to form the triazoline ring) has halo substituents at its 2 and 4 positions and an alkoxy group at its 5 position. Instead, in each of the processes illustrated above (and in the process of those Examples 2 and 3), the Ar group may be a phenyl radical or a fluorophenyl (e.g. 2-fluorophenyl) or a nitrophenyl (e.g. 3-nitrophenyl)alkoxyphenyl (e.g. 3-methoxyphenyl) or, most preferably, halonitrophenyl, particularly a fluoronitrophenyl (such as 2-fluoro-5-nitrophenyl) or haloalkoxyphenyl (such as 2-fluoro-5-alkoxyphenyl) and the aryl triazoline may then be treated to (a) alkylate the nitrogen at the 4-position of the triazoline ring (in known manner, e.g. with an alkyl or fluoroalkyl halide, such as with $ClCHF_2$ to add the preferred—$CHF_2$ substituent) and (b) to introduce additional substituents onto the aromatic ring, as by halogenation with chlorine or bromine (e.g. by reacting with $Cl_2$, $Br_2$ or $SO_2Cl_2$). For instance the alkylation of the nitrogen at the 4-position may be effected first, after which the nitro group (if present) may be reduced to an amino group in conventional manner, the amino group may be converted to a hydroxyl group (as by conventional diazotization) and then, preferably after etherifying the OH to form an alkoxy (e.g. methoxy) group, the compound may be halogenated as above to place the halogen substituent or substituents on its benzene ring. The resulting compound may then be modified at the 5-position of the benzene ring to form the herbicidal compounds of this invention. For instance, for making the preferred compounds of the invention in which the benzene ring has a 2-fluoro substituent, the starting material may be 2-fluoro-5-nitrophenylhydrazine, which may be treated as described above to produce successively a series of novel compounds such as 1-(2-fluoro-5-nitrophenyl)-4,5-dihydro-3-methyl-1,2,4-triazol-5(1H)-one, then 1-(2-fluoro-5-nitrophenyl-4,5-dihydro-4-difluoromethyl-3-methyl-1,2,4-triazol-5(1H)-one. These may be converted to the corresponding novel compounds having, at the 5-position of the benzene ring, successively —$NH_2$, —OH and (preferably) —$OCH_3$, followed by halogenation to place, for instance, a chloro or bromo substituent at the 4-position of the benzene ring. Instead of alkylating at the 4-position of the ring triazoline at an early stage, e.g. prior to altering the nitro group, this alkylation step may be delayed until after the abovedescribed halogenation of the benzene ring or even until after the conversion of the alkoxy (or other) group at the 5-position of the benzene ring to one of the groups described at that position in Formulas I, II, III and IV (and Tables 2, 3, 4, and 5) above.

Similarly, when the reagent(s) used to react with the aryl hydrazine are such as to produce a triazolinone having a haloalkyl (e.g. $CHF_2$) group instead of an alkyl group on the carbon at the 3-position of the heterocyclic ring, the series of new compounds will include, successively, (from 2-fluoro-5-nitrophenyl hydrazine) such compounds as 1-(2-fluoro-5-nitrophenyl)-4,5-dihydro-3-difluoromethyl-1,2,4-triazol-5-(1H)-one, then 1-(2-fluoro-5-nitrophenyl)-4,5-dihydro-4-methyl (or difluoromethyl)-3-difluoromethyl-1,2,4-triazol-5(1H)-one. These may be converted to the corresponding novel compounds having, at the 5-position of the benzene ring, successively —$NH_2$, —OH and (preferably) —$OCH_3$ followed by halogenation to place, for instance, a chloro or bromo substituent at the 4-position of the benzene ring. When the aryl hydrazine is 3-nitrophenyl hydrazine (instead of 2-fluoro-5-nitrophenylhydrazine) the series of novel compounds will include, successively, such compounds as 1-(3-nitrophenyl)-4,5-dihydro-3-difluoromethyl-1,2,4-triazol-5(1H)-one, then 1-(3-nitrophenyl)-4,5-dihydro-4-methyl (or difluoromethyl)-3-difluoromethyl-1,2,4-triazol-5(1H)-one. These may be converted to the corresponding novel compounds having, at the 3-position of the benzene ring, successively —$NH_2$, —OH and (preferably) —$OCH_3$, followed by halogenation to place, for instance, chloro or bromo substituents on the benzene ring.

Example 11 below illustrates a process for making a compound of this invention having a sulfonamide group at the 5-position of the benzene ring by reacting (a) a compound having an oxypropionic acid substituent at that 5-position with (b) an aryl sulfonylisocyanate.

Another method for introducing the sulfonamide group is by reacting (a) a compound having a phenolic OH group at that 5-position with (b) an N-aryl (or alkyl etc.) sulfonylalkanoic acid amide having a reactive leaving substituent (e.g. Br, Cl, mesylate or tosylate) on the alkane portion of the molecule, e.g.

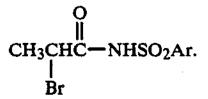

Such a reaction can be carried out in the presence of a base (e.g. in acetone in the presence of sodium or potassium carbonate). This method is illustrated in Example 14 below.

The following Examples illustrate the preparation of the compounds of this invention.

EXAMPLE 1

Ethyl [2,4-dichloro-5-(4-difluoromethyl-4,5-dihydro-3-methyl-5-oxo-1H-1,2,4-triazol-1-yl)phenoxy]acetate To a stirred mixture of 15.0 g (0.048 mole) of 1-(2,4-dichloro-5-hydroxyphenyl)-4-difluoromethyl-4,5-dihydro-3-methyl-1,2,4-triazol-5(1H)-one and 3.4 g (0.024 mole) of potassium carbonate in 100 mL of acetone was added 8.1 g (0.048 mole) of ethyl bromoacetate. The resultant mixture was stirred at reflux for three hours. After cooling, the mixture was evaporated under reduced pressure leaving a residue. This residue was partitioned between diethyl ether and water. The organic phase was washed with an aqueous 10% sodium hydroxide solution, then was dried over anhydrous magnesium sulfate and filtered. Evaporation of the filtrate under reduced pressure produced 17.8 g of a solid. A small portion of this solid was recrystallized from methanol and water to yield ethyl [2,4-dichloro-5-(4-difluoromethyl-4,5-dihydro-3-methyl-5-oxo-1H-1,2,4-triazol-1-yl)phenoxy]acetate (mp 118°-119° C.), compound 17.

The nmr spectrum was consistent with the proposed structure.

The following compounds were also prepared by the process of Example 1 from 1-(2,4-dichloro-5-hydroxyphenyl)-4-difluoromethyl-4,5-dihydro-3-methyl-1,2,4-triazol-b 5(1H)-one; 1-(4-chloro-2-fluoro-5-hydroxyphenyl)-4-difluoromethyl-4,5-dihydro-3-methyl-1,2,4-triazol-5(1H)-one; 2-[2,4-dichloro-5-(4-difluoromethyl-4,5-dihydro-3-methyl-5-oxo-1H-1,2,4-triazol-1-yl)phenoxy]propionic acid, compound A1; or 2-[4-chloro-2-fluoro-5-(4-difluoromethyl-4,5-dihydro-3-methyl-5-oxo-1H-1,2,4-triazol-1-yl)phenoxy]propionic acid, compound A2, and one of the following:

| Compound | Reagent |
|---|---|
| 14 | methyl bromoacetate |
| 17 | ethyl bromoacetate |
| 19 | tert-butyl 2-bromopropionate |
| 21 | tert-butyl bromoacetate |
| 22 | tert-butyl bromoacetate |
| B6 | 1-methyl-2-propynyl 2-bromopropionate |
| B7 | 1,1-dimethyl-2-propynyl 2-chloropropionate |
| B11 | bromoacetonitrile |
| B16 | α-bromo-γ-butyrolactone |
| B22 | chloromethyl methylether |
| B23 | chloromethyl methylsulfide |
| C1 | iodoacetamide |
| C7 | iodoacetamide |
| C9 | N—(1-methylpropyl) 2-bromopropionamide |

EXAMPLE 2

2-[2-Chloro-4-fluoro-5-(4-difluoromethyl-4,5-dihydro-3-methyl-5-oxo-1H-1,2,4-triazol-1-yl)phenoxy]propionic acid Step A 4-Chloro-2-fluoro-5-methoxyaniline from 2-chloro-4-fluorophenol The intermediate 4-chloro-2-fluoro-5-methoxyaniline was prepared in a five step synthesis from commercially available 2-chloro-4-fluorophenol as detailed by E. Nagano, et al. in European Patent Application No. 69,855.

Step B 4-Chloro-2-fluoro-5-methoxyphenylhydrazine

A stirred solution of 48.0 g (0.27 mole) of 4-chloro-2-fluoro-5-methoxyaniline in 500 mL of concentrated hydrochloric acid was cooled to −5° C. and 23.5 g (0.34 mole) of sodium nitrite in 100 mL of water was added dropwise. After complete addition the reaction mixture was stirred at 0° C. for one hour. A second solution of 154.0 g (0.68 mole) of stannous chloride in 225 mL of concentrated hydrochloric acid was cooled to 0° C., and the cold diazonium solution prepared above was added to it slowly. After complete addition the reaction mixture was allowed to warm to ambient temperature. The reaction mixture was filtered to collect a solid. This solid was dissolved in an aqueous 50% sodium hydroxide solution and the solution extracted with toluene. The toluene extract was dried with magnesium sulfate and filtered. The filtrate was concentrated under reduced pressure to yield 22.4 g of 4-chloro-2-fluoro-5-methoxyphenylhydrazine as a solid.

The nmr spectrum was consistent with the proposed structure.

Step C Pyruvic acid, 4-chloro-2-fluoro-5-methoxyphenylhydrazone

A stirred solution of 21.0 g (0.11 mole) of 4-chloro-2-fluoro-5-methoxyphenylhydrazine and 100 mL of aqueous 10% hydrochloric acid in 100 mL of ethanol was warmed to 40° C., and a solution of 10.0 g (0.114 mole) of pyruvic acid in 20 mL of water was added. Upon complete addition the reaction mixture was stirred for one hour. An additional 50 mL of water was added and the reaction mixture filtered to collect a solid. The solid was air dried to yield 29.0 g of pyruvic acid, 4-chloro-2-fluoro-5-methoxyphenylhydrazone; mp 166°-169° C.

The nmr spectrum was consistent with the proposed structure.

Step D 1-(4-Chloro-2-fluoro-5-methoxyphenyl)-4,5-dihydro-3-methyl-1,2,4-triazol-5(1H)-one A stirred solution of 27.0 g (0.104 mole) of pyruvic acid, 4-chloro-2-fluoro-5-methoxyphenylhydrazone, 29.0 g (0.105 mole) of diphenyl phosphoryl azide, and 11.0 g (0.108 mole) of triethylamine in 500 mL of toluene was heated under reflux for four hours. The reaction mixture was cooled to ambient temperature and extracted with an aqueous 10% sodium hydroxide solution. The extract was neutralized with gaseous carbon dioxide, and a solid was collected by filtration. The solid was air dried to yield 11.0 g of 1-(4-chloro-2-fluoro-5-methoxyphenyl)-4,5-dihydro-3-methyl-1,2,4-triazol-5(1H)-one; mp 193°-195° C.

The nmr spectrum was consistent with the proposed structure.

Step E 1-(4-Chloro-2-fluoro-5-methoxyphenyl)-4,5-dihydro-4-difluoromethyl-3-methyl-1,2,4-triazol-5(1H)-one A stirred mixture of 10.0 g (0.039 mole) of 1-(4-chloro-2-fluoro-5-methoxyphenyl)-4,5-dihydro-3-methyl-1,2,4-triazol-5(1H)-one, 10.0 g (0.031 mole) of tetrabutylammonium bromide and 10.0 grams (0.25 mole) of sodium hydroxide in 250 mL of cyclohexane was warmed to 60° C. Chlorodifluoromethane (10.0 g, 0.12 mole) was bubbled into the reaction mixture. After complete addition the reaction mixture was warmed to reflux where it stirred for one hour. The hot solution was decanted from a pot residue and cooled to ambient temperature. Methylene chloride was added to the cooled mixture to dissolve a solid precipitate. The mixture was washed with 10% hydrochloric acid then with an aqueous 10% sodium hydroxide solution. The organic layer was dried with anhydrous magnesium sulfate and filtered. The filtrate was concentrated under reduced pressure to yield 5.0 g of 1-(4-chloro-2-fluoro-5-methoxyphenyl)-4-difluoromethyl-4,5-dihydro-3-methyl-1,2,4-triazol-5(1H)-one; mp 86°-88° C.

The nmr spectrum was consistent with the proposed structure.

Step F 1-(4-Chloro-2-fluoro-5-hydroxyphenyl)-4-difluoromethyl-4,5-dihydro-3-methyl-1,2,4-triazol-5(1H)-one A stirred mixture of 4.6 g (0.015 mole) of 1-(4-chloro-2-fluoro-5-methoxyphenyl)-4-difluoromethyl-4,5-dihydro-3-methyl-1,2,4-triazol-5(1H)-one in 200 mL of methylene chloride was cooled to 10° C. and a solution of 11.2 g (0.045) mole of boron tribromide in 45 mL of methylene chloride was added. Upon complete addition the reaction mixture was stirred for four hours as it warmed to ambient temperature. After this time 100 mL of water was added, and stirring was continued for an additional 18 hours. The organic layer was separated, dried with anhydrous magnesium sulfate, and filtered. The filtrate was concentrated under reduced pressure to yield 4.4 g of 1-(4-chloro-2-fluoro-5-hydroxyphenyl)-4-difluoromethyl-4,5-dihydro-3-methyl-1,2,4-triazol-5(1H)-one; mp 147°-152° C.

The nmr spectrum was consistent with the proposed structure.

Step G Methyl 2-[2-chloro-4-fluoro-5-(4-difluoromethyl-4,5-dihydro-3-methyl-5-oxo-1H-1,2,4-triazol-1-yl)phenoxy]propionate To a stirred mixture of 1.5 g (0.0051 mole) of 1-(4-chloro-2-fluoro-5-hydroxyphenyl)-4-difluoromethyl-4,5-dihydro-3-methyl-1,2,4-triazol-5(1H)-one and 0.12 g (0.0051 mole) of sodium hydride in 50 mL of N,N-dimethylformamide was added 0.85 g (0.0051 mole) of methyl 2-bromopropionate. After complete addition the reaction mixture was heated at reflux for two hours, then cooled to room temperature and stirred for approximately 18 hours. The solvent was removed by evaporation under reduced pressure leaving a residue. This residue was partitioned between diethyl ether and water. The organic phase was washed with an aqueous 10% sodium hydroxide solution. The organic phase was dried over anhydrous magnesium sulfate and filtered. The filtrate was evaporated under reduced pressure to yield 1.5 g of methyl 2-[2-chloro-4-fluoro-5-(4-difluoromethyl-4,5-dihydro-3-methyl-5-oxo-1H-1,2,4-triazol-1-yl)phenoxy]propionate as an oil, Compound 3.

The nmr spectrum was consistent with the proposed structure.

The following compounds were also prepared by the process of Example 2, Step G, from 1-(2,4-dichloro-5-hydroxyphenyl)-4-difluoromethyl-4,5-dihydro-3-methyl-1,2,4-triazol-5(1H)-one; 1-(4-chloro-2-fluoro-5-hydroxyphenyl)-4-difluoromethyl-4,5-dihydro-3-methyl-1,2,4-triazol-5(1H)-one; or compound A2 and one of the following reagents:

| Compound | Reagent |
|---|---|
| 1 | methyl bromoacetate |
| 2 | methyl 2-bromopropionate |
| 5 | ethyl 2-bromopropionate |
| 6 | ethyl 2-bromopropionate |
| 18 | ethyl 4-bromopropionate |
| 20 | ethyl 2-bromoisobutyrate |
| B21 | N,N—diethyl-2-chloroacetamide |
| C8 | N,N—diethyl-2-chloroacetamide |

Step H 2-[2-Chloro-4-fluoro-5-(4-difluoromethyl-4,5-dihydro-3-methyl-5-oxo-1H-1,2,4-triazol-1-yl)phenoxy]propionic acid A stirred mixture of 1.3 g (0.0034 mole) of methyl 2-[2-chloro-4-fluoro-5-(4-difluoromethyl-4,5-dihydro-3-methyl-5-oxo-1H-1,2,4-triazol-1-yl)phenoxy]propionate and 1.0 g (0.018 mole) of potassium hydroxide in 15 mL of ethanol and 15 mL of water was heated at reflux for three hours. The mixture was allowed to cool to room temperature and stand for two days. The solvent was evaporated from the mixture leaving a solid. This solid was dissolved in water, and the solution was made acidic with concentrated hydrochloric acid. This solution was extracted with methylene chloride. The extract was dried over anhydrous magnesium sulfate and filtered. Evaporation of the solvent from the filtrate left 0.85 g of 2-[2-chloro-4-fluoro-5-(4-difluoromethyl-4,5-dihydro-3-methyl-5-oxo-1H-1,2,4-triazol-1-yl)phenoxy]propionic acid as a solid (mp 50°-55° C.), Compound A2.

Compound A1 was also prepared by the method of Example 2, Step H, from Compound 2.

EXAMPLE 3

2-[4-Chloro-5-(4-difluoromethyl-4,5-dihydro-3-methyl-5-oxo-1H-1,2,4-triazol-1-yl)-2-methylphenoxy]propionic acid Step A 4-Methyl-3-methoxyphenylhydrazine A stirred mixture of 100.0 g (0.73 mole) of 4-methyl-3-methoxyaniline in 800 mL of concentrated hydrochloric acid was cooled to −5° C. A solution of 501.5 g (0.73 mole) of sodium nitrite in 250 mL of water was added slowly while maintaining the temperature of the reaction mixture below 0° C. The resultant mixture was stirred at −5° C. for 30 minutes. A cold solution of 330.0 g (1.46 mole) of tin (II) chloride dihydrate in 360 mL of concentrated hydrochloric acid was added over one hour. After complete addition the resultant mixture was allowed to warm to room temperature. A solid precipitate formed and was collected by filtration and stirred in 200 mL of water. This mixture was neutralized with 50% aqueous sodium hydroxide, and extracted with toluene. The extract was dried over anhydrous magnesium sulfate and filtered. The filtrate was evaporated under reduced pressure to yield 58.0 g of 4-methyl-3-methoxyphenylhydrazine as an oil.

The nmr spectrum was consistent with the proposed structure.

Step B Pyruvic acid, 4-methyl-3-methoxyphenylhydrazone

To a stirred mixture of 57.6 g (0.378 mole) of 4-methyl-3-methoxyphenylhydrazine in 400 mL of ethanol and 400 mL of 1N hydrochloric acid was added 33.3 g (0.0378 mole) of pyruvic acid. After complete addition the mixture was stirred at room temperature for one hour, and 1 liter of water was added. The mixture was extracted with methylene chloride. The extract was dried over anhydrous magnesium sulfate and filtered. The filtrate was evaporated under reduced pressure to yield 59.0 g of pyruvic acid, 4-methyl-3-methoxyphenylhydrazone.

The nmr spectrum was consistent with the proposed structure.

Step C 4,5-Dihydro-1-(4-methyl-3-methoxyphenyl)-3-methyl-1,2,4-triazol-5(1H)-one To a stirred mixture of 56.8 g (0.26 mole) of pyruvic acid, 4-methyl-3-methoxyphenylhydrazone in 1500 mL of toluene was added 25.9 g (0.26 mole) of triethylamine. The mixture was heated at 50° C., and 70.3 g (0.26 mole) of diphenyl phosphoryl azide was added. The resultant mixture was heated at reflux for approximately 18 hours. The mixture was cooled and extracted with four 200 mL portions of an aqueous 10% sodium hydroxide solution. The aqueous extracts were combined, washed with toluene, and made acidic. The resultant solid was collected by filtration and air dried to yield 75.0 g of 4,5-dihydro-1-(4-methyl-3-methoxyphenyl)-3-methyl-1,2,4-triazol-5(1H)-one (mp 164°-168° C.).

The nmr spectrum was consistent with the proposed structure.

Step D 4-Difluoromethyl-4,5-dihydro-1-(4-methyl-3-methoxyphenyl)-3-methyl-1,2,4-triazol-5(1H)-one A stirred mixture of 60.0 g (0.28 mole) of 4,5-dihydro-1-(4-methyl-3-methoxyphenyl)-3-methyl-1,2,4-triazol-5(1H)-one, 60.0 g (0.19 mole) of tetrabutylammonium bromide and 60.0 g (1.5 mole) of powdered sodium hydroxide in 2 liters of cyclohexane was heated at reflux. During a two hour period 60.0 g (0.67 mole) of gaseous difluorochloromethane was bubbled into the mixture. After complete addition the mixture was stirred at reflux for one hour, then allowed to cool to 70° C. The supernatant liquid was decanted and washed with aqueous 10% hydrochloric acid followed by an aqueous 10% sodium hydroxide solution. The organic layer was dried with magnesium sulfate and filtered. The filtrate was evaporated under reduced pressure to leave a solid. This solid was triturated with petroleum ether and filtered. The filter cake was air dried to yield 18.5 g of 4-difluoromethyl-4,5-dihydro-1-(4-methyl-3-methoxyphenyl)-3-methyl-1,2,4-triazol-5-(1H)-one.

The nmr spectrum was consistent with the proposed structure.

Step E 1-(2-Chloro-4-methyl-5-methoxyphenyl)-4-difluoromethyl-4,5-dihydro-3-methyl-1,2,4-triazol-5(1H)-one A solution of 15.0 g (0.056 mole) of 4-difluoromethyl-4,5-dihydro-1-(4-methyl-3-methoxyphenyl)-3-methyl-1,2,4-triazol-5(1H)-one and 7.5 g (0.056 mole) of sulfuryl chloride in 100 mL of chloroform was stirred at room temperature for two hours. The reaction mixture was concentrated under reduced pressure to leave a residue. This residue was dissolved in methylene chloride and washed with an aqueous 10% sodium hydroxide solution. The organic layer was dried with magnesium sulfate and filtered. The filtrate was concentrated under reduced pressure to yield 16.5 g of 1-(2-chloro-4-methyl-5-methoxyphenyl)-4-difluoromethyl-4,5-dihydro-3-methyl-1,2,4-triazol-5(1H)-one as a solid.

The nmr spectrum was consistent with the proposed structure.

Step F 1-(2-Chloro-4-methyl-5-hydroxyphenyl)-4-difluoromethyl-4,5-dihydro-3-methyl-1,2,4-triazol-5(1H)-one To a stirred solution of 16.0 g (0.053 mole) of 1-(2-chloro-4-methyl-5-methoxyphenyl)-4-difluoromethyl-4,5-dihydro-3-methyl-1,2,4-triazol-5(1H)-one in 100 mL of methylene chloride at 10° C. was added dropwise 39.6 g (0.16 mole) of boron tribromide. The resultant mixture was stirred at room temperature for two days. This mixture was washed with 100 mL of water. The organic layer was dried with anhydrous magnesium sulfate and filtered. The filtrate was concentrated under reduced pressure to leave an oil. This oil was stirred in petroleum ether:diethyl ether (90:10) forming a solid. The solid was collected by filtration to yield 10.5 g of 1-(2-chloro-4-methyl-5-hydroxyphenyl)-4-difluoromethyl-4,5-dihydro-3-methyl-1,2,4-triazol-5(1H)-one (mp 154°-156° C.).

The nmr spectrum was consistent with the proposed structure.

Step G Methyl 2-[4-chloro-5-(4-difluoromethyl-4,5-dihydro-3-methyl-5-oxo-1H-1,2,4-triazol-1-yl)-2-methylphenoxy]propionate In a manner similar to Example 2, Step G, the reaction of 3.0 g (0.01 mole) of 1-(2-chloro-4-methyl-5-hydroxyphenyl)-4-difluoromethyl-4,5-dihydro-3-methyl-1,2,4-triazol-5(1H)-one, 0.25 g (0.01 mole) of sodium hydride and 1.75 g (0.01 mole) of methyl 2-bromopropionate in 100 mL of N,N-dimethylformamide produced 3.7 g of methyl 2-[4-chloro-5-(4-difluoromethyl-4,5-dihydro-3-methyl-5-oxo-1H-1,2,4-triazol-1-yl)-2-methylphenoxy]propionate as an oil, Compound 4.

The nmr spectrum was consistent with the proposed structure.

Compound 7 was prepared by the process described for Compound 4, but using ethyl 2-bromopropionate in Step G.

Step H 2-[4-Chloro-5-(4-difluoromethyl-4,5-dihydro-3-methyl-5-oxo-1H-1,2,4-triazol-1-yl)-2-methylphenoxy]-propionic acid In a manner similar to Example 2, Step H, the reaction of 3.3 g (0.0088 mole) of methyl 2-[4-chloro-5-(4-difluoromethyl-4,5-dihydro-3-methyl-5-oxo-1H-1,2,4-triazol-1-yl)-2-methylphenoxy]propionate with 1.5 g (0.27 mole) of potassium hydroxide in 50 mL of ethanol and 15 mL of water produced 2.7 g of 2-[4-chloro-5-(4-difluoromethyl-4,5-dihydro-3-methyl-5-oxo-1H-1,2,4-triazol-1-yl)-2-methylphenoxy]propionic acid as a solid (mp 56°-60° C.), Compound A3.

The nmr spectrum was consistent with the proposed structure.

EXAMPLE 4

2-Nitropropyl 2-[2,4-dichloro-5-(4-difluoromethyl-4,5-dihydro-3-methyl-5-oxo-1H-1,2,4-triazol-1-yl)phenoxy]propionate A stirred mixture of 0.5 g (0.0013 mole) of 2-[2,4-dichloro-5-(4-difluoromethyl-4,5-dihydro-3-methyl-5-oxo-1H-1,2,4-triazol-1-yl)phenoxy]propionic acid (Compound A1), 1.0 g (0.0095 mole) of 2-nitro-1-propanol and 0.05 g (0.0003 mole) of p-toluenesulfonic acid monohydrate in 60 mL of toluene was heated at reflux. The water generated in the reaction was removed by collection in a Dean-Stark trap. After refluxing for a total of two hours, the solvent was removed by distillation under reduced pressure leaving a residue. This residue was dissolved in diethyl ether and washed first with water then with an aqueous 10% sodium hydroxide solution. The organic phase was dried over anhydrous magnesium sulfate and filtered. The filtrate was evaporated to yield 0.5 g of 2-nitropropyl 2-[2,4-dichloro-5-(4-difluoromethyl-4,5-dihydro-3-methyl-5-oxo-1H-1,2,4-triazol-1-yl)phenoxy]propionate as an oil, Compound B1.

The nmr spectrum was consistent with the proposed structure.

Compound 11 was also prepared by the method of Example 4 from Compound A1 and n-butanol.

EXAMPLE 5

2-Propenyl 2-[2,4-dichloro-5-(4-difluoromethyl-4,5-dihydro-3-methyl-5-oxo-1H-1,2,4-triazol-1-yl)phenoxy]propionate Under a dry nitrogen atmosphere, a stirred solution of 0.5 g (0.0013 mole) of methyl 2-[2,4-dichloro-5-(4-difluoromethyl-4,5-dihydro-3-methyl-5-oxo-1H-1,2,4-triazol-1-yl)phenoxy]propionate (Compound 2) and approximately 0.01 g of sodium methoxide in 30 mL of 2-propen-1-ol was heated at reflux. After approximately 5 mL of methanol was collected in a Dean-Stark trap, the reaction mixture was cooled slightly, and the remaining solvent removed by distillation under reduced pressure leaving a residue. This residue was dissolved in diethyl ether and washed with water. The organic phase was dried over anhydrous magnesium sulfate and filtered. The filtrate was evaporated under reduced pressure to yield 0.55 g of 2-propenyl 2-[2,4-dichloro-5-(4-difluoromethyl-4,5-dihydro-3-methyl-5-oxo-1H-1,2,4-triazol-1-yl)phenoxy]propionate as an oil, Compound B2.

The nmr spectrum was consistent with the proposed structure.

Analysis Calc'd for $C_{16}H_{15}N_3Cl_2F_2O_4$: C 45.52;H 3.58;N 9.95. Found: C 45.24;H 3.76;N 9.87.

The following compounds were also prepared by the process of Example 5 from 1-(2,4-dichloro-5-hydroxyphenyl)-4-difluromethyl-4,5-dihydro-3-methyl-1,2,4-triazol-5(1H)-one; compound A1; or compound A2 and the following reagents:

| Compound | Reagent |
|---|---|
| 9 | n-propanol |
| 10 | 2-propanol |
| 15 | n-propanol |
| 16 | 2-propanol |
| B3 | 2-propyn-1-ol |

-continued

| Compound | Reagent |
|---|---|
| B5 | 2-methoxyethanol |

EXAMPLE 6

N-methylsulfonyl-2-[2,4-Dichloro-5-(4-difluoromethyl-4,5-dihydro-3-methyl-5-oxo-1H-1,2,4-triazol-1-yl)phenoxy]propionamide Step A 2-[2,4-Dichloro-5-(4-difluromethyl-4,5-dihydro-3-methyl-5-oxo-1H-1,2,4-triazol-1-yl)phenoxy]-propionyl chloride A stirred mixture of 2.9 g (0.0075 mole) of 2-[2,4-dichloro-5-(4-difluoromethyl-4,5-dihydro-3-methyl-5-oxo-1H-1,2,4-triazol-1-yl)phenoxy]propionic acid (Compound A-1) in 5 mL of thionyl chloride was heated at reflux for 1.5 hours. The mixture was cooled, and the excess thionyl chloride was removed by evaporation under reduced pressure, leaving 3.1 g of product as an oil.

Step B N-Methylsulfonyl-2-[2,4-dichloro-5-(4-difluoromethyl-4,5-dihydro-3-methyl-5-oxo-1H-1,2,4-triazol-1-yl)phenoxy]propionamide A mixture of 0.56 g of the oil from Step A and 0.56 g (0.0059 mole) of methanesulfonamide was heated at 80° C. for 3.5 hours. The mixture was cooled and diluted with water, forming a gummy precipitate. The water was decanted, and the residue was partitioned between water and methylene chloride. The organic phase was washed with three 100 ml portions of water, dried over anhydrous magnesium sulfate, and filtered. The filtrate was evaporated under reduced pressure to leave a tan solid which was dissolved in 30 mL of 1N sodium hydroxide and 50 mL of water. The basic mixture was filtered, and the filtrate was made acidic with concentrated hydrochloric acid. A precipitate formed and was collected by filtration. The filter cake was washed with water and dried to yield 0.34 g of N-methylsulfonyl-2-[2,4-dichloro-5-(4-difluoromethyl-4,5-dihydro-3-methyl-5-oxo-1H-1,2,4-triazol-1-yl)phenoxy]propionamide (mp 185°-188° C.), Compound C3.

The nmr spectrum was consistent with the proposed structure.

Analysis Calc'd for $C_{14}H_{14}Cl_2F_2N_4O_5S$: C 36.61; H 3.07; N 12.20. Found: C 36.79; H 3.01; N 12.41.

Compounds C4, C5 and C6 were prepared by the process described in Example 6 using trifluoromethanesulfonamide, ammonia and methylamine respectively in Step B. Compounds C2 and C18 were prepared by the method of Example 6 from Compound A2, using methylamine and methanesulfonamide respectively in Step B.

EXAMPLE 7

Ethyl 2-[2,4-dibromo-5-(4-difluoromethyl-4,5-dihydro-3-methyl-5-oxo-1H-1,2,4-triazol-1-yl)phenoxy]propionate Step A 1-(2,4-Dibromo-5-methoxyphenyl)-4-difluoromethyl-4,5-dihydro-3-methyl-1,2,4-triazol-5(1H)-one To a stirred mixture of 12.0 g (0.047 mole) of 1-(3-methoxyphenyl)-4-difluoromethyl-4,5-dihydro-3-methyl-1,2,4-triazol-5(1H)-one (prepared from 3-methoxyaniline using the method of Example 2, Steps B-E) in 75 mL of acetic acid was added 30.0 g (0.19 mole) of bromine. The mixture was heated at reflux for six hours, then cooled. The solvent was removed by distillation, leaving a residue. This residue was dissolved in diethyl ether, and the resultant solution was washed first with an aqueous 10% sodium thiosulfate solution followed by water. The organic solution was dried over anhydrous magnesium sulfate and filtered. The filtrate was evaporated under reduced pressure, leaving a solid. This solid was triturated in petroleum ether and filtered to yield 17.4 g of 1-(2,4-dibromo-5-methoxyphenyl)-4-difluoromethyl-4,5-dihydro-3-methyl-1,2,4-triazol-5(1H)-one.

The nmr spectrum was consistent with the proposed structure.

Step B 1-(2,4-Dibromo-5-hydroxyphenyl)-4-difluoromethyl-4,5-dihydro-3-methyl-1,2,4-triazol-5(1H)-one A mixture of 17.2 g (0.042 mole) of 1-(2,4-dibromo-5-methoxyphenyl)-4-difluoromethyl-4,5-dihydro-3-methyl-1,2,4-triazol-5-(1H)-one and 50.6 g (0.020 mole) of boron tribromide in 100 mL of methylene chloride was stirred at room temperature for 18 hours. The mixture was washed with 50 mL of water, and the organic phase was dried over anhydrous magnesium sulfate. This mixture was filtered, and the filtrate was evaporated under reduced pressure to yield 16.1 g of 1-(2,4-dibromo-5-hydroxyphenyl)4-difluoromethyl-4,5-dihydro-3-methyl-1,2,4-triazol-5-(1H)-one as a solid.

The nmr spectrum was consistent with the proposed structure.

Step C Ethyl 2-[2,4-dibromo-5-(4-difluoromethyl-4,5-dihydro-3-methyl-5-oxo-1H-1,2,4-triazol-1-yl)-phenoxy]propionate To a stirred solution of 1.25 g (0.0031 mole) of 1-(2,4-dibromo-5-hydroxyphenyl)-4-difluoromethyl-4,5-dihydro-3-methyl-1,2,4-triazol-5(1H)-one in 60 mL of N,N-dimethylformamide was added 0.57 g (0.0033 mole) of ethyl 2-bromopropionate. The resultant mixture was heated at 130° . for two hours, then was cooled. The solvent was evaporated from the mixture under reduced pressure, leaving a solid. This solid was dissolved in diethyl ether, and the solution was washed first with water, then with an aqueous 10% sodium hydroxide solution. The organic solution was dried over anhydrous magnesium sulfate and filtered. The filtrate was evaporated under reduced pressure to yield 1.0 g of ethyl 2-[2,4-dibromo-5-(4-difluoromethyl-4,5-dihydro-3-methyl-5-oxo-1H-1,2,4-triazol-1-yl)phenoxy]propionate as an oil, Compound 8.

The nmr spectrum was consistent with the proposed structure.

EXAMPLE 8

1-Methylpropyl 2-[2,4-dichloro-5-(4-difluoromethyl-4,5-dihydro-3-methyl-5-oxo-1H-1,2,4-triazol-1-yl)phenoxy]propionate To a stirred solution of 1.0 g (0.0025 mole) of 2-[2,4-dichloro-5-(4-difluoromethyl-4,5-dihydro-3-methyl-5-oxo-1H-1,2,4-triazoll-yl)phenoxy]propionyl chloride (prepared in Example 6, Step A) in 15 mL of sec-butanol was added 0.27 g (0.0027 mole) of triethylamine. The reaction mixture was stirred at room temperature for 20 minutes, then heated at 70° C. for 1½ hours. The mixture was allowed to cool and was stirred at room temperature for approximately 18 hours. The solvent was removed by evaporation under reduced pressure, leaving a residue which was partitioned between deithyl ether and water. The organic phase was washed in succession with water, an aqueous 10% sodium hydroxide solution, water, aqueous 10% hydrochloric acid, a saturated aqueous sodium bicarbonate solution, and water. The organic phase was dried over anhydrous magnesium sulfate, then filtered. The filtrate was evaporated under reduced pressure to yield 0.42 g of 1-methylpropyl 1-[2,4-dichloro-5-(4-difluoromethyl-4,5-dihydro-3-methyl-5-oxo-1H-1,2,4-triazol-1-yl)-phenoxy]propionate as an oil, Compound 12.

The nmr spectrum was consistent with the proposed structure.

Compound B4 was also prepared by the method of Example 8 from the acid chloride of Compound A2 and 2-propyn-1-ol.

EXAMPLE 9

Ethyl [2,4-dichloro-5-(4-difluoromethyl-4,5-dihydro-3-methyl-5-oxo-1H-1,2,4-triazol-1-yl)phenoxy]fluoroacetate To a stirred mixture of 2.0 g (0.0065 mole) of 1-(2,4-dichloro-5-hydroxyphenyl)-4-difluoromethyl-4,5-dihydro-3-methyl-1,2,4-triazol-5(1H)-one and 0.91 g (0.0065 mole) of ethyl chlorofluoroacetate in 50 mL of ethanol was added a solution of 0.15 g (0.0065 mole) of sodium in 5 mL of ethanol. The reaction mixture was heated at reflux for 34 hours. The mixture was cooled, and the solvent was removed by evaporation under reduced pressure, leaving a residue. This residue was dissolved in diethyl ether, and the solution was washed first with water, followed by an aqueous 10% sodium hydroxide solution. The organic phase was dried over anhydrous magnesium sulfate, then filtered. The filtrate was evaporated under reduced pressure to yield 0.95 g of ethyl [2,4-dichloro-5-(4-difluoromethyl-4,5-dihydro-3-methyl-5-oxo-1H-1,2,4-triazol-1-yl)phenoxy]fluroacetate as an oil, Compound 51.

The nmr spectrum was consistent with the proposed structure.

EXAMPLE 10

Ethyl 2-[2,4-dichloro-5-(4-fluoromethyl-4,5-dihydro-3-methyl-5-oxo-1H-1,2,4-triazol-1-yl)phenoxy]propionate Step A 1-[2,4-Dichloro-5-(1-methylethoxy)phenyl]-4-fluoromethyl-4,5-dihydro-3-methyl-1,2,4-triazol-5(1H)-one A solution of 6.0 g (0.020 mole) of 1-[2,4-dichloro-5-(1-methylethoxy)phenyl]-4,5-dihydro-3-methyl-1,2,4-triazol-5(1H)-one in 45 mL of N,N-dimethylformamide was added to 0.55 g (0.022 mole) of sodium hydride in 30 mL of N,N-dimethylformamide. The reaction mixture was stirred at room temperature for 15 minutes.

Chlorofluoromethane was added dropwise to the stirred reaction mixture by condensing the gas on a dry ice condenser. During the addition the mixture was heated slowly to 60° C. at which point the mixture began to reflux. The addition of chlorofluromethane was discontinued, and the reaction mixture was allowed to cool to room temperature and stand for approximately 18 hours. Heating at reflux was resumed, and an additional amount of chlorofluoromethane was added during a ten minute period. After complete addition, the reaction mixture was heated at reflux for one hour, then allowed to cool. The solvent was removed by distillation under reduced pressure, leaving a residue. This residue was partitioned between diethyl ether and water. The organic phase was washed first with 1N sodium hydroxide, then water. The organic solution was dried over anhydrous magnesium sulfate and filtered. The filtrate was evaporated under reduced pressure to yield 3.8 g of 1-[2,4-dichloro-5-(1-methylethoxy)phenyl]-4-fluoromethyl-4,5-dihydro-3-methyl-1,2,4-triazol-5(1H)-one as an oil.

The nmr spectrum was consistent with the proposed structure.

Step B 1-(2,4-Dichloro-5-hydroxyphenyl)-4-fluoromethyl-4,5-dihydro-3-methyl-1,2,4-triazol-5(1H)-one To 5 mL of stirring concentrated sulfuric acid was added portionwise 0.53 g (0.0016 mole) of 1-[2,4-dichloro-5-(1-methylethoxy)phenyl]-4-fluoromethyl-4,5-dihydro-3-methyl-1,2,4-triazol-5(1H)-one. After complete addition, the mixture was stirred at room temperature for 2.5 hours. The mixture was poured into 100 mL of ice water and stirred for 30 minutes. The aqueous mixture was extracted with diethyl ether, and the extract was washed with water. The organic phase was dried over anhydrous magnesium sulfate and filtered. The filtrate was evaporated under reduced pressure to yield 0.34 g of 1-(2,4-dichloro-5-hydroxyphenyl)-4-fluoromethyl-4,5-dihydro-3-methyl-1,2,4-triazol-5(1H)-one as a solid.

The nmr spectrum was consistent with the proposed structure.

This reaction was repeated using 2.8 g of 1-[2,4-dichloro-5-(1-methylethoxy]-4-fluoromethyl-4,5-dihydro-3-methyl-1,2,4-triazol-5(1H)-one, producing an additional 1.9 g of product.

Step C Ethyl 2-[2,4-dichloro-5-(4-fluoromethyl-4,5-dihydro-3-methyl-5-oxo-1H-1,2,4-triazol-1-yl)-phenoxy]propionate A mixture of 0.56 g (0.0019 mole) of 1-(2,4-dichloro-5-hydroxyphenyl)-4-fluoromethyl-4,5-dihydro-3-methyl-1,2,4-triazol-5(1H)-one and 1.1 g (0.0076 mole) of anhydrous potassium carbonate in 15 mL of acetone was stirred for 15 minutes. Sodium iodide (approximately 0.01 g) and 0.37 g (0.002 mole) of ethyl 2-bromopropionate were added, and the resultant mixture was heated at reflux for 1.5 hours. The mixture was cooled and filtered. The filtrate was evaporated under reduced pressure, leaving a residue. This residue was partitioned between diethyl ether and water. The organic phase was washed with water, dried over anhydrous magnesium sulfate, and filtered. The filtrate was evaporated under reduced pressure, leaving an oil. This oil was stirred in n-pentane, and the supernant was decanted, leaving an oily residue. The oil was dried at 70° C. under a stream of nitrogen to yield 0.70 g of ethyl 2-[2,4-dichloro-5-(4-fluoromethyl-4,5-dihydro-3-methyl-5-oxo-1H-1,2,4-triazol-1-yl)phenoxy]propionate, Compound 13.

The nmr spectrum was consistent with the proposed structure.

EXAMPLE 11

N-(4-Methylphenylsulfonyl)-2-[2-chloro-4-fluoro-5-(4-difluoromethyl-4,5-dihydro-3-methyl-5-oxo-1H-1,2,4-triazol-1-yl)phenoxy]propionamide A stirred mixture of 0.78 g (0.0021 mole) of 2-[2-chloro-4-fluoro-5-(4-difluoromethyl-4,5-dihydro-3-methyl-5-oxo-1H-1,2,4-triazol-1-yl)phenoxy]propionic acid, 0.42 g (0.0021 mole) of p-toluenesulfonyl isocyanate and 0.05 g (0.0004 mole) of 4-dimethylaminopyridine in 50 mL of toluene was heated at reflux for approximately 18 hours. The mixture was allowed to cool to room temperature and was stirred for 24 hours. The solvent was removed by evaporation at reduced pressure to leave a residue. This residue was purified by column chromatography on silica gel, eluting with toluene:ethyl acetate (1:1). The appropriate fractions were combined and evaporated under reduced pressure to yield 0.7 g of N-(4-methylphenylsulfonyl)-2-[2-chloro-4-fluoro-5-(4-difluoromethyl-4,5-dihydro-3-methyl-5-oxo-1H-1,2,4-triazol-1-yl)phenoxy]propionamide as a solid, Compound C10.

The nmr spectrum was consistent with the proposed structure.

Compound C25 was prepared by the method of Example 11 using 2-chlorobenzenesulfonyl isocyanate.

Example 12

2-[2-Chloro-4-fluoro-5-(4-difluoromethyl-4,5-dihydro-3-methyl-5-oxo-1H-1,2,4-triazol-1-yl) phenoxy]propionic acid, sodium salt.

A mixture of 1.0 g (0.0027 mole) of 2-[2-chloro-4-fluoro-5-(4-difluoromethyl-4,5-dihydro-3-methyl-5-oxo-1H-1,2,4-triazol-1-yl)phenoxy]propionic acid and 0.07 g (0.0027 mole) of sodium hydride in 30 mL of tetrahydrofuran was stirred at room temperature for approximately 18 hours. The solvent was removed by evaporation to yield 0.9 g of 2-[2-chloro-4-fluoro-5-(4-difluoromethyl-4,5-dihydro-3-methyl-5-oxo-1H-1,2,4-triazol-1-yl) phenoxy]propionic acid, sodium salt as a solid, Compound A4.

Compounds C19 and C20 were prepared by the method of Example 12 from compounds C18 and C10 respectively. Compound A6 was prepared by a method analogous to that of Example 12 from Compound A2, substituting isopropylamine for sodium hydride.

Example 13

[2,4-Dichloro-5-(3-difluoromethyl-4,5-dihydro-4-methyl-5-oxo-1H-1,2,4-triazol-1-yl)phenoxy]acetamide Step A Ethyl difluoroacetylcarbamate During a 30 minute period 65.4 g (0.55 mole) of thionyl chloride was added to 50.0 g (0.52 mole) of difluoroacetic acid while stirring. Gas evolved during the addition was returned to the reaction mixture by condensation on a dry ice condenser. After complete addition, the mixture was stirred at room temperature for approximately two hours. Urethane, 46.4 g (0.52 mole), was added and, after complete addition, the reaction mixture was heated at 60°-70° C. for three hours. The mixture was cooled to room temperature and stirred for approximately 18 hours. The mixture was heated at about 75° C. for two hours, then cooled. The mixture was evaporated under reduced pressure to leave an oily residue. This residue crystallized upon standing. The crystallized residue was washed with petroleum ether and filtered to yield 68.4 g of ethyl difluoroacetylcarbamate (mp 55°-57° C.).

Step B 1-[2,4-Dichloro-5-(1-methylethoxy)phenyl]-3-difluoromethyl-4,5-dihydro-1,2,4-triazol-5(1H)-one To a stirred solution of 11.8 g (0.05 mole) of 2,4-dichloro-5-(1-methylethoxy)phenylhydrazine and 10.0 g (0.06 mole) of ethyl difluoroacetylcarbamate in 130 mL of xylene was added 2.5 g (0.02 mole) of phosphorus pentoxide. After complete addition the mixture was heated at reflux for 1.5 hours then allowed to cool to room temperature for approximately 18 hours. The reaction mixture was decanted from a dark residue in the reaction flask and washed with water. The washed mixture was extracted with a 10% aqueous sodium hydroxide solution. The basic extract was made acidic with concentrated hydrochloric acid to form an oily precipitate. This aqueous phase was decanted from the oily residue and fresh water added to wash the residue. This residue was dissolved in 160 mL of methylene chloride and filtered through a celite pad. The filtrate was dried over anhydrous magnesium sulfate and filtered. The filtrate was evaporated under reduced pressure to leave a semi-solid residue. The residue was triturated with approximately 125 mL of petroleum ether to provide 8.2 g of 1-[2,4-dichloro-5-(1-methylethoxy)-phenyl]-3-difluoromethyl-4,5-dihydro-1,2,4-triazol-5(1H)-one.

Step C 1-[2,4-Dichloro-5-(1-methylethoxy)phenyl]-3-difluoromethyl-4,5-dihydro-4-methyl-1,2,4-triazol-5(1H)-one.

A stirred mixture of 4.0 g (0.012 mole) of 1-[2,4-dichloro-5-(1-methylethoxy)phenyl]-3-difluoromethyl-4,5-dihydro-1,2,4-triazol-5(1H)-one and 4.1 g (0.03 mole) of potassium carbonate in 160 mL of acetone was heated at reflux for 0.5 hours then cooled to about 50° C. Methyl iodide, 8.4 g (0.06 mole), was added and the mixture stirred at 45° for one hour then at reflux for one hour. The mixture was cooled to room temperature and evaporated under reduced pressure to leave an oil. This oil was partitioned between methylene chloride and water. The organic phase was washed with a 10% aqueous sodium hydroxide solution and then dried over anhydrous magnesium sulfate. The mixture was filtered and the filtrate evaporated under reduced pressure to leave an oil. This oil solidified when stirred with petroleum ether and upon filtration provided 2.6 g of 1-[2,4-dichloro-5-(1-methylethoxy)phenyl]-3-difluoromethyl-4,5-dihydro-4-methyl-1,2,4-triazol-5-(1H)-one (mp 95°-97° C.).

Step D 1-(2,4-Dichloro-5-hydroxyphenyl)-3-difluoromethyl-4,5-dihydro-4-methyl-1,2,4-triazol-5(1H)-one Hydrolysis of 2.2 g (0.0063 mole) of 1-[2,4-dichloro-5-(1-methylethoxy)phenyl]-3-difluoromethyl-4,5-dihydro-4-methyl-1,2,4-triazol-5(1H)-one in 5 mL of concentrated sulfuric acid produced 1.4 g of 1-(2,4-dichloro-5-hydroxyphenyl)-3-difluoromethyl-4,5-dihydro-4-methyl-1,2,4-triazol-5(1H)-one (mp 176°-179° C.).

Step E [2,4-Dichloro-5-(3-difluoromethyl-4,5-dihydro-4-methyl-5-oxo-1H-1,2,4-triazol-1-yl)phenoxy]acetamide In a manner similar to Example 1, the reaction of 0.72 g (0.00023 mole) of 1-(2,4-dichloro-5-hydroxyphenyl)-3-difluromethyl-4,5-dihydro-4-methyl-1,2,4-triazol-5(1H)-one, 0.32 g (0.00023 mole) of potassium carbonate, and 0.47 g (0.00025 mole) of iodoacetamide in 5 mL of acetone produced 0.69 g of [2,4-dichloro-5-(3-difluoromethyl-4,5-dihydro-4-methyl-5-oxo-1H-1,2,4-triazol-1-yl)phenoxy]acetamide (mp 190°-193.5° C).

The nmr spectrum was consistent with the proposed structure.

The following compounds were prepared by the process of S. Chandrasekaran et al., Synthetic Communications, 12(9), 727-731 (1982) from Compound A2 and the following reagents.

| Compound | Reagent |
|---|---|
| B8 | tetrahydrofurfuryl alcohol |

-continued

| Compound | Reagent |
|---|---|
| B9 | methyl hydroxyacetate |
| B10 | 2-methyl-3,3,4,4-tetrafluoro-2-butanol |
| B12 | furfuryl alcohol |
| B13 | N,N—dimethylethanolamine |
| B14 | 3-hydroxytetrahydrofuran |
| B15 | phenol |
| B17 | ethanethiol |
| B18 | ethyl 2-mercaptoacetate |
| B30 | trifluoroethanol |
| B31 | acetone cyanohydrin |
| B32 | benzyl alcohol |
| B33 | 2-propanethiol |
| C11 | O,N—dimethylhydroxylamine hydrochloride |
| C12 | (2-propynyl)amine |
| C13 | aniline |
| C14 | dimethylamine |
| C15 | diethylamine |
| C16 | ethylamine hydrochloride |
| C17 | glycine methyl ester hydrochloride |
| C22 | 2-amino-2-methylpropionitrile |
| C23 | N—methylaniline |

Compound B25 was prepared by the method of Lonord et al., J. Org. Chem. 27,282-284 (1962) from Compound B23.

Compound A5 was prepared by the hydrolysis of Compound 22 using the procedure described by Kurtev et al., Synthesis (1975), 106-108.

Characterizing properties of some of the compounds of the invention are given in Table 6 below.

Example 14

N-(2,5-dimethoxyphenylsulfonyl)-2-[2-chloro-4-fluoro-5-(4-difluoromethyl-4,5-dihydro-3-methyl-5-oxo-1H-1,2,4-triazol-1-yl)phenoxy]propionamide Step A 2,5-Dimethoxyphenylsulfonamide To a stirred solution of 15.0 g (0.063 mole) of 2,5-dimethoxybenzenesulfonyl chloride in 150 mL of tetrahydrofuran was added dropwise 80 mL of ammonia (28% aqueous solution). After complete addition the mixture was allowed to stir for 1.75 hours at room temperature. Upon standing the mixture separated into two phases. The organic phase was removed from the aqueous phase and was evaporated under reduced pressure to leave a solid residue. This residue was recrystallized from hot water (125 mL) and ethanol (40 mL) to yield 13.1 g of 2,5-dimethoxyphenylsulfonamide (mp 146.5-148.5).

The nmr spectrum was consistent with the proposed structure.

Step B N-(2,5-Dimethoxyphenylsulfonyl)-2-bromo-propionamide

A stirred mixture of 7.0 g (0.032 mole) of 2,5-dimethoxyphenylsulfonamide in 10 mL of 2-bromopropionyl chloride was heated at reflux for 40 minutes then allowed to cool to room temperature. The resultant solution was poured into petroleum ether. Crystals formed after scratching the sides of the flask and were collected by filtration. The filter cake was washed four times with fresh petroleum ether to yield 10.3 g of N-(2,5-dimethoxyphenylsulfonyl)-2-bromopropionamide (mp 116°-118° C.).

The nmr spectrum was consistent with the proposed structure.

Step C N-(2.5-Dimethoxyphenylsulfonyl)-2-[2-chloro-4-fluoro-5-(4-difluoromethyl-4,5-dihydro-3-methyl-5-oxo-1H-1,2,4-triazol-1-yl)phenoxy]propionamide To a stirred solution of 0.75 g (0.0026 mole) of 1-(4-chloro-2-fluoro-5-hydroxyphenyl)-4-difluoromethyl-4,5-dihydro-3-methyl-1,2,4-triazol-5(1H)-one and 0.89 g (0.0026 mole) of N-(2,5-dimethoxyphenylsulfonyl)-2-bromopropionamide in 50 mL of acetone was added 1.04 g (0.0026 mole) of potassium carbonate. After complete addition the mixture was heated at 45° C. for two days. The resultant mixture was cooled and the solvent was removed by evaporation under reduced pressure to leave a residue. The residue was dissolved in 100 mL of water. The aqueous solution was acidified by the dropwise addition of concentrated hydrochloric acid producing a precipitate. The precipitate was collected by filtration. The filter cake was washed with water and then dried under reduced pressure to leave 1.23 g of N-(2,5-dimethoxyphenylsulfonyl)-2-[2-chloro-4-fluoro-5-(4-difluoromethyl-4,5-dihydro-3-methyl-5-oxo-1H-1,2,4-triazol-1-yl)phenoxy]propionamide (mp 168°-172° C.) Compound C90.

The nmr spectrum was consistent with the proposed structure.

EXAMPLE 15

1-(4-Chloro-2-fluoro-5-methoxyphenyl)-4,5-dihydro-3-methyl-1,2,4-triazol-5(1H)-one as an intermediate Step A N'-(4-Chloro-2-fluoro-5-methoxyphenyl)acetamidrazone A stirred mixture of 1.91 g (0.01 mole) of 4-chloro-2-fluoro-5-methoxyphenylhydrazine and 1.97 g (0.01 mole) of 3-(1-iminoethylmercapto)-1-propanesulfonic acid, inner salt, (prepared by the method of Reid et al, Ann. Chem. 676, 114 (1964)) in 50 mL of anhydrous ethanol was heated at reflux for 1.25 hours. The mixture was cooled and evaporated under reduced pressure to leave 3.96 g of a residue. A portion of this residue, 3.33 g, was dissolved in 50 mL of water. The resultant cloudy solution was filtered through a pad of celite and the filtrate was extracted with methylene chloride. The clarified aqueous solution was basified with approximately 8 mL of an aqueous 10% sodium hydroxide solution. An oil precipitated from the basic mixture and slowly solidified. This solid was collected by filtration. The filter cake was washed with water to yield 1.31 g of N'-(4-chloro-2-fluoro-5-methoxyphenyl)acetamidrazone (mp 106°-107° C.).

The nmr analysis was consistent with the proposed structure.

Analysis calc'd for $C_9H_{11}ClFN_3O$: C 46.66, H 4.79, N 18.14. Found: C 46.10, H 4.81, N 17.70.

Step B 1-(4-Chloro-2-fluoro-5-methoxyphenyl)-4,5-dihydro-3-methyl-1,2,4-triazol-5(1H)-one A solution of 1.71 g (0.0086 mole) of trichloromethyl chloroformate in 5 mL of toluene was added dropwise to a stirred solution of 1.0 g (0.0043 mole) of N'-(4-chloro-2-fluoro-5-methoxyphenyl)acetamidrazone in 50 mL of toluene. After complete addition the mixture was stirred at room temperature for five minutes then was heated slowly until a slow reflux was obtained. Reflux was maintained for approximately 15 minutes. The mixture was cooled and evaporated under reduced pressure to leave 1.22 g of a solid. Approximately 1.0 g of this solid was dissolved in 100 mL of methylene chloride. The resultant solution was filtered and the filtrate was extracted with three 25 mL portions of an aqueous 10% sodium hydroxide solution followed by three 25 mL portions of 1N sodium hydroxide. Each set of three similar extracts were combined and washed with methylene chloride. Both of the washed extracts were acidified with concentrated hydrochloric acid producing a precipitate from each. The solids were collected by filtration to provide 0.3 g and 0.12 g, from the 10% and 1N base solutions respectively, of 1-(4-chloro-2-fluoro-5-methoxyphenyl)-4,5-dihydro-3-methyl-1,2,4-triazol-5(1H)-one (mp 209°-211° C.).

The nmr spectrum was consistent with the proposed structure.

EXAMPLE 16

1-(2,4-Dichloro-5-hydroxyphenyl)-3-chlorodifluoromethyl-4,5-dihydro-4-methyl-1,2,4-triazol-5(1H)-one as an intermediate Step A N'-[2,4-Dichloro-5-(1-methylethoxy)phenyl]-chlorodifluoroacetamidrazone A stirred solution of 9.4 g (0.04 mole) of 2,4-dichloro-5-(1-methylethoxy)phenylhydrazine in 350 mL of absolute methanol was cooled to 0°. Gaseous chlorodifluoroacetonitrile (8.0 g, 0.07 mole) was added to the mixture. After complete addition the mixture was allowed to warm to room temperature and stir for 3.5 hours. The stirring was stopped and the mixture stood at room temperature for two days. The solvent was evaporated for the mixture under reduced pressure to leave 13.86 g of N'-[2,4-dichloro-5-(1-methylethoxy)-phenyl]chlorodifluoroacetamidrazone as an oily residue Step B 1-[2,4-Dichloro-5-(1-methylethoxy)phenyl]-3-chlorodifluoromethyl-4,5-dihydro-1,2,4-triazol-5(1H)-one In a manner similar to Example 15, Step B, the reaction of 13.86 g of the oily residue from Step A plus 2.7 g of similar material prepared in a separate experiment and 19.87 g (0.1 mole) of trichloromethyl chloroformate in 600 mL of toluene produced 5.4 g of 1-[2,4-dichloro-5-(1-methylethoxy)phenyl]-3-chlorodifluoromethyl-4,5-dihydro-1,2,4-triazol-5(1H)-one (mp 115°-119° C.).

The nmr spectrum was consistent with the proposed structure.

Step C 1-[2,4-Dichloro-5-(1-methylethoxy)phenyl]-3-chlorodifluoromethyl-4,5-dihydro-4-methyl-1,2,4-triazol-5(1H)-one In a manner similar to Example 13, Step C, the reaction of 4.0 g (0.011 mole) of 1-[2,4-dichloro-5-(1-methylethoxy)phenyl]-3-chlorodifluoromethyl-4,5-dihydro-1,2,4-triazol-5(1H)-one, 4.26 g (0.03 mole) of methyl iodide, and 2.07 g (0.015 mole) of potassium carbonate in 40 mL of acetone provided 3.74 g of 1-[2,4-dichloro-5-(1-methylethoxy)phenyl]-3-chlorodifluoromethyl-4,5-dihydro-4-methyl-1,2,4-triazol-5(1H)-one as a solid. Recrystallization of a small portion of this solid from ethanol and water provided a pale yellow solid, mp 69°-72° C.

The nmr spectrum was consistent with the proposed structure.

Analysis calc'd for $C_{13}H_{12}Cl_3F_2N_3O_2$: C 40.39, H 3.13, N 10.87. Found: C 40.92, H 3.28, N 10.96.

Step D 1-(2,4-Dichloro-5-hydroxyphenyl)-3-chlorodifluoromethyl-4,5-dihydro-4-methyl-1,2,4-triazol-5(1H)-one Hydrolysis of 2.6 g (0.0067 mole) of 1-[2,4-dichloro-5-(1-methylethoxy)phenyl]-3-chlorodifluoromethyl-4,5-dihydro-4-methyl-1,2,4-triazol-5(1H)-one in 10 mL of concentrated sulfuric acid produced 2.17 g of 1-(2,4-dichloro-5-hydroxyphenyl)-3-chlorodifluoromethyl-4,5-dihydro-4-methyl-1,2,4-triazol-5(1H)-one as a solid (mp 146°-148° C.).

The nmr spectrum was consistent with the proposed structure.

Analysis calc'd for $C_{10}H_6Cl_3F_2N_3O_2$: C 34.86, H 1.76, N 12.20. Found: C 35.30, H 1.59, N 12.25.

HERBICIDAL ACTIVITY

The plant test species used in demonstrating the herbicidal activity of compounds of this invention include cotton (*Gossypium hirsutum* var. Stoneville), soybean (*Glycine max* var. Williams), field corn (*Zea mays* var. Agway 595S), wheat (*Triticum aestivium* var. Prodax), rice (*Oryza sativa*), field bindweed (*Convolvulus arvensis*), morningglory (*Ipomea lacunosa* or *Ipomea hederacea*, velvetleaf (*Abutilon theophrasti*), barnyardgrass (*Echinochloa crus galli*), green foxtail (*Setaria viridis*), and johnsongrass (*Sorghum halepense*), yellow nutsedge (*Cyperus esculentus*).

Seeds or tubers of the plant test species were planted in furrows in steam sterilized sandy loam soil contained in disposable fiber flats. A topping soil of equal portions of sand and sandy loam soil was placed uniformly on top of each flat to a depth of approximately 0.5 cm.

The flats for the preemergence test were watered, then drenched with the appropriate amount of a solution of the test compound in a mixture of acetone and water containing a small amount (up to 0.5% v/v) of sorbitan monolaurate emulsifier/solubilizer. The concentration of the test compound in solution was varied to give a range of application rates, generally 8.0 kg/ha and submultiples thereof. The flats were placed in a greenhouse and watered regularly at the soil surface for 21 days at which time phytotoxicity data were recorded.

The flats for the postemergence test were placed in a greenhouse and watered for 8-10 days, then the foilage of the emerged test plants was sprayed with a solution of the test compound in acetone-water containing up to 0.5% sorbitan monolaurate. After spraying, the foilage was kept dry for 24 hours, then watered regularly for 21 days, and phytotoxicity data recorded.

Phytotoxicity data were taken either as percent kill or percent control. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The present rating system ia as follows:

Herbicide Rating System

| Rating Percent Control | Description of Main Categories | Crop Description | Weed Description |
|---|---|---|---|
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery | Deficient to moderate weed control |
| 60 | | Lasting crop injury no | Moderate weed control |

-continued

| Herbicide Rating System | | | |
|---|---|---|---|
| Rating Percent Control | Description of Main Categories | Crop Description | Weed Description |
| | | recovery | |
| 70 | | Heavy injury and stand loss | Control somewhat less than satisfactory |
| 80 | Severe | Crop nearly destroyed a few survivors | Satisfactory to good weed control |
| 90 | | Only occasional live plants left | Very good to excellent control |
| 100 | Complete effect | Complete crop destruction | Complete weed destruction |

Herbicidal data at selected application rates are given for various compounds of the invention in the tables below. The test compounds are identified in the tables of herbicidal data below by numbers which correspond to those used above.

In the Tables of herbicidal data below:
"kg/ha" is kilograms per hectare,
"% K" is percent kill, and
"% C" is percent control.

For herbicidal application, the active compounds as above defined are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, water-soluble or water-dispersible granules, as powdery dusts, as wettable powders, as emulsifiable concentrates, as solutions or as any of several other known types of formulations, depending on the desired mode of application.

For preemergence application these herbicidal compositions are usually applied either as sprays, dusts, or granules to the areas in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently, additional wetting agent and/or oil will be added to the tank-mix for postemergence application to facilitate dispersion on the foliage and absorption by the plant.

Other useful formulations for herbicidal applications are emulsifiable concentrates. Emulsifiable concentrates are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing or emulsifying agents used in agricultural formulations include, for example, the alkyl and alkylaryl sulfonates and sulfates and their sodium salts; polyhydric alcohols; and other types of surface active agents, many of which are available in commerce. The surface active agent, when used, normally comprises 1% to 15% by weight of the herbicidal composition.

Other useful formulations for herbicidal applications include simple solutions of the active ingredient in a dispersant in which it is completely soluble at the desired concentration, such as acetone, alkylated naphthalenes, xylene or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442, incorporated herein by reference, are useful herein with the present herbicidal compounds.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, for example, 7 g/ha or lower.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl- 6-methylphenyl)-N-(2-methoxy-1-methylethyl)-acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]-amino-2-methylpropanenitrile (cyanazine); dinitrolaniline herbicides such as 2,6-dinitro-N,N-dipropyl-4-(trifluoromethyl)-benzeneamine (trifluralin); and aryl urea herbicides such as N'-(3,4-dichlorophenyl)-N,N-dimethylurea (diuron) and N,N-dimethyl-N'-[3-(trifluoromethyl)phenyl-]urea (fluometuron).

It is apparent that various modifications may be made in the formulation and application of the compounds of this invention, without departing from the inventive concepts herein, as defined in the following claims.

TABLE 1

| | Percent Control | | | |
|---|---|---|---|---|
| | Pre-Emergent | | Post-Emergent | |
| PLANT | A | B | A | B |
| Cotton | 50 | 0 | 90 | 40 |
| Soybean | 10 | 0 | 0 | 10 |
| Corn | 0 | 0 | 0 | 0 |
| Rice | 50 | 20 | 40 | 0 |
| Wheat | 30 | 0 | 40 | 20 |
| Field Bindweed | 60 | 0 | 40 | 0 |
| Morningglory | 20 | 0 | 60 | 10 |
| Velvetleaf | 100 | 0 | 100 | 0 |
| Barnyardgrass | 70 | 0 | 90 | 0 |
| Green foxtail | 100 | 70 | 90 | 0 |
| Johnsongrass | 40 | 0 | 10 | 0 |
| Yellow nutsedge | 30 | 0 | 10 | 0 |

TABLE 2

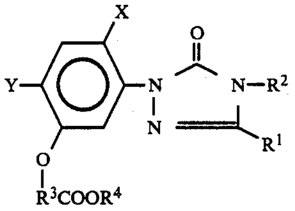

| Cmpd. No. | X | Y | $R^1$ | $R^2$ | $R^3$ | $R^4$ |
|---|---|---|---|---|---|---|
| 1 | Cl | Cl | $CH_3$ | $CHF_2$ | $CH_2$ | $CH_3$ |
| 2 | Cl | Cl | $CH_3$ | $CHF_2$ | $CH(CH_3)$ | $CH_3$ |
| 3 | F | Cl | $CH_3$ | $CHF_2$ | $CH(CH_3)$ | $CH_3$ |
| 4 | Cl | $CH_3$ | $CH_3$ | $CHF_2$ | $CH(CH_3)$ | $CH_3$ |
| 5 | Cl | Cl | $CH_3$ | $CHF_2$ | $CH(CH_3)$ | $C_2H_5$ |
| 6 | F | Cl | $CH_3$ | $CHF_2$ | $CH(CH_3)$ | $C_2H_5$ |
| 7 | Cl | $CH_3$ | $CH_3$ | $CHF_2$ | $CH(CH_3)$ | $C_2H_5$ |
| 8 | Br | Br | $CH_3$ | $CHF_2$ | $CH(CH_3)$ | n-$C_2H_5$ |
| 9 | Cl | Cl | $CH_3$ | $CHF_2$ | $CH(CH_3)$ | $C_3H_7$ |
| 10 | Cl | Cl | $CH_3$ | $CHF_2$ | $CH(CH_3)$ | $CH(CH_3)_2$ |
| 11 | Cl | Cl | $CH_3$ | $CHF_2$ | $CH(CH_3)$ | $C_4H_9$ |
| 12 | Cl | Cl | $CH_3$ | $CHF_2$ | $CH(CH_3)$ | $CH(CH_3)C_2H_5$ |
| 13 | Cl | Cl | $CH_3$ | $CH_2F$ | $CH(CH_3)$ | $C_2H_5$ |
| 14 | F | Cl | $CH_3$ | $CHF_2$ | $CH_2$ | $CH_3$ |
| 15 | F | Cl | $CH_3$ | $CHF_2$ | $CH(CH_3)$ | n-$C_3H_7$ |
| 16 | F | Cl | $CH_3$ | $CHF_2$ | $CH(CH_3)$ | $CH(CH_3)_2$ |
| 17 | Cl | Cl | $CH_3$ | $CHF_2$ | $CH_2$ | $C_2H_5$ |
| 18 | Cl | Cl | $CH_3$ | $CHF_2$ | $CH_2CH_2CH_2$ | $C_2H_5$ |
| 19 | F | Cl | $CH_3$ | $CHF_2$ | $CH(CH_3)$ | $C(CH_3)_3$ |
| 20 | F | Cl | $CH_3$ | $CHF_2$ | $C(CH_3)_2$ | $C_2H_5$ |
| 21 | Cl | Cl | $CH_3$ | $CHF_2$ | $CH_2$ | $C(CH_3)_3$ |
| 22 | F | Cl | $CH_3$ | $CHF_2$ | $CH_2$ | $C(CH_3)_3$ |
| 23 | Cl | $CH_2F$ | $CH_3$ | $CHF_2$ | $CH(CH_3)$ | $C_2H_5$ |
| 24 | F | Cl | $CH_3$ | $CHF_2$ | $CH(CH_3)$ | $CH_2CH(CH_3)_2$ |
| 25 | F | F | $CH_3$ | $CHF_2$ | $CH(CH_3)$ | $C_2H_5$ |
| 26 | Cl | F | $CH_3$ | $CHF_2$ | $CH(CH_3)$ | $C_2H_5$ |
| 27 | Cl | $CH_2F$ | $CH_3$ | $CHF_2$ | $CH(CH_3)$ | $C_2H_5$ |
| 28 | F | $CH_2F$ | $CH_3$ | $CHF_2$ | $CH(CH_3)$ | $C_2H_5$ |
| 29 | F | $CH_3$ | $CH_3$ | $CHF_2$ | $CH(CH_3)$ | $C_2H_5$ |
| 30 | Cl | $CH_2OCH_3$ | $CH_3$ | $CHF_2$ | $CH(CH_3)$ | $CH_3$ |
| 31 | Cl | $CH_2SO_2CH_3$ | $CH_3$ | $CHF_2$ | $CH_2$ | $C_2H_5$ |
| 32 | F | $CH_2SCH_2CH{=}CH_2$ | $CH_3$ | $CHF_2$ | $CH(CH_3)$ | $C_2H_5$ |
| 33 | F | $CH_2OCH_2C{\equiv}CH$ | $CH_3$ | $CHF_2$ | $CH(CH_3)$ | $C_2H_5$ |
| 34 | F | Cl | Cl | $CHF_2$ | $CH(CH_3)$ | $C_2H_5$ |
| 35 | F | Cl | $C_2H_5$ | $CHF_2$ | $CH(CH_3)$ | $C_2H_5$ |
| 36 | F | Cl | $CH_2CN$ | $CHF_2$ | $CH(CH_3)$ | $C_2H_5$ |
| 37 | F | Cl | $CH_2SCH_3$ | $CHF_2$ | $CH(CH_3)$ | $C_2H_5$ |
| 38 | F | Cl | $CHF_2$ | $CHF_2$ | $CH(CH_3)$ | $CH_3$ |
| 39 | F | Cl | $CF_3$ | $CHF_2$ | $CH(CH_3)$ | $CH(CH_3)_2$ |
| 40 | F | Cl | 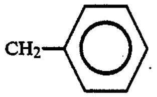 | $CHF_2$ | $CH_2$ | $C_2H_5$ |
| 41 | F | Cl | $SCH_3$ | $CHF_2$ | $CH(CH_3)$ | $CH_3$ |

TABLE 2-continued

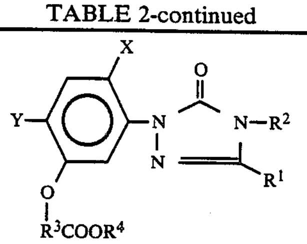

| Cmpd. No. | X | Y | $R^1$ | $R^2$ | $R^3$ | $R^4$ |
|---|---|---|---|---|---|---|
| 42 | F | Cl | $SO_2CH_3$ | $CHF_2$ | $CH(CH_3)$ | $CH_3$ |
| 43 | F | Cl | $CH_2SO_2CH_3$ | $CHF_2$ | $CH(CH_3)$ | $C_2H_5$ |
| 44 | F | Cl | $CH_3$ | $CH_2F$ | $CH_2$ | $C_2H_5$ |
| 45 | F | $CH_2SOCH_2CH_3$ | $CH_3$ | $CHF_2$ | $CH(CH_3)$ | $CH_3$ |
| 46 | F | $CH_2SCH_2CH{\equiv}CH$ | $CH_3$ | $CHF_2$ | $CH_2$ | $C_2H_5$ |
| 47 | F | $CH_2OCH_2CH{=}CHCH_3$ | $CH_3$ | $CHF_2$ | $CH(CH_3)$ | $CH_3$ |
| 48 | F | $CH_2SCH_2C(CH_3){=}CH_2$ | $CH_3$ | $CHF_2$ | $CH_2$ | $CH_3$ |
| 49 | $CF_3$ | Cl | $CH_3$ | $CHF_2$ | $CH(CH_3)$ | $C_2H_5$ |
| 50 | F | 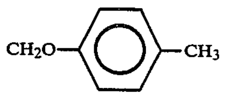 | $CH_3$ | $CHF_2$ | $CH(CH_3)$ | $C_2H_5$ |
| 51 | Cl | Cl | $CH_3$ | $CHF_2$ | CHF | $C_2H_5$ |
| 52 | F | Cl | $CHF_2$ | $CH_3$ | $CH(CH_3)$ | $C(CH_3)_3$ |
| 53 | F | Cl | $CHF_2$ | $CH_3$ | $CH(CH_3)$ | $CH_3$ |
| 54 | F | Cl | $CHF_2$ | $CH_3$ | $CH(CH_3)$ | n-$C_3H_7$ |
| 55 | F | Br | $CHF_2$ | $CH_3$ | $CH(CH_3)$ | $C_2H_5$ |
| 56 | F | Br | $CH_3$ | $CHF_2$ | $CH(CH_3)$ | $C_2H_5$ |
| 57 | Br | Br | $CHF_2$ | $CH_3$ | $CH(CH_3)$ | $C_2H_5$ |
| 58 | F | Cl | $CHF_2$ | $CH_3$ | $CH(CH_3)$ | $CH(CH_3)_2$ |
| 59 | F | Cl | $CHF_2$ | $CH_3$ | $CH(CH_3)$ | $CH_2CH(CH_3)_2$ |
| 60 | Cl | Cl | $CHF_2$ | $CH_3$ | $CH(CH_3)$ | $C_2H_5$ |
| 61 | F | Br | $CH_3$ | $CHF_2$ | $CH(CH_3)$ | n-$C_3H_7$ |
| 62 | F | $CF_3$ | $CH_3$ | $CHF_2$ | $CH(CH_3)$ | $C_2H_5$ |
| 63 | F | Br | $CH_3$ | $CHF_2$ | $CH(CH_3)$ | $C(CH_3)_3$ |
| 64 | Cl | Br | $CH_3$ | $CHF_2$ | $CH(CH_3)$ | $C_2H_5$ |
| 65 | Br | Cl | $CH_3$ | $CHF_2$ | $CH(CH_3)$ | $C_2H_5$ |

Other representative compounds are those which are identical with compounds 1-54, 57-60, 62, and 64-65 respectively, except that X is F and Y is Br. Still other representative compounds are those which are identical with compounds 1-61, and 63-65 respectively, except that X is F and Y is $CF_3$.

TABLE 3

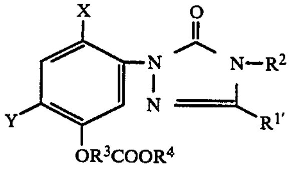

| Cmpd. No. | X | Y | $R^1$ | $R^2$ | $R^3$ | $R^4$ |
|---|---|---|---|---|---|---|
| A1 | Cl | Cl | $CH_3$ | $CHF_2$ | $CH(CH_3)$ | H |
| A2 | F | Cl | $CH_3$ | $CHF_2$ | $CH(CH_3)$ | H |
| A3 | Cl | $CH_3$ | $CH_3$ | $CHF_2$ | $CH(CH_3)$ | H |
| A4 | F | Cl | $CH_3$ | $CHF_2$ | $CH(CH_3)$ | Na |
| A5 | F | Cl | $CH_3$ | $CHF_2$ | $CH_2$ | H |
| A6 | F | Cl | $CH_3$ | $CHF_2$ | $CH(CH_3)$ | $NH_3CH(CH_3)_2$ |
| A7 | F | $CH_3$ | $CH_3$ | $CHF_2$ | $CH(CH_3)$ | H |
| A8 | F | $CH_3$ | $CH_3$ | $CHF_2$ | $CH(CH_3)$ | K |
| A9 | Cl | $CH_2F$ | $CH_3$ | $CHF_2$ | $CH(CH_3)$ | H |
| A10 | Cl | $CH_2F$ | $CH_3$ | $CHF_2$ | $CH(CH_3)$ | $NH_4$ |
| A11 | F | Cl | $CHF_2$ | $CHF_2$ | $CH(CH_3)$ | H |
| A12 | Br | Cl | $CH_2CN$ | $CHF_2$ | $CH(CH_3)$ | H |
| A13 | F | Cl | $CH_2SCH_3$ | $CHF_2$ | $CH_2$ | H |
| A14 | F | Cl | $CF_3$ | $CHF_2$ | $CH(CH_3)$ | H |
| A15 | F | $CH_2OCH_3$ | $CH_3$ | $CHF_2$ | $CH(CH_3)$ | H |
| A16 | F | $CH_3$ | $CH_3$ | $CHF_2$ | $CH(CH_3)$ | H |
| A17 | F | $CH_3$ | $CH_3$ | $CHF_2$ | $CH(CH_3)$ | Na |
| A18 | F | $CH_2SCH_2CH{=}CH_2$ | $CH_3$ | $CHF_2$ | $CH(CH_3)$ | H |
| A19 | F | $CH_2SO_2CH_3$ | $CH_3$ | $CHF_2$ | $CH_2$ | $HN(CH_3)_3$ |

TABLE 3-continued

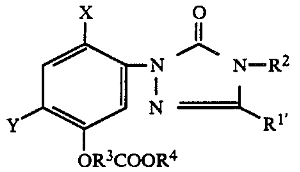

| Cmpd. No. | X | Y | $R^1$ | $R^2$ | $R^3$ | $R^4$ |
|---|---|---|---|---|---|---|
| A20 | F | 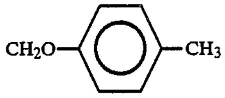 | $CH_3$ | $CHF_2$ | $CH(CH_3)$ | H |
| A21 | F | Cl | $CHF_2$ | $CH_3$ | $CH(CH_3)$ | H |
| A22 | F | Br | $CHF_2$ | $CH_3$ | $CH(CH_3)$ | H |
| A23 | F | Br | $CH_3$ | $CHF_2$ | $CH(CH_3)$ | H |
| A24 | Br | Br | $CH_3$ | $CHF_2$ | $CH(CH_3)$ | H |
| A25 | Br | Br | $CHF_2$ | $CH_3$ | $CH(CH_3)$ | H |
| A26 | F | Cl | $CHF_2$ | $CH_3$ | $CH(CH_3)$ | Na |
| A27 | Cl | Cl | $CHF_2$ | $CH_3$ | $CH(CH_3)$ | H |
| A28 | Cl | Br | $CH_3$ | $CHF_2$ | $CH(CH_3)$ | H |
| A29 | Br | Cl | $CH_3$ | $CHF_2$ | $CH(CH_3)$ | H |

Other representative compounds are those which are identical with compounds A1–A21, and A24–A29 respectively, except that X is F and Y is Br. Still other representative compounds are those which are identical with compounds A1–A29 respectively, except that X is F and Y is $CF_3$.

TABLE 4

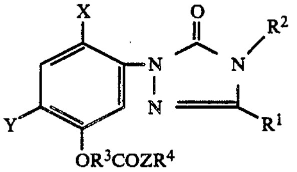

| Cmpd. No. | X | Y | $R^1$ | $R^2$ | $R^3$ | $ZR^4$ |
|---|---|---|---|---|---|---|
| B1 | Cl | Cl | $CH_3$ | $CHF_2$ | $CH(CH_3)$ | $OCH_2CH(NO_2)CH_3$ |
| B2 | Cl | Cl | $CH_3$ | $CHF_2$ | $CH(CH_3)$ | $OCH_2CH{=}CH_2$ |
| B3 | Cl | Cl | $CH_3$ | $CHF_2$ | $CH(CH_3)$ | $OCH_2C{\equiv}CH$ |
| B4 | F | Cl | $CH_3$ | $CHF_2$ | $CH(CH_3)$ | $OCH_2C{\equiv}CH$ |
| B5 | Cl | Cl | $CH_3$ | $CHF_2$ | $CH(CH_3)$ | $OCH_2CH_2OCH_3$ |
| B6 | F | Cl | $CH_3$ | $CHF_2$ | $CH(CH_3)$ | $OCH(CH_3)C{\equiv}CH$ |
| B7 | F | Cl | $CH_3$ | $CHF_2$ | $CH(CH_3)$ | $OC(CH_3)_2C{\equiv}CH$ |
| B8 | F | Cl | $CH_3$ | $CHF_2$ | $CH(CH_3)$ | 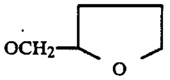 |
| B9 | F | Cl | $CH_3$ | $CHF_2$ | $CH(CH_3)$ | $OCH_2CO_2CH_3$ |
| B10 | F | Cl | $CH_3$ | $CHF_2$ | $CH(CH_3)$ | $OC(CH_3)_2CF_2CHF_2$ |
| B11 | F | Cl | $CH_3$ | $CHF_2$ | $CH(CH_3)$ | $OCH_2CN$ |
| B12 | F | Cl | $CH_3$ | $CHF_2$ | $CH(CH_3)$ | 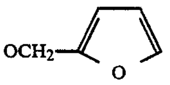 |
| B13 | F | Cl | $CH_3$ | $CHF_2$ | $CH(CH_3)$ | $OCH_2CH_2N(CH_3)_2$ |
| B14 | F | Cl | $CH_3$ | $CHF_2$ | $CH(CH_3)$ | 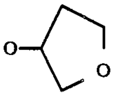 |
| B15 | F | Cl | $CH_3$ | $CHF_2$ | $CH(CH_3)$ | 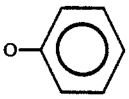 |

TABLE 4-continued

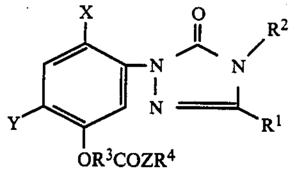

| Cmpd. No. | X | Y | $R^1$ | $R^2$ | $R^3$ | $ZR^4$ |
|---|---|---|---|---|---|---|
| B16 | F | Cl | $CH_3$ | $CHF_2$ | $CH(CH_3)$ | 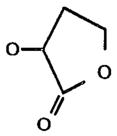 |
| B17 | F | Cl | $CH_3$ | $CHF_2$ | $CH(CH_3)$ | $SC_2H_5$ |
| B18 | F | Cl | $CH_3$ | $CHF_2$ | $CH(CH_3)$ | $SCH_2CO_2C_2H_5$ |
| B19 | Cl | Cl | $CH_3$ | $CHF_2$ | CHF | $SC_2H_5$ |
| B20 | F | Cl | $CH_3$ | $CHF_2$ | $CH(CH_3)$ | $OCH_2CH_2N(CH_3)_3Cl$ |
| B21 | F | Cl | $CH_3$ | $CHF_2$ | $CH(CH_3)$ | $OCH_2CON(C_2H_5)_2$ |
| B22 | F | Cl | $CH_3$ | $CHF_2$ | $CH(CH_3)$ | $OCH_2OCH_3$ |
| B23 | F | Cl | $CH_3$ | $CHF_2$ | $CH(CH_3)$ | $OCH_2SCH_3$ |
| B24 | F | Cl | $CH_3$ | $CHF_2$ | $CH(CH_3)$ | $OCH_2S(O)CH_3$ |
| B25 | F | Cl | $CH_3$ | $CHF_2$ | $CH(CH_3)$ | $OCH_2SO_2CH_3$ |
| B26 | F | Cl | $CH_3$ | $CHF_2$ | $CH(CH_3)$ | 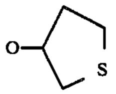 |
| B27 | F | Cl | $CH_3$ | $CHF_2$ | $CH(CH_3)$ | 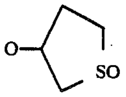 |
| B28 | F | Cl | $CH_3$ | $CHF_2$ | $CH(CH_3)$ | 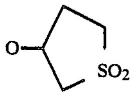 |
| B29 | F | Cl | $CH_3$ | $CHF_2$ | $CH(CH_3)$ | 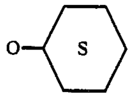 |
| B30 | F | Cl | $CH_3$ | $CHF_2$ | $CH(CH_3)$ | $OCH_2CF_3$ |
| B31 | F | Cl | $CH_3$ | $CHF_2$ | $CH(CH_3)$ | $OC(CH_3)_2CN$ |
| B32 | F | Cl | $CH_3$ | $CHF_2$ | $CH(CH_3)$ | 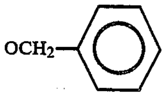 |
| B33 | F | Cl | $CH_3$ | $CHF_2$ | $CH(CH_3)$ | $SCH(CH_3)_2$ |
| B34 | F | Cl | $CH_3$ | $CHF_2$ | $CH(CH_3)$ | 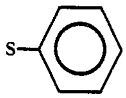 |
| B35 | F | Cl | $CH_3$ | $CHF_2$ | $CH(CH_3)$ | 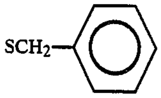 |
| B36 | F | Cl | $CH_3$ | $CHF_2$ | $CH(CH_3)$ | $SCH_2CH{=}CH_2$ |
| B37 | F | $CH_3$ | $CH_3$ | $CHF_2$ | $CH(CH_3)$ | $SC_2H_5$ |
| B38 | F | $CH_3$ | $CH_3$ | $CHF_2$ | $CH(CH_3)$ | $OCH_2SCH_3$ |
| B39 | F | $CH_3$ | $CH_3$ | $CHF_2$ | $CH(CH_3)$ | $OCH_2S(O)CH_3$ |
| B40 | F | $CH_3$ | $CH_3$ | $CHF_2$ | $CH(CH_3)$ | $OCH_2SO_2CH_3$ |
| B41 | F | $CH_3$ | $CH_3$ | $CHF_2$ | $CH(CH_3)$ | $OCH_2CN$ |

TABLE 4-continued

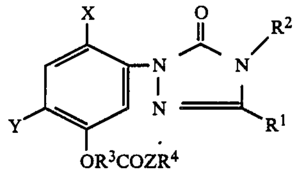

| Cmpd. No. | X | Y | $R^1$ | $R^2$ | $R^3$ | $ZR^4$ |
|---|---|---|---|---|---|---|
| B42 | F | $CH_2F$ | $CH_3$ | $CHF_2$ | $CH(CH_3)$ | 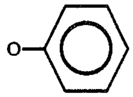 |
| B43 | F | $CH_3$ | $CH_3$ | $CHF_2$ | $CH(CH_3)$ | 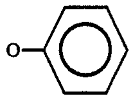 |
| B44 | Cl | Cl | $CH_3$ | $CHF_2$ | $CH(CH_3)$ | 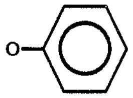 |
| B45 | Cl | Cl | $CH_3$ | $CHF_2$ | $CH(CH_3)$ | $OCH_2SCH_3$ |
| B46 | Cl | Cl | $CH_3$ | $CHF_2$ | $CH(CH_3)$ | $SC_2H_5$ |
| B47 | Cl | Cl | $CH_3$ | $CHF_2$ | $CH(CH_3)$ | $OCH_2CONH_2$ |
| B48 | Cl | Cl | $CH_3$ | $CHF_2$ | $CH(CH_3)$ | 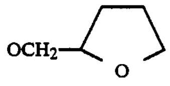 |
| B49 | Cl | Cl | $CH_3$ | $CHF_2$ | $CH(CH_3)$ | 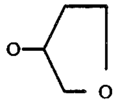 |
| B50 | F | Cl | $CH_3$ | $CHF_2$ | $CH(CH_3)$ | 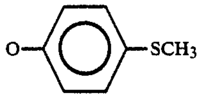 |
| B51 | F | Cl | $CH_3$ | $CHF_2$ | $CH(CH_3)$ | 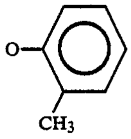 |
| B52 | F | Cl | $CH_3$ | $CHF_2$ | $CH(CH_3)$ | 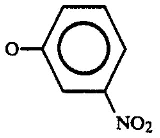 |
| B53 | F | $CH_2OCH_3$ | $CH_3$ | $CHF_2$ | $CH(CH_3)$ | $OCH_2OCH_3$ |
| B54 | F | $CH_2SCH_2CH{=}CH_2$ | $CH_3$ | $CHF_2$ | $CH(CH_3)$ | 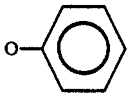 |
| B55 | F | Cl | $CH_3$ | $CHF_2$ | $CH(CH_3)$ | 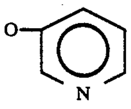 |

TABLE 4-continued

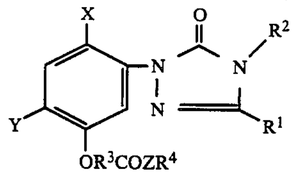

| Cmpd. No. | X | Y | $R^1$ | $R^2$ | $R^3$ | $ZR^4$ |
|---|---|---|---|---|---|---|
| B56 | F | Cl | $CH_3$ | $CHF_2$ | $CH(CH_3)$ | 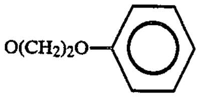 |
| B57 | F | Cl | $CH_3$ | $CHF_2$ | $CH(CH_3)$ | $OCH(OCOCH_3)CH_3$ |
| B58 | F | Cl | $CH_3$ | $CHF_2$ | $CH(CH_3)$ | 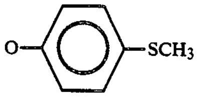 |
| B59 | Cl | Cl | $CH_3$ | $CH_2F$ | $CH_2$ | $OCH_2C(Cl){=}CHCl$ |
| B60 | Cl | Cl | $CH_3$ | $CHF_2$ | $CH_2$ | 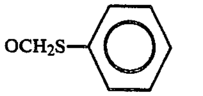 |
| B61 | F | Cl | $CH_3$ | $CHF_2$ | $CH_2$ | 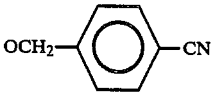 |
| B62 | F | Cl | $CH_3$ | $CHF_2$ | $CH(CH_3)$ | 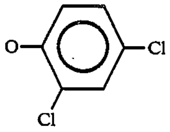 |
| B63 | F | Cl | $CHF_2$ | $CH_3$ | $CH(CH_3)$ | $OCH_2SCH_3$ |
| B64 | F | Cl | $CHF_2$ | $CH_3$ | $CH(CH_3)$ | $OC(CH_3)_2C{\equiv}CH$ |
| B65 | F | Cl | $CHF_2$ | $CH_3$ | $CH(CH_3)$ | $SCH(CH_3)_2$ |
| B66 | F | Cl | $CF_3$ | $CH_3$ | $CH_2$ | $OCH_2CN$ |
| B67 | F | Cl | $CF_2Cl$ | $CH_3$ | $CH(CH_3)$ | 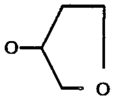 |
| B68 | F | $CH_3$ | $CHF_2$ | $CH_2CN$ | $CH_2$ | $OCH_2OCH_3$ |
| B69 | F | $CH_3$ | $CHF_2$ | $CH_2SCN$ | $CH(CH_3)$ | $OCH_2CH_2N(CH_3)_2$ |
| B70 | F | Cl | $CF_3$ | $CH_2CH{=}CH_2$ | $CH_2$ | 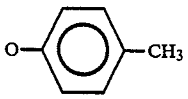 |
| B71 | F | Cl | $CHF_2$ | $CH_2OCH_3$ | $CH_2$ | $OCH_2OCH_3$ |
| B72 | F | Cl | $CHF_2$ | $CH_2SO_2CH_2CH_3$ | $CH(CH_3)$ | $OCH_2CH{=}CH_2$ |
| B73 | F | Cl | $CHF_2$ | $CH_2CH_3$ | $CH(CH_3)$ | $OCH_2C{\equiv}CH$ |
| B74 | F | Cl | $CF_2CF_3$ | $CH_3$ | $CH(CH_3)$ | $OCH_2OCH_3$ |
| B75 | Cl | Cl | $CF_2CF_3$ | $CH_2CH{=}CH_2$ | $CH(CH_3)$ | $OCH_2CN$ |
| B76 | F | Cl | $CHF_2$ | $CHF_2$ | $CH(CH_3)$ | $OCH_2SCH_3$ |
| B77 | F | $CH_2SCH_3$ | $CHF_2$ | $CH_3$ | $CH(CH_3)$ | $OCH_2CH{=}CH_2$ |
| B78 | F | Cl | $CHF_2$ | $CH_3$ | $CH(CH_3)$ | $OCH(CH_3)CONH_2$ |
| B79 | F | Cl | Cl | $CHF_2$ | $CH(CH_3)$ | $OCH_2CN$ |
| B80 | F | Cl | $SCH_3$ | $CHF_2$ | $CH(CH_3)$ | $OCH_2SCH_3$ |
| B81 | F | Cl | $CH_2CN$ | $CHF_2$ | $CH_2$ | $OCH_2CH{=}CH_2$ |

TABLE 4-continued
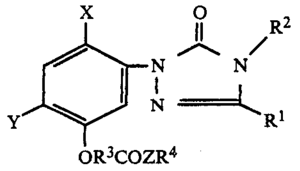
| Cmpd. No. | X | Y | $R^1$ | $R^2$ | $R^3$ | $ZR^4$ |
|---|---|---|---|---|---|---|
| B82 | F | 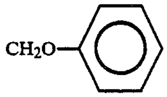 | $CH_3$ | $CHF_2$ | $CH(CH_3)$ | $OCH_2SCH_3$ |
| B83 | F | Cl | $CHF_2$ | $CH_3$ | $CH(CH_3)$ | $SCH_2CO_2CH_3$ |
| B84 | F | Cl | $CH_3$ | $CHF_2$ | $CH(CH_3)$ | 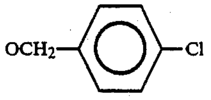 |
| B85 | F | Cl | $CH_3$ | $CHF_2$ | $CH(CH_3)$ | 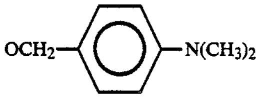 |
| B86 | F | Cl | $CH_3$ | $CHF_2$ | $CH(CH_3)$ | 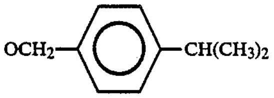 |
| B87 | F | Cl | $CH_3$ | $CHF_2$ | $CH(CH_3)$ | 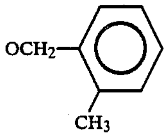 |
| B88 | F | Cl | $CH_3$ | $CHF_2$ | $CH(CH_3)$ | 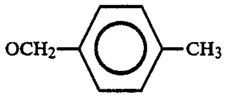 |
| B89 | F | Br | $CH_3$ | $CHF_2$ | $CH(CH_3)$ | 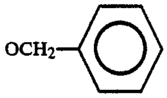 |
| B90 | Br | Br | $CH_3$ | $CHF_2$ | $CH(CH_3)$ | 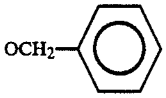 |
| B91 | F | Br | $CH_3$ | $CHF_2$ | $CH(CH_3)$ | $OC(CH_3)_2C{\equiv}CH$ |
| B92 | Cl | Cl | $CHF_2$ | $CH_3$ | $CH(CH_3)$ | 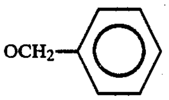 |
| B93 | F | Cl | $CHF_2$ | $CH_3$ | $CH(CH_3)$ | 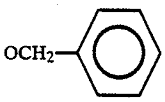 |

TABLE 4-continued

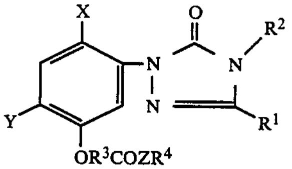

| Cmpd. No. | X | Y | $R^1$ | $R^2$ | $R^3$ | $ZR^4$ |
|---|---|---|---|---|---|---|
| B94 | F | Cl | $CH_3$ | $CHF_2$ | $CH(CH_3)$ | 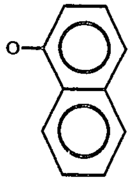 |
| B95 | F | Cl | $CH_3$ | $CHF_2$ | $CH(CH_3)$ | 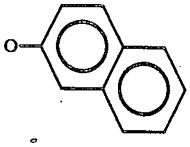 |
| B96 | F | Cl | $CH_3$ | $CHF_2$ | $CH(CH_3)$ | 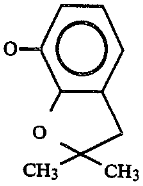 |

Other representative compounds are those which are identical with compounds B1-B88, B-90, and B92-B96 respectively, except that X is F and Y is Br. Still other representative compounds are those which are identical with compounds B1-B96 respectively, except that X is F and Y is $CF_3$.

TABLE 5

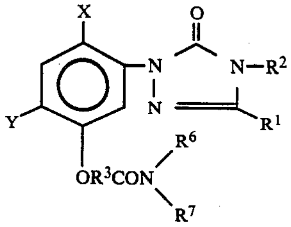

| Cmpd. No. | X | Y | $R^1$ | $R^2$ | $R^3$ | $R^6$ | $R^7$ |
|---|---|---|---|---|---|---|---|
| C1 | Cl | Cl | $CH_3$ | $CHF_2$ | $CH_2$ | H | H |
| C2 | F | Cl | $CH_3$ | $CHF_2$ | $CH(CH_3)$ | $CH_3$ | H |
| C3 | Cl | Cl | $CH_3$ | $CHF_2$ | $CH(CH_3)$ | $SO_2CH_3$ | H |
| C4 | Cl | Cl | $CH_3$ | $CHF_2$ | $CH(CH_3)$ | $SO_2CF_3$ | H |
| C5 | Cl | Cl | $CH_3$ | $CHF_2$ | $CH(CH_3)$ | H | H |
| C6 | Cl | Cl | $CH_3$ | $CHF_2$ | $CH(CH_3)$ | $CH_3$ | H |
| C7 | F | Cl | $CH_3$ | $CHF_2$ | $CH_2$ | H | H |
| C8 | F | Cl | $CH_3$ | $CHF_2$ | $CH_2$ | $C_2H_5$ | $C_2H_5$ |
| C9 | F | Cl | $CH_3$ | $CHF_2$ | $CH(CH_3)$ | $CH(CH_3)C_2H_5$ | H |
| C10 | F | Cl | $CH_3$ | $CHF_2$ | $CH(CH_3)$ | 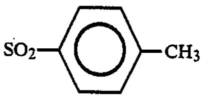 | H |
| C11 | F | Cl | $CH_3$ | $CHF_2$ | $CH(CH_3)$ | $OCH_3$ | $CH_3$ |
| C12 | F | Cl | $CH_3$ | $CHF_2$ | $CH(CH_3)$ | $CH_2C{\equiv}CH$ | H |

TABLE 5-continued

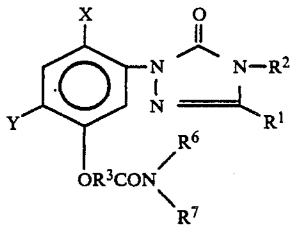

| Cmpd. No. | X | Y | $R^1$ | $R^2$ | $R^3$ | $R^6$ | $R^7$ |
|---|---|---|---|---|---|---|---|
| C13 | F | Cl | $CH_3$ | $CHF_2$ | $CH(CH_3)$ | 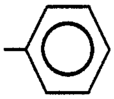 | H |
| C14 | F | Cl | $CH_3$ | $CHF_2$ | $CH(CH_3)$ | $CH_3$ | $CH_3$ |
| C15 | F | Cl | $CH_3$ | $CHF_2$ | $CH(CH_3)$ | $C_2H_5$ | $C_2H_5$ |
| C16 | F | Cl | $CH_3$ | $CHF_2$ | $CH(CH_3)$ | $C_2H_5$ | H |
| C17 | F | Cl | $CH_3$ | $CHF_2$ | $CH(CH_3)$ | $CH_2CO_2CH_3$ | H |
| C18 | F | Cl | $CH_3$ | $CHF_2$ | $CH(CH_3)$ | $SO_2CH_3$ | H |
| C19 | F | Cl | $CH_3$ | $CHF_2$ | $CH(CH_3)$ | $SO_2CH_3$ | Na |
| C20 | F | Cl | $CH_3$ | $CHF_2$ | $CH(CH_3)$ | 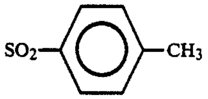 | Na |
| C21 | F | Cl | $CH_3$ | $CHF_2$ | $CH(CH_3)$ | $C(CH_3)_2C{\equiv}CH$ | H |
| C22 | F | Cl | $CH_3$ | $CHF_2$ | $CH(CH_3)$ | $C(CH_3)_2CN$ | H |
| C23 | F | Cl | $CH_3$ | $CHF_2$ | $CH(CH_3)$ | 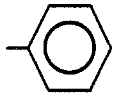 | $CH_3$ |
| C24 | Cl | Cl | $CHF_2$ | $CH_3$ | $CH_2$ | H | H |
| C25 | F | Cl | $CH_3$ | $CHF_2$ | $CH(CH_3)$ | 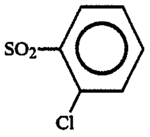 | H |
| C26 | F | Cl | $CH_3$ | $CHF_2$ | $CH(CH_3)$ | H | H |
| C27 | F | Cl | $CH_3$ | $CHF_2$ | $CH(CH_3)$ | $SO_2CF_3$ | H |
| C28 | F | Cl | $CH_3$ | $CHF_2$ | $CH(CH_3)$ | $SO_2CF_3$ | Na |
| C29 | F | Cl | $CH_3$ | $CHF_2$ | $CH(CH_3)$ | 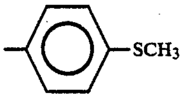 | H |
| C30 | F | Cl | $CH_3$ | $CHF_2$ | $CH(CH_3)$ | $SO_2CH_3$ | $CH_3$ |
| C31 | F | Cl | $CH_3$ | $CHF_2$ | $CH(CH_3)$ | 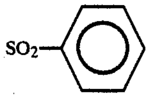 | $CH_3$ |
| C32 | F | Cl | $CH_3$ | $CHF_2$ | $CH(CH_3)$ | 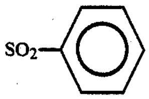 | H |
| C33 | F | Cl | $CH_3$ | $CHF_2$ | $CH_2$ | $SO_2CH_3$ | H |

TABLE 5-continued

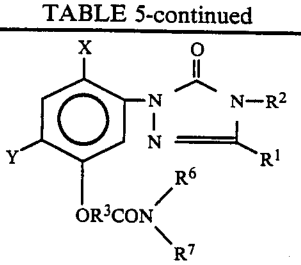

| Cmpd. No. | X | Y | $R^1$ | $R^2$ | $R^3$ | $R^6$ | $R^7$ |
|---|---|---|---|---|---|---|---|
| C34 | F | Cl | $CH_3$ | $CHF_2$ | $CH_2$ | 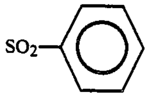 | H |
| C35 | F | $CH_3$ | $CH_3$ | $CHF_2$ | $CH(CH_3)$ | $NHCH_3$ | H |
| C36 | F | $CH_3$ | $CH_3$ | $CHF_2$ | $CH(CH_3)$ | $SO_2CH_3$ | H |
| C37 | F | $CH_3$ | $CH_3$ | $CHF_2$ | $CH_2$ | $SO_2CH_3$ | H |
| C38 | F | Cl | $CH_3$ | $CHF_2$ | $CH(CH_3)$ | $-CH_2CH_2CH_2CH_2-$ | |
| C39 | F | Cl | $CH_3$ | $CHF_2$ | $CH(CH_3)$ | $-CH_2CH_2OCH_2CH_2-$ | |
| C40 | F | Cl | $CH_3$ | $CHF_2$ | $CH(CH_3)$ | $SO_2N(CH_3)_2$ | H |
| C41 | F | Cl | $CH_3$ | $CHF_2$ | $CH(CH_3)$ | $SO_2NHCH(CH_3)_2$ | H |
| C42 | F | Cl | $CH_3$ | $CHF_2$ | $CH(CH_3)$ | 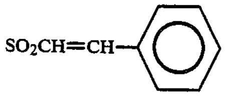 | H |
| C43 | F | Cl | $CHF_2$ | $CH_3$ | $CH(CH_3)$ | 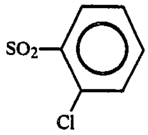 | H |
| C44 | F | Cl | $CF_2Cl$ | $CH_3$ | $CH(CH_3)$ | H | $CH_3$ |
| C45 | F | $CH_3$ | $CHF_2$ | $CH_3$ | $CH(CH_3)$ | $SO_2CH_3$ | H |
| C46 | F | $CH_2SCH_3$ | $CHF_2$ | $CH_3$ | $CH_2$ | $CH_3$ | $CH_3$ |
| C47 | F | Cl | $CHF_2$ | $CH_2CN$ | $CH(CH_3)$ | H | H |
| C48 | F | Cl | $CHF_2$ | $CH_2SCN$ | $CH(CH_3)$ | H | $CH(CH_3)_2$ |
| C49 | F | Cl | $CF_3$ | $CH_2OCH_3$ | $CH_2$ | $CH_2CH=CH_2$ | H |
| C50 | F | Cl | $CF_3$ | $CH_2CH=CH_2$ | $CH(CH_3)$ | 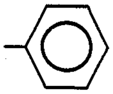 | H |
| C51 | F | Cl | $CHF_2$ | $CHF_2$ | $CH(CH_3)$ | H | H |
| C52 | Cl | Cl | $CHF_2$ | $CH_3$ | $CH_2$ | 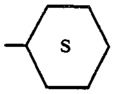 | H |
| C53 | F | Cl | $CH_3$ | $CHF_2$ | $CH(CH_3)$ | $CH_2CH_2OCH_3$ | H |
| C54 | F | Cl | $CH_3$ | $CHF_2$ | $CH(CH_3)$ | 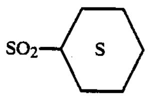 | H |
| C55 | F | Cl | $CH_3$ | $CHF_2$ | $CH_2$ | $SO_2CH_2CH=CH_2$ | H |
| C56 | F | Cl | $CH_3$ | $CHF_2$ | $CH_2$ | $SO_2CH_2CH=CH_2$ | Na |
| C57 | F | Cl | $CH_3$ | $CHF_2$ | $CH(CH_3)$ | $-CH_2CH_2CH_2CH_2CH_2-$ | |
| C58 | F | Cl | $CH_3$ | $CHF_2$ | $CH(CH_3)$ | 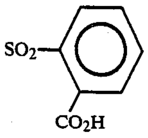 | H |

TABLE 5-continued

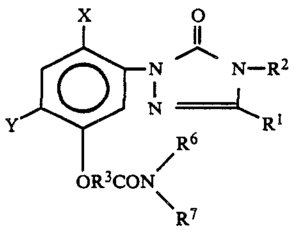

| Cmpd. No. | X | Y | $R^1$ | $R^2$ | $R^3$ | $R^6$ | $R^7$ |
|---|---|---|---|---|---|---|---|
| C59 | F | Cl | $CH_3$ | $CHF_2$ | $CH(CH_3)$ | 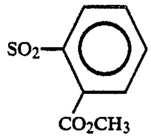 | H |
| C60 | Cl | Cl | $CHF_2$ | $CH_3$ | $CH(CH_3)$ | $SO_2N(CH_3)_2$ | H |
| C61 | F | Cl | $CHF_2$ | $CHF_2$ | $CH(CH_3)$ | H | H |
| C62 | F | Cl | $CH_3$ | $CHF_2$ | $CH(CH_3)$ | 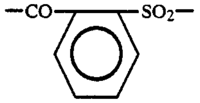 | |
| C63 | $CF_3$ | Cl | $CH_3$ | $CHF_2$ | $CH(CH_3)$ | H | H |
| C64 | F | Cl | $CH_2CN$ | $CHF_2$ | $CH(CH_3)$ | H | H |
| C65 | F | Cl | $CH_2SCH_3$ | $CHF_2$ | $CH_2$ | $CH_3$ | H |
| C66 | F | Cl | $SCH_3$ | $CHF_2$ | $CH(CH_3)$ | $CH_3$ | $CH_3$ |
| C67 | F | Cl | Cl | $CHF_2$ | $CH(CH_3)$ | H | H |
| C68 | F | 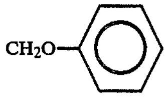 | $CH_3$ | $CHF_2$ | $CH(CH_3)$ | H | H |
| C69 | F | Cl | $CH_3$ | $CHF_2$ | $CH_2$ | 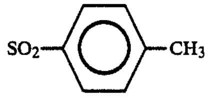 | H |
| C70 | F | Cl | $CH_3$ | $CHF_2$ | $CH_2$ | 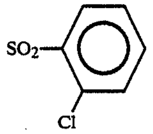 | H |
| C71 | F | Cl | $CH_3$ | $CHF_2$ | $CH(CH_3)$ | 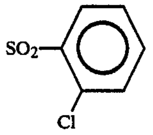 | Na |
| C72 | F | Cl | $CH_3$ | $CHF_2$ | $CH(CH_3)$ | 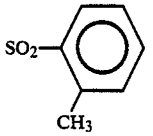 | H |
| C73 | F | Cl | $CH_3$ | $CHF_2$ | $CH(CH_3)$ | 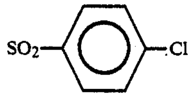 | H |

TABLE 5-continued
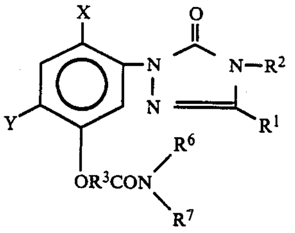
| Cmpd. No. | X | Y | $R^1$ | $R^2$ | $R^3$ | $R^6$ | $R^7$ |
|---|---|---|---|---|---|---|---|
| C74 | F | Cl | $CH_3$ | $CHF_2$ | $CH(CH_3)$ | 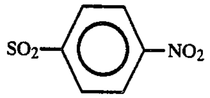 | H |
| C75 | F | Cl | $CH_3$ | $CHF_2$ | $CH(CH_3)$ | 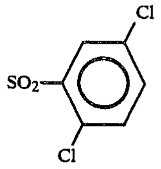 | H |
| C76 | Cl | Cl | $CH_3$ | $CHF_2$ | $CH(CH_3)$ | 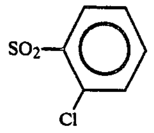 | H |
| C77 | F | Cl | $CH_3$ | $CHF_2$ | $CH(CH_3)$ | 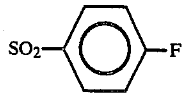 | H |
| C78 | F | Cl | $CH_3$ | $CHF_2$ | $CH(CH_3)$ | 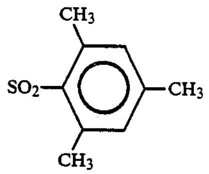 | H |
| C79 | F | Cl | $CH_3$ | $CHF_2$ | $CH(CH_3)$ | 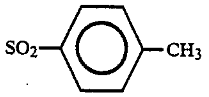 | $CH_3$ |
| C80 | F | Cl | $CH_3$ | $CHF_2$ | $CH(CH_3)$ | 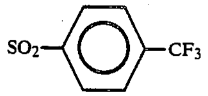 | H |
| C81 | F | Cl | $CH_3$ | $CHF_2$ | $CH(CH_3)$ | 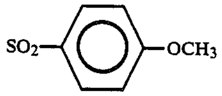 | H |
| C82 | F | Cl | $CH_3$ | $CHF_2$ | $CH(CH_3)$ | 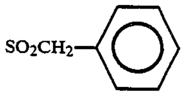 | H |
| C83 | F | Cl | $CH_3$ | $CHF_2$ | $CH(CH_3)$ | 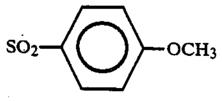 | Na |

TABLE 5-continued
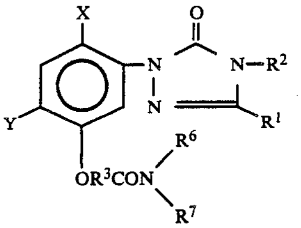
| Cmpd. No. | X | Y | $R^1$ | $R^2$ | $R^3$ | $R^6$ | $R^7$ |
|---|---|---|---|---|---|---|---|
| C84 | F | Cl | $CH_3$ | $CHF_2$ | $CH(CH_3)$ | 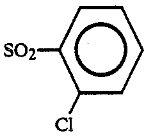 | $CH_3$ |
| C85 | F | Cl | $CH_3$ | $CHF_2$ | $CH(CH_3)$ | 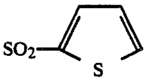 | H |
| C86 | F | Cl. | $CH_3$ | $CHF_2$ | $CH(CH_3)$ | $-CHCH_2CH_2CH_2-$ with $CO_2CH_3$ on the CH | |
| C87 | F | Cl | $CH_3$ | $CHF_2$ | $CH(CH_3)$ | 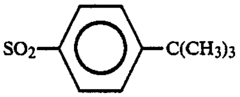 | H |
| C88 | F | Cl | $CH_3$ | $CH_3$ | $CH(CH_3)$ | 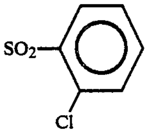 | H |
| C89 | F | Cl | $CH_3$ | $CHF_2$ | $CH(CH_3)$ | $-CHCH_2CH_2CH_2-$ with $CO_2H$ on the CH | |
| C90 | F | Cl | $CH_3$ | $CHF_2$ | $CH(CH_3)$ | 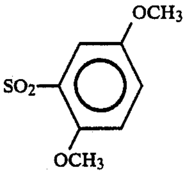 | H |
| C91 | F | Cl | $CH_3$ | $CHF_2$ | $CH(CH_3)$ | 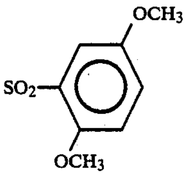 | Na |
| C92 | F | Cl | $CH_3$ | $CHF_2$ | $CH(CH_3)$ | 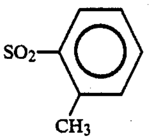 | Na |
| C93 | F | Cl | $CH_3$ | $CHF_2$ | $CH(CH_3)$ | 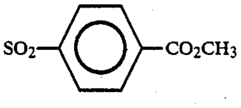 | H |

TABLE 5-continued

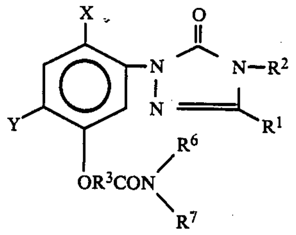

| Cmpd. No. | X | Y | $R^1$ | $R^2$ | $R^3$ | $R^6$ | $R^7$ |
|---|---|---|---|---|---|---|---|
| C94 | F | Cl | $CH_3$ | $CHF_2$ | $CH(CH_3)$ | 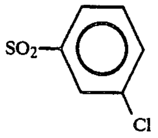 | H |
| C95 | F | Cl | $CH_3$ | $CHF_2$ | $CH(CH_3)$ | 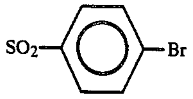 | H |
| C96 | F | Br | $CH_3$ | $CHF_2$ | $CH(CH_3)$ | $-CH_2CH_2CH_2CH_2-$ | |
| C97 | F | Cl | $CH_3$ | $CHF_2$ | $CH(CH_3)$ | $-CHCH_2CH_2CH_2-$<br>$CO_2CH_2CH_3$ | |
| C98 | F | Cl | $CH_3$ | $CHF_2$ | $CH(CH_3)$ | 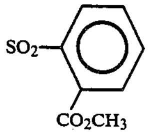 | Na |
| C99 | F | Cl | $CH_3$ | $CHF_2$ | $CH(CH_3)$ | 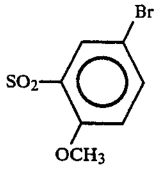 | H |
| C100 | F | Cl | $CH_3$ | $CHF_2$ | $CH(CH_3)$ | 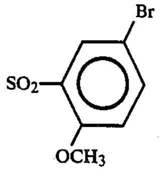 | Na |
| C101 | F | Cl | $CH_3$ | $CHF_2$ | $CH(CH_3)$ | 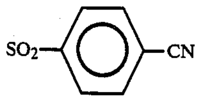 | H |
| C102 | F | Cl | $CH_3$ | $CHF_2$ | $CH(CH_3)$ | $-CHCH_2SCH_2-$<br>$CO_2CH_3$ | |
| C103 | F | Cl | $CH_3$ | $CHF_2$ | $CH(CH_3)$ | $-CHCH_2SO_2CH_2-$<br>$CO_2CH_3$ | |
| C104 | F | Cl | $CH_3$ | $CHF_2$ | $CH(CH_3)$ | $-CHCH_2CH_2CH_2CH_2-$<br>$CO_2CH_2CH_3$ | |

TABLE 5-continued
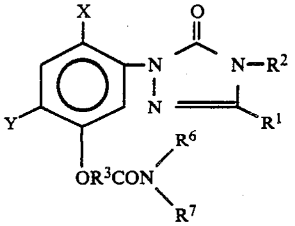
| Cmpd. No. | X | Y | $R^1$ | $R^2$ | $R^3$ | $R^6$ | $R^7$ |
|---|---|---|---|---|---|---|---|
| C105 | F | Cl | $CH_3$ | $CHF_2$ | $CH(CH_3)$ | 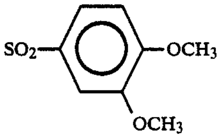 | H |
| C106 | F | Cl | $CH_3$ | $CHF_2$ | $CH(CH_3)$ | 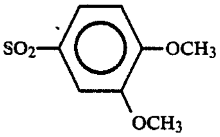 | Na |
| C107 | F | Cl | $CH_3$ | $CHF_2$ | $CH(CH_3)$ | 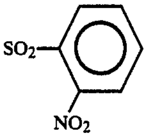 | H |
| C108 | F | Cl | $CH_3$ | $CHF_2$ | $CH(CH_3)$ | 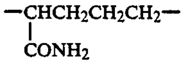 | |
| C109 | F | Cl | $CH_3$ | $CHF_2$ | $CH(CH_3)$ | 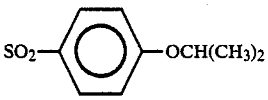 | H |
| C110 | F | Cl | $CH_3$ | $CHF_2$ | $CH(CH_3)$ | 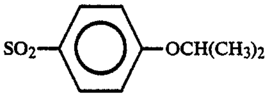 | Na |
| C111 | F | Cl | $CH_3$ | $CHF_2$ | $CH(CH_3)$ | 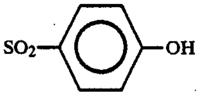 | H |
| C112 | F | Cl | $CH_3$ | $CHF_2$ | $CH_2$ | 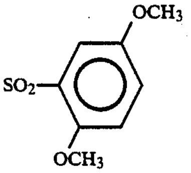 | H |
| C113 | F | Cl | $CH_3$ | $CHF_2$ | $CH(CH_3)$ | 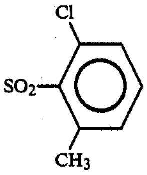 | H |

TABLE 5-continued
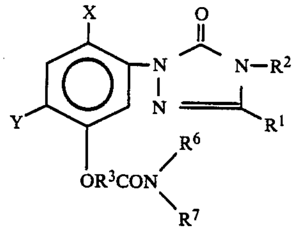
| Cmpd. No. | X | Y | $R^1$ | $R^2$ | $R^3$ | $R^6$ | $R^7$ |
|---|---|---|---|---|---|---|---|
| C114 | F | Cl | $CH_3$ | $CHF_2$ | $CH(CH_3)$ | 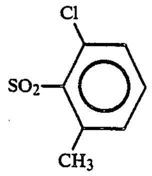 | Na |
| C115 | F | Br | $CH_3$ | $CHF_2$ | $CH(CH_3)$ | 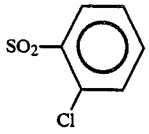 | H |
| C116 | F | Cl | $CH_3$ | $CHF_2$ | $CH_2$ | 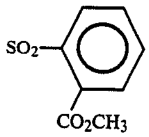 | H |
| C117 | F | Cl | $CH_3$ | $CHF_2$ | $CH(CH_3)$ | 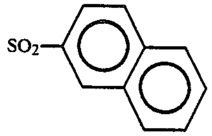 | H |
| C118 | Cl | Cl | $CClF_2$ | $CH_3$ | $CH(CH_3)$ | 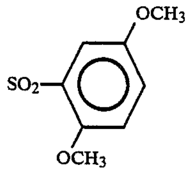 | H |
| C119 | F | Cl | $CH_3$ | $CHF_2$ | $CH_2$ | 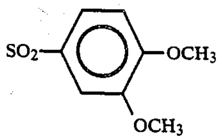 | H |
| C120 | F | Cl | $CH_3$ | $CHF_2$ | $CH_2$ | 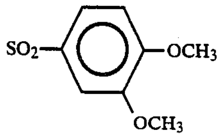 | H |
| C121 | F | Cl | $CH_3$ | $CHF_2$ | $CH_2$ | 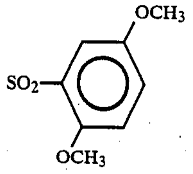 | Na |

TABLE 5-continued
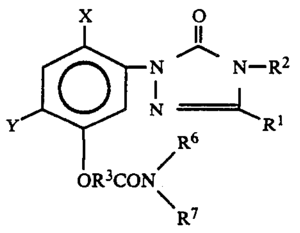
| Cmpd. No. | X | Y | $R^1$ | $R^2$ | $R^3$ | $R^6$ | $R^7$ |
|---|---|---|---|---|---|---|---|
| C122 | Cl | Cl | $CHF_2$ | $CH_3$ | $CH(CH_3)$ | 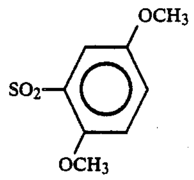 | H |
| C123 | F | Br | $CH_3$ | $CHF_2$ | $CH(CH_3)$ | 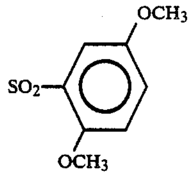 | H |
| C124 | F | Cl | $CH_3$ | $CHF_2$ | $CH(CH_3)$ | 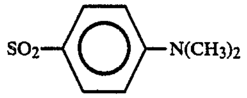 | H |
| C125 | F | Cl | $CH_3$ | $CHF_2$ | $CH(CH_3)$ | 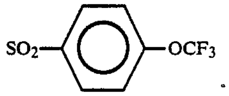 | H |
| C126 | F | Cl | $CH_3$ | $CHF_2$ | $CH(CH_3)$ | 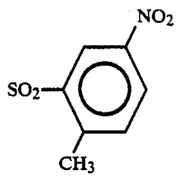 | H |
| C127 | F | Cl | $CH_3$ | $CHF_2$ | $CH(CH_3)$ | 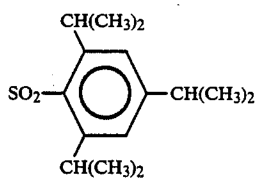 | H |
| C128 | F | Cl | $CH_3$ | $CHF_2$ | $CH(CH_3)$ | 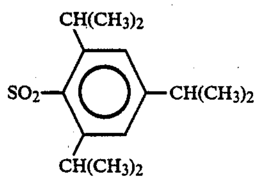 | H |
| C129 | F | Cl | $CH_3$ | $CHF_2$ | $CH_2$ | 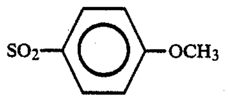 | H |

TABLE 5-continued
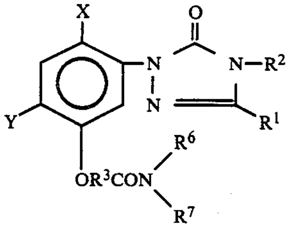
| Cmpd. No. | X | Y | $R^1$ | $R^2$ | $R^3$ | $R^6$ | $R^7$ |
|---|---|---|---|---|---|---|---|
| C130 | F | Cl | $CH_3$ | $CHF_2$ | $CH_2$ | 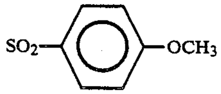 | Na |
| C131 | F | Cl | $CH_3$ | $CHF_2$ | $CH(CH_3)$ | 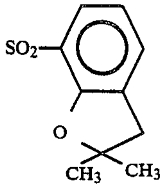 | H |
| C132 | F | Cl | $CH_3$ | $CHF_2$ | $CH(CH_3)$ | 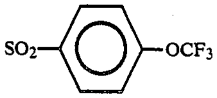 | Na |
| C133 | F | Br | $CH_3$ | $CHF_2$ | $CH(CH_3)$ | 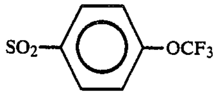 | H |
| C134 | F | Cl | $CH_3$ | $CHF_2$ | $CH(CH_3)$ | 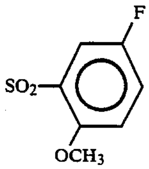 | H |
| C135 | F | Cl | $CH_3$ | $CHF_2$ | $CH(CH_3)$ | 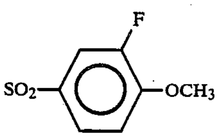 | H |
| C136 | F | Cl | $CH_3$ | $CHF_2$ | $CH(CH_3)$ | 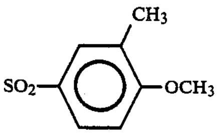 | H |
| C137 | F | Cl | $CH_3$ | $CHF_2$ | $CH(CH_3)$ | 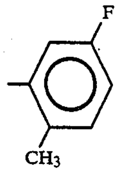 | H |

TABLE 5-continued
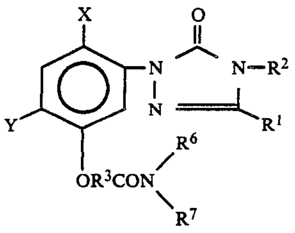
| Cmpd. No. | X | Y | $R^1$ | $R^2$ | $R^3$ | $R^6$ | $R^7$ |
|---|---|---|---|---|---|---|---|
| C138 | F | Cl | $CH_3$ | $CHF_2$ | $CH(CH_3)$ | 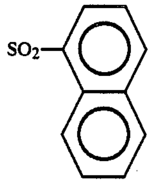 | H |
| C139 | F | Cl | $CH_3$ | $CHF_2$ | $CH(CH_3)$ | 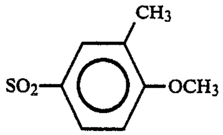 | Na |
| C140 | F | Cl | $CH_3$ | $CHF_2$ | $CH(CH_3)$ | 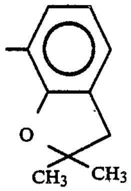 | H |
| C141 | F | Br | $CH_3$ | $CHF_2$ | $CH(CH_3)$ | 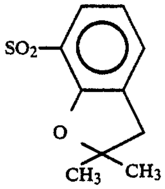 | H |
| C142 | F | Cl | $CH_3$ | $CHF_2$ | $CH(CH_3)$ | 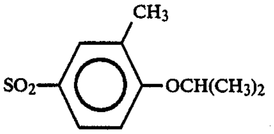 | H |
| C143 | F | Cl | $CH_3$ | $CHF_2$ | $CH(CH_3)$ | 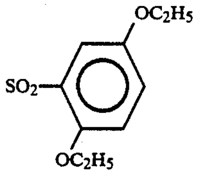 | H |
| C144 | F | Br | $CH_3$ | $CHF_2$ | $CH(CH_3)$ | 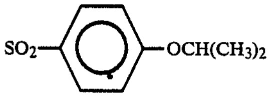 | H |
| C145 | F | Cl | $CH_3$ | $CHF_2$ | $CH(CH_3)$ | 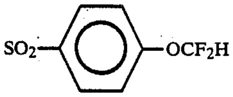 | H |

TABLE 5-continued
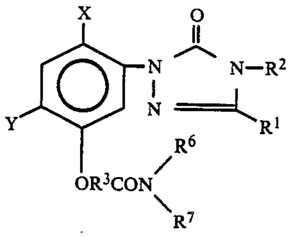
| Cmpd. No. | X | Y | $R^1$ | $R^2$ | $R^3$ | $R^6$ | $R^7$ |
|---|---|---|---|---|---|---|---|
| C146 | F | Cl | $CH_3$ | $CHF_2$ | $CH(CH_3)$ | 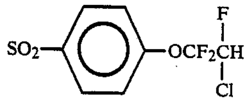 | H |
| C147 | F | Cl | $CH_3$ | $CHF_2$ | $CH(CH_3)$ | 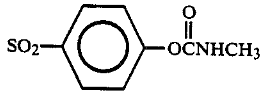 | H |
| C148 | F | Br | $CH_3$ | $CHF_2$ | $CH(CH_3)$ | 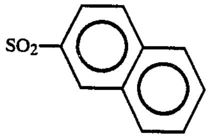 | H |
| C149 | F | Cl | $CH_3$ | $CHF_2$ | $CH(CH_3)$ | 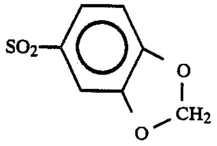 | H |
| C150 | F | Cl | $CH_3$ | $CHF_2$ | $CH(CH_3)$ | 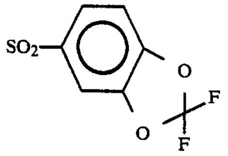 | H |
| C151 | F | Br | $CH_3$ | $CHF_2$ | $CH(CH_3)$ | 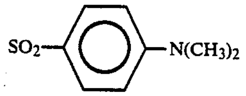 | H |
| C152 | F | Cl | $CH_3$ | $CHF_2$ | $CH(CH_3)$ | 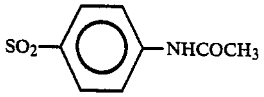 | H |
| C153 | F | Cl | $CH_3$ | $CHF_2$ | $CH(CH_3)$ | 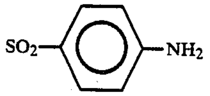 | H |
| C154 | F | Cl | $CH_3$ | $CHF_2$ | $CH(CH_3)$ | 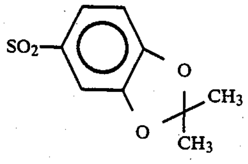 | H |

TABLE 5-continued
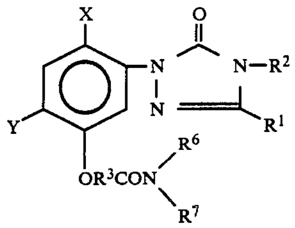
| Cmpd. No. | X | Y | $R^1$ | $R^2$ | $R^3$ | $R^6$ | $R^7$ |
|---|---|---|---|---|---|---|---|
| C155 | Cl | Cl | $CHF_2$ | $CH_3$ | $CH(CH_3)$ | 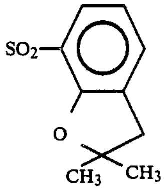 | H |
| C156 | Cl | Cl | $CH_3$ | $CHF_2$ | $CH(CH_3)$ | 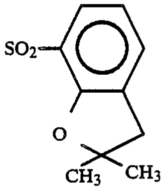 | H |
| C157 | F | Br | $CH_3$ | $CHF_2$ | $CH(CH_3)$ | $SO_2CH_3$ | H |
| C158 | F | Br | $CH_3$ | $CHF_2$ | $CH(CH_3)$ | $SO_2CF_3$ | H |
| C159 | F | Cl | $CH_3$ | $CHF_2$ | $CH(CH_3)$ | $SO_2NH_2$ | H |
| C160 | F | Br | $CH_3$ | $CHF_2$ | $CH(CH_3)$ | 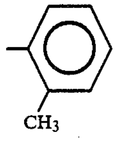 | H |
| C161 | F | Cl | $CH_3$ | $CHF_2$ | $CH(CH_3)$ | 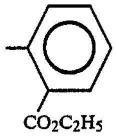 | H |
| C162 | F | Cl | $CH_3$ | $CHF_2$ | $CH(CH_3)$ | 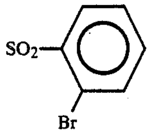 | H |
| C163 | F | Cl | $CH_3$ | $CHF_2$ | $CH(CH_3)$ | 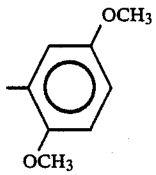 | H |
| C164 | F | Cl | $CH_3$ | $CHF_2$ | $CH(CH_3)$ | 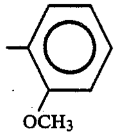 | H |

TABLE 5-continued
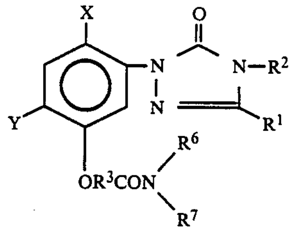
| Cmpd. No. | X | Y | $R^1$ | $R^2$ | $R^3$ | $R^6$ | $R^7$ |
|---|---|---|---|---|---|---|---|
| C165 | F | Cl | $CH_3$ | $CHF_2$ | $CH(CH_3)$ | 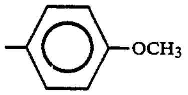 | H |
| C166 | F | Cl | $CH_3$ | $CHF_2$ | $CH(CH_3)$ | 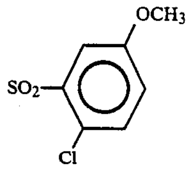 | H |
| C167 | F | Br | $CH_3$ | $CHF_2$ | $CH(CH_3)$ | 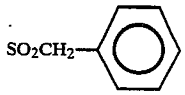 | H |
| C168 | F | Cl | $CH_3$ | $CHF_2$ | $CH(CH_3)$ | 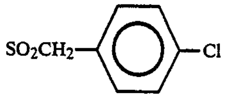 | H |
| C169 | F | Br | $CH_3$ | $CHF_2$ | $CH(CH_3)$ | 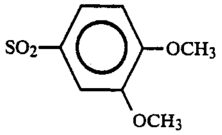 | H |
| C170 | F | Cl | $CHF_2$ | $CH_3$ | $CH(CH_3)$ | 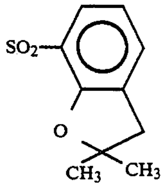 | H |
| C171 | F | Br | $CHF_2$ | $CH_3$ | $CH(CH_3)$ | 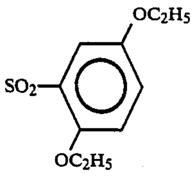 | H |
| C172 | F | Br | $CH_3$ | $CHF_2$ | $CH(CH_3)$ | 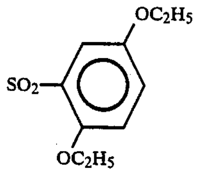 | H |
| C173 | F | Cl | $CHF_2$ | $CH_3$ | $CH(CH_3)$ | 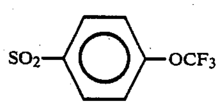 | H |

TABLE 5-continued
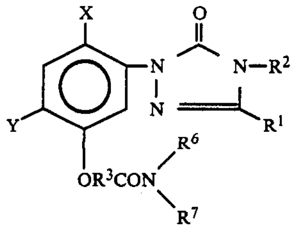
| Cmpd. No. | X | Y | $R^1$ | $R^2$ | $R^3$ | $R^6$ | $R^7$ |
|---|---|---|---|---|---|---|---|
| C174 | F | Cl | $CH_3$ | $CHF_2$ | $CH(CH_3)$ | 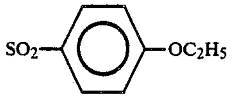 | H |
| C175 | F | Cl | $CH_3$ | $CHF_2$ | $CH(CH_3)$ | 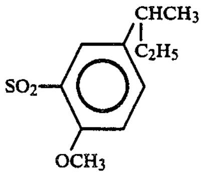 | H |
| C176 | F | Cl | $CH_3$ | $CHF_2$ | $CH(CH_3)$ | 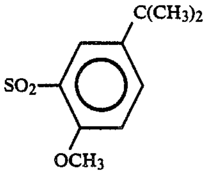 | H |
| C177 | F | Cl | $CH_3$ | $CHF_2$ | $CH(CH_3)$ | 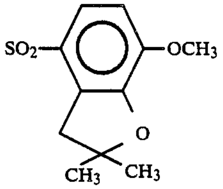 | H |
| C178 | F | Cl | $CH_3$ | $CHF_2$ | $CH(CH_3)$ | 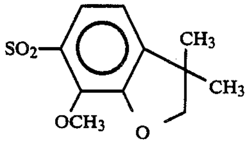 | H |
| C179 | F | Cl | $CH_3$ | $CHF_2$ | $CH(CH_3)$ | 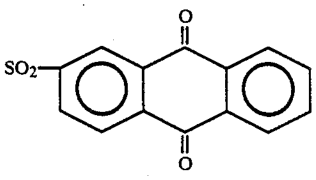 | H |
| C180 | F | Cl | $CH_3$ | $CHF_2$ | $CH(CH_3)$ | 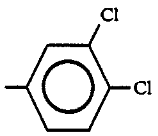 | H |
| C181 | F | Cl | $CH_3$ | $CHF_2$ | $CH(CH_3)$ | 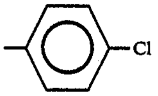 | H |

TABLE 5-continued

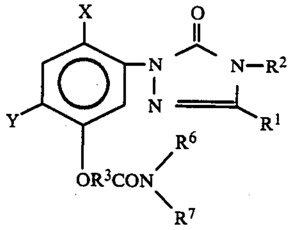

| Cmpd. No. | X | Y | $R^1$ | $R^2$ | $R^3$ | $R^6$ | $R^7$ |
|---|---|---|---|---|---|---|---|
| C182 | F | Cl | $CH_3$ | $CHF_2$ | $CH(CH_3)$ | 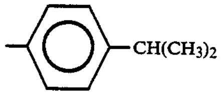 | H |
| C183 | F | Cl | $CH_3$ | $CHF_2$ | $CH(CH_3)$ | 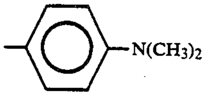 | H |
| C184 | F | Cl | $CH_3$ | $CHF_2$ | $CH(CH_3)$ | 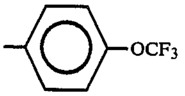 | H |
| C185 | F | Br | $CH_3$ | $CHF_2$ | $CH(CH_3)$ | H | H |
| C186 | F | Br | $CH_3$ | $CHF_2$ | $CH(CH_3)$ | $CH_3$ | H |
| C187 | F | Br | $CH_3$ | $CHF_2$ | $CH(CH_3)$ | $CH_3$ | $CH_3$ |
| C188 | F | Br | $CH_3$ | $CHF_2$ | $CH(CH_3)$ | $C_2H_5$ | H |
| C189 | F | Cl | $CHF_2$ | $CH_3$ | $CH(CH_3)$ | 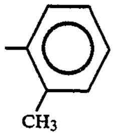 | H |
| C190 | F | Cl | $CHF_2$ | $CH_3$ | $CH(CH_3)$ | H | H |
| C191 | F | Cl | $CHF_2$ | $CH_3$ | $CH(CH_3)$ | $CH_3$ | H |
| C192 | F | Cl | $CHF_2$ | $CH_3$ | $CH(CH_3)$ | $CH_3$ | $CH_3$ |
| C193 | F | Br | $CHF_2$ | $CH_3$ | $CH(CH_3)$ | $CH_3$ | $CH_3$ |
| C194 | F | Br | $CHF_2$ | $CH_3$ | $CH(CH_3)$ | H | H |
| C195 | F | Br | $CHF_2$ | $CH_3$ | $CH(CH_3)$ | $CH_3$ | H |
| C196 | Br | Br | $CHF_2$ | $CH_3$ | $CH(CH_3)$ | $CH_3$ | $CH_3$ |
| C197 | Br | Br | $CHF_2$ | $CH_3$ | $CH(CH_3)$ | H | H |
| C198 | Br | Br | $CHF_2$ | $CH_3$ | $CH(CH_3)$ | $CH_3$ | H |
| C199 | Br | Br | $CH_3$ | $CHF_2$ | $CH(CH_3)$ | $CH_3$ | H |
| C200 | Br | Br | $CH_3$ | $CHF_2$ | $CH(CH_3)$ | H | H |
| C201 | F | Cl | $CH_3$ | $CHF_2$ | $CH(CH_3)$ | 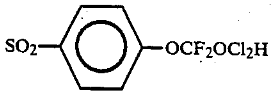 | H |
| C202 | F | Cl | $CH_3$ | $CHF_2$ | $CH(CH_3)$ | 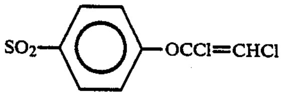 | H |
| C203 | F | Cl | $CH_3$ | $CHF_2$ | $CH(CH_3)$ | 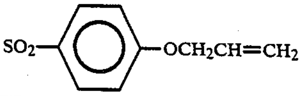 | H |

Other representative compounds are those which are identical with compounds C1–C95, C97–C114, C116–C122, C124–C132, C134–C140, C142–C143, C145–C147, C149–C150, C152–C156, C159, C161–C165, C168, C170, C173–C184, C186, C189–C192, and C196–C203 respectively, except that X is F and Y is Br. Still other representative compounds are those which are identical with Compounds C1–C203 respectively, except that X if F and Y is $CF_3$.

TABLE 6

| Cmpd. No. | Melting Point (°C.) | Identifying Properties: Empirical Formula | | Elemental Analysis C | H | N |
|---|---|---|---|---|---|---|
| 1 | 111.5-113.5 | $C_{13}H_{11}Cl_2F_2N_3O_4$ 4<br>NMRδ($CDCl_3$): 2.45(s,3H), 3.80(s,3H), 4.70(s,2H), 6.90(s,1H), 7.00(t,1H,J=58 Hz), 7.50(s,1H). | | | | |
| 2 | Oil | $C_{14}H_{13}Cl_2F_2N_3O_4$<br>NMRδ($CDCl_3$): 1.70(d,3H,J=7 Hz), 2.50 (s,3H), 3.80(s,3H), 4.80(q,1H,J=7 Hz). 7.00(s,1H), 7.10(t,1H,J=58 Hz), 7.60 (s,1H). | | | | |
| 3 | Oil | $C_{14}H_{13}ClF_3N_3O_4$<br>NMRδ($CDCl_3$): 1.70(d,3H,J=7 Hz), 2.50 (s,3H), 3.80(s,3H), 4.80(q,1H,J=7 Hz), 7.00(t,1H,J=58 Hz), 7.00-7.40(m,2H). | | | | |
| 4 | Oil | $C_{15}H_{16}ClF_2N_3O_4$<br>NMRδ($CDCl_3$): 1.65(d,3H,J=7 Hz), 2.30 (s,3H), 2.50(s,3H), 3.80(s,3H), 4.80 (q,1H,J=7 Hz), 6.80(s,1H), 7.10(t,1H,J=58 Hz), 7.40(s,1H). | | | | |
| 5 | Oil | $C_{15}H_{15}Cl_2F_2N_3O_4$<br>NMRδ($CDCl_3$): 1.20(t,3H,J=7 Hz), 1.70 (d,3H,J=7 Hz), 2.50(s,3H), 4.20(q,2H,J=7 Hz), 4.70(q.1H,J=7 Hz), 6.95(s,1H), 7.05(t,1H,J=58 Hz), 7.60(s,1H), | | | | |
| 6 | Oil | $C_{15}H_{15}ClF_3N_3O_4$<br>NMRδ($CDCl_3$): 1.20(t,3H,J=7 Hz), 1.70 (d,3H,J=7 Hz), 2.50(s,3H), 4.20(q,2H,J=7 Hz, 4.70(q,1H,J=7 Hz), 7.00(t,H,J=58 Hz), 7.00-7.40(m,2H). | | | | |
| 7 | Oil | $C_{16}H_{18}ClF_2N_3O_4$<br>NMRδ($CDCl_3$): 1.20(t,3H,J=7 Hz), 1.60 (d,3H,J=7 Hz), 2.30(s,3H), 2.50(s,3H), 4.25(q,2H,J=7 Hz), 4.70(q,1H,J=7 Hz), 6.80(s,1H), 7.05(t,1H,J=58 Hz), 7.30 (s,1H). | | | | |
| 8 | Oil | $C_{15}H_{15}Br_2F_2N_3O_4$<br>NMRδ($CDCl_3$): 1.20(t,3H,J=7 Hz), 1.70 (d,3H,J=7 Hz), 2.45(s,3H), 4.15(q,2H,J=7 Hz), 4.80(q,1H,J=7 Hz), 6.95(s,1H), 7.10(t,1H,J=58 Hz), 7.95(s,1H). | | | | |
| 9 | 83-88 | $C_{16}H_{17}Cl_2F_2N_3O_4$<br>NMRδ($CDCl_3$): 0.90(t,3H,J=7 Hz), 1.20-1.90(m,5H), 2.50(s,3H), 4.20(t,2H,J=7 Hz), 4.80(q,1H,J=7 Hz), 7.00(s,1H), 7.10(t,1H,J=58 Hz), 7.60(s,1H). | | | | |
| 10 | Oil | $C_{16}H_{17}Cl_2F_2N_3O_4$<br>NMRδ($CDCl_3$): 1.20(m,6H), 1.70(d,3H, J=7 Hz), 2.50(s,3H), 4.60-5.30(m,2H), 6.90(s,1H), 7.10(t,1H,J=58 Hz), 7.60 (s,1H). | | | | |
| 11 | Oil | $C_{17}H_{19}Cl_2F_2N_3O_4$<br>NMRδ($CDCl_3$): 0.70-1.70(m,7H), 1.60 (d,3H,J=7 Hz), 2.45 (s,3H), 4.15(t,2H, J=7 Hz), 4.70(q,1H,J=7 Hz), 6.95(s,1H), 7.05(t,1H,J=58 Hz), 7.60(s,1H). | | | | |
| 12 | Oil | $C_{17}H_{19}Cl_2F_2N_3O_4$<br>NMRδ($CDCl_3$): 0.70-1.80(m,11H), 2.50 (s,3H), 4.40-5.30(m,2H), 7.00(s,1H), 7.10(t,1H,J=58 Hz), 7.60(s,1H). | | | | |
| 13 | Oil | $C_{15}H_{16}Cl_2FN_3O_4$ | C | 45.94 | 4.11 | 10.71 |
| | | | F | 46.62 | 4.16 | 12.10 |
| | | NMRδ($CDCl_3$): 1.20(t,3H,J=7 Hz), 1.60 (d,3H,J=7 Hz), 2.35(s,3H), 4.20(q,2H,J=7 Hz), 4.75(q,1H,J=7 Hz), 5.75(d,2H,J=53 Hz), 7.00(s,1H), 7.60(s,1H). | | | | |
| 14 | 110-111 | $C_{13}H_{11}ClF_3N_3O_4$ | | | | |
| 15 | Oil | $C_{16}H_{17}ClF_2N_3O_4$ | | | | |
| 16 | Oil | $C_{16}H_{17}ClF_3N_3O_4$ | | | | |
| 17 | 118-119 | $C_{14}H_{13}Cl_2F_2N_3O_4$ | C | 42.44 | 3.31 | 10.61 |
| | | | F | 42.60 | 3.58 | 10.53 |
| 18 | Oil | $C_{16}H_{17}Cl_2F_2N_3O_4$ | C | 45.30 | 4.04 | 9.90 |
| | | | F | 44.95 | 3.79 | 9.70 |
| 19 | Oil | $C_{17}H_{19}ClF_3N_3O_4$ | | | | |
| 20 | Oil | $C_{16}H_{17}ClF_3N_3O_4$ | C | 47.13 | 4.20 | 10.30 |
| | | | F | 47.39 | 4.38 | 10.35 |
| 21 | Oil | $C_{16}H_{17}Cl_2F_2N_3O_4$ | | | | |
| 22 | 137-138 | $C_{16}H_{17}ClF_3N_3O_4$ | C | 47.13 | 4.20 | 10.30 |
| | | | F | 47.23 | 3.94 | 9.96 |
| 52 | Oil | $C_{17}H_{19}ClF_3N_3O_4$ | | | | |

TABLE 6-continued

| Cmpd. No. | Melting Point (°C.) | Identifying Properties: Empirical Formula | Elemental Analysis | C | H | N |
|---|---|---|---|---|---|---|
| A1 | 55–56 | $C_{13}H_{11}Cl_2F_2N_3O_4$ NMRδ($CDCl_3$): 1.70(d,3H,J=7 Hz), 2.50(s,3H), 4.80(q,1H,J=7 Hz), 7.00(s,1H), 7.10(t,H,J=58 Hz), 7.48(s,1H), 7.50(s,1H). | | | | |
| A2 | 50–55 | $C_{13}H_{11}ClF_3N_3O_4$ NMRδ($CDCl_3$): 1.70(m,3H), 4.80(m,1H), 2.40 (s,3H), 7.10–7.50(m,3H), 8.00(bs,1H) | | | | |
| A3 | 56–60 | $C_{14}H_{14}ClF_2N_3O_4$ NMRδ($CDCl_3$): 1.60(d,3H,J=7 Hz), 2.30(s,3H), 2.50(s,3H), 4.70(q,1H,J=7 Hz), 6.80(2,1H), 7.00(t,1H,J=58 Hz), 7.30(s,1H), 8.30(s,1H). | | | | |
| A4 | Solid | $C_{13}H_{10}ClF_3N_3NaO_4$ | | | | |
| A5 | 130–132 | $C_{12}H_9ClF_3N_3O_4H_2O$ | C | 38.99 | 3.00 | 11.37 |
| | | | F | 38.95 | 2.91 | 11.23 |
| A6 | 70–75 | $C_{16}H_{20}ClF_3N_4O_4$ | | | | |
| B1 | Oil | $C_{16}H_{16}Cl_2F_2N_4O_6$ NMRδ($CDCl_3$): 1.40–1.80(m,6H), 2.50(s,3H), 4.40–5.00(m,4H), 7.00(s,1H), 7.10(t,1H,J=58 Hz), 7.60(s,1H). | | | | |
| B2 | Oil | $C_{16}H_{15}Cl_2F_2N_3O_4$ | C | 45.52 | 3.58 | 9.95 |
| | | | F | 45.24 | 3.46 | 9.87 |
| | | NMRδ($CDCl_3$): 1.70(d,3H,J=7 Hz), 2.50(s,3H), 4.60–5.00(m,3H), 5.10–5.40(m,2H), 5.50–6.20 (m,1H), 7.00(s,1H), 7.10(t,1H,J=58 Hz), 7.60 (s,1H). | | | | |
| B3 | Oil | $C_{16}H_{13}Cl_2F_2N_3O_4$ NMRδ($CDCl_3$): 1.70(d,3H,J=7 Hz), 2.50(bs,4H), 4.60–4.90(m,3H), 6.95(s,1H), 7.05(t,1H,J=58 Hz), 7.60(s,1H). | | | | |
| B4 | Oil | $C_{16}H_{13}ClF_3N_3O_4$ | C | 47.60 | 3.24 | 10.41 |
| | | | F | 47.88 | 3.31 | 9.68 |
| | — | NMRδ($CDCl_3$): 1.65(d,3H,J=7 Hz), 2.45(m,4H), 4.70(m,3H), 7.05(t,1H,J=58 Hz), 7.10–7.40(m,2H) | | | | |
| B5 | Solid | $C_{16}H_{17}Cl_2F_2N_3O_5$ | | | | |
| B6 | Oil | $C_{17}H_{15}ClF_3N_3O_4$ | C | 48.87 | 3.62 | 10.06 |
| | | | F | 46.60 | 3.19 | 10.01 |
| B7 | Oil | $C_{18}H_{17}ClF_3N_3O_4$ | C | 50.07 | 3.97 | 9.73 |
| | | | F | 49.68 | 3.75 | 9.40 |
| B8 | Oil | $C_{18}H_{19}ClF_3N_3O_5$ | C | 48.06 | 4.26 | 9.34 |
| | | | F | 48.31 | 3.77 | 9.00 |
| B9 | Oil | $C_{16}H_{15}ClF_3N_3O_6$ | | | | |
| B10 | Oil | $C_{18}H_{17}ClF_7N_3O_4$ | | | | |
| B11 | Oil | $C_{15}H_{12}ClF_3N_4O_4$ | | | | |
| B12 | Oil | $C_{18}H_{15}ClF_3N_3O_5$ | | | | |
| B13 | Oil | $C_{17}H_{20}ClF_3N_4O_4$ | | | | |
| B14 | Oil | $C_{17}H_{17}ClF_3N_3O_5$ | | | | |
| B15 | Oil | $C_{19}H_{15}ClF_3N_3O_4$ | C | 51.66 | 3.42 | 9.51 |
| | | | F | 52.15 | 3.43 | 9.49 |
| B16 | Solid | $C_{17}H_{15}ClF_3N_3O_6$ | C | 45.40 | 3.36 | 9.34 |
| | | | F | 45.00 | 3.25 | 8.90 |
| B17 | Oil | $C_{15}H_{15}ClF_3N_3O_3S$ | | | | |
| B18 | Oil | $C_{17}H_{17}ClF_3N_3O_5S$ | C | 43.64 | 3.66 | 8.98 |
| | | | F | 43.50 | 3.73 | 7.99 |
| B19 | Oil | $C_{14}H_{12}Cl_2F_3N_3O_4$ NMRδ($CDCl_3$): 1.40(t,3H,J=7 Hz), 2.50(s,3H), 4.45(q,2H,J=7 Hz), 5.95(d,1H,J=58 Hz), 7.40(s,1H), 7.50(t,1H,J=58 Hz), 7.65(s,1H). | | | | |
| B21 | 131–136 | $C_{19}H_{22}ClF_3N_4O_5$ | | | | |
| B22 | Oil | $C_{15}H_{15}ClF_3N_3O_5$ | | | | |
| B23 | Oil | $C_{15}H_{15}ClF_3N_3O_4S$ | | | | |
| B25 | Solid | $C_{15}H_{15}ClF_3N_3O_6S$ | C | 39.36 | 3.30 | 9.18 |
| | | | F | 39.25 | 3.00 | 9.22 |
| B30 | Oil | $C_{15}H_{12}ClF_6N_3O_4$ | | | | |
| B31 | Oil | $C_{17}H_{16}ClF_3N_4O_4$ | | | | |
| B32 | Oil | $C_{20}H_{17}ClF_3N_3O_4$ | | | | |
| B33 | Oil | $C_{16}H_{17}ClF_3N_3O_3S$ | | | | |
| B50 | Oil | $C_{20}H_{17}ClF_3N_3O_4S$ | | | | |
| B57 | Oil | $C_{17}H_{17}ClF_3N_3O_6$ | C | 45.19 | 3.79 | 9.30 |
| | | | F | 45.68 | 3.77 | 8.22 |
| C1 | 209–210 | $C_{12}H_{10}Cl_2F_2N_4O_3$ NMRδ($CDCl_3$/DMSO $d_6$): 2.20(s,3H), 4.60(s,2H), 7.30(bs,3H), 7.40(5,1H,J=58 Hz), 7.65(s,1H). | | | | |
| C2 | Oil | $C_{14}H_{14}ClF_3N_4O_3$ NMRδ($CDCl_3$): 1.60(d,3H,J=7 Hz), 2.50(s,3H), 2.90(d,3H,J=7 Hz), 4.75(q,1H,J=7 Hz), 6.80(bs,1H), 7.10(t,1H,J=58 Hz), 7.20–7.45(m,2H). | | | | |
| C3 | 185–188 | $C_{14}H_{14}Cl_2F_2N_4O_5S$ | C | 36.61 | 3.07 | 12.20 |
| | | | F | 36.79 | 3.01 | 12.41 |

TABLE 6-continued

| Cmpd. No. | Melting Point (°C.) | Identifying Properties Empirical Formula | Elemental Analysis | C | H | N |
|---|---|---|---|---|---|---|
| | | NMRδ($CDCl_3$): 1.70(d,3H,J=7 Hz), 2.50(s,3H), 3.40(s,3H), 4.80(q,1H,J=7 Hz), 7.10(s,1H), 7.10(t,1H,J=58 Hz), 7.70(s,1H). | | | | |
| C4 | Oil | $C_{14}H_{11}Cl_2F_5N_4O_5S$ | C | 32.76 | 2.16 | 10.92 |
| | | | F | 32.80 | 2.05 | 8.77 |
| | | NMRδ($CDCl_3$): 1.70(d,3H,J=7 Hz), 2.50(s,3H), 4.90(q,1H,J=7 Hz), 7.10(s,1H), 7.10(t,1H,J=58 Hz), 7.60(s,1H), 8.50(bs,1H). | | | | |
| C5 | 132-135 | $C_{13}H_{12}Cl_2F_2N_4O_3$ | | | | |
| C6 | 142-144 | $C_{14}H_{14}Cl_2F_2N_4O_3$ | | | | |
| C7 | 173-175 | $C_{12}H_{10}ClF_3N_4O_3$ | | | | |
| C8 | 105-110 | $C_{16}H_{18}ClF_3N_4O_3$ | | | | |
| C9 | Oil | $C_{17}H_{20}ClF_3N_4O_3$ | | | | |
| C10 | Solid | $C_{20}H_{18}ClF_3N_4O_5S$ | C | 46.29 | 3.50 | 10.80 |
| | | | F | 46.77 | 4.12 | 11.03 |
| C11 | Oil | $C_{15}H_{16}ClF_3N_4O_4$ | C | 44.07 | 3.94 | 13.71 |
| | | | F | 38.44 | 3.67 | 11.28 |
| C12 | Solid | $C_{16}H_{14}ClF_3N_4O_3$ | C | 47.71 | 3.50 | 13.91 |
| | | | F | 46.03 | 3.60 | 13.91 |
| C13 | 57 | $C_{19}H_{16}ClF_3N_4O_3$ | C | 51.77 | 3.66 | 12.71 |
| | | | F | 50.90 | 4.00 | 11.88 |
| C14 | Oil | $C_{15}H_{16}ClF_3N_4O_3$ | | | | |
| C15 | Solid | $C_{17}H_{20}ClF_3N_4O_3$ | | | | |
| C16 | Oil | $C_{15}H_{16}ClF_3N_4O_3$ | | | | |
| C17 | Solid | $C_{16}H_{16}ClF_3N_4O_5$ | | | | |
| C18 | 145-150 | $C_{14}H_{14}ClF_3N_4O_5S$ | | | | |
| C19 | Solid | $C_{14}H_{14}ClF_3N_4NaO_5S$ | | | | |
| C20 | Solid | $C_{20}H_{17}ClF_3N_4NaO_5S$ | | | | |
| C21 | Oil | $C_{18}H_{18}ClF_3N_4O_3$ | C | 50.18 | 4.21 | 13.00 |
| | | | F | 50.95 | 3.91 | 12.38 |
| C22 | Oil | $C_{17}H_{17}ClF_3N_5O_3$ | | | | |
| C23 | Oil | $C_{20}H_{18}ClF_3N_4O_3$ | | | | |
| C25 | Solid | $C_{19}H_{15}Cl_2F_3N_4O_5S$ | C | 42.31 | 2.80 | 10.39 |
| | | | F | 40.44 | 2.91 | 8.56 |
| C26 | 142-143 | $C_{13}H_{12}ClF_3N_4O_3$ | | | | |
| C32 | 127-134 | $C_{19}H_{16}ClF_3N_4O_5S$ | | | | |
| C38 | 47-54 | $C_{17}H_{18}ClF_3N_4O_3$ | C | 48.75 | 4.33 | 13.38 |
| | | | F | 47.06 | 3.73 | 12.36 |
| C42 | Oil | $C_{21}H_{18}ClF_3N_4O_5S$ | | | | |
| C43 | 162-166 | $C_{19}H_{15}Cl_2F_3N_4O_5S$ | | | | |
| C59 | 100-105 | $C_{21}H_{18}ClF_3N_4O_7S$ | C | 44.81 | 3.40 | 9.95 |
| | | | F | 42.20 | 2.81 | 9.61 |
| C69 | Solid | $C_{19}H_{16}ClF_3N_4O_5S$ | C | 45.20 | 3.19 | 11.10 |
| | | | F | 44.74 | 3.55 | 10.59 |
| C70 | 208-108.5 | $C_{18}H_{13}Cl_2F_3N_4O_5S$ | C | 41.16 | 2.49 | 10.67 |
| | | | F | 44.11 | 3.08 | 10.96 |
| C71 | Solid | $C_{19}H_{14}Cl_2F_3N_4O_5SNa$ | | | | |
| C72 | 135-140 | $C_{20}H_{18}ClF_3N_4O_5S$ | | | | |
| C73 | Solid | $C_{19}H_{15}Cl_2F_3N_4O_5S$ | | | | |
| C74 | 110 | $C_{19}H_{15}ClF_3N_5O_7S$ | | | | |
| C75 | 175-180 | $C_{19}H_{14}Cl_3F_3N_4O_5S$ | | | | |
| C76 | 171-173 | $C_{19}H_{15}Cl_3F_2N_4O_5S$ | | | | |
| C77 | 66-70 | $C_{19}H_{15}ClF_4N_4O_5S$ | | | | |
| C78 | 248-253 | $C_{22}H_{22}ClF_3N_4O_5S$ | | | | |
| C79 | Solid | $C_{21}H_{20}ClF_3N_4O_5S$ | | | | |
| C80 | 67-70 | $C_{20}H_{15}ClF_6N_4O_5S$ | | | | |
| C81 | 58-62 | $C_{20}H_{18}ClF_3N_4O_6S$ | | | | |
| C82 | Solid | $C_{20}H_{18}ClF_3N_4O_5S$ | | | | |
| C83 | 108-113 | $C_{20}H_{17}ClF_3N_4O_6SNa$ | | | | |
| C84 | 155-157 | $C_{20}H_{17}Cl_2F_3N_4O_5S$ | C | 43.41 | 3.10 | 10.13 |
| | | | F | 42.65 | 3.30 | 9.19 |
| C85 | 69-74 | $C_{17}H_{14}ClF_3N_4O_5S_2$ | | | | |
| C86 | Solid | $C_{19}H_{20}ClF_3N_4O_5$ | | | | |
| C87 | Solid | $C_{23}H_{24}ClF_3N_4O_5S$ | C | 49.24 | 4.31 | 9.99 |
| | | | F | 46.40 | 4.21 | 8.63 |
| C88 | Solid | $C_{19}H_{17}Cl_2FN_4O_5S$ | | | | |
| C89 | Solid | $C_{18}H_{18}ClF_3N_4O_5$ | | | | |
| C90 | 168-172 | $C_{21}H_{20}ClF_3N_4O_7S$ | | | | |
| C91 | Solid | $C_{21}H_{19}ClF_3N_4O_7SNa$ | | | | |
| C92 | Solid | $C_{20}H_{17}ClF_3N_4O_5SNa$ | | | | |
| C93 | 173-179 | $C_{21}H_{18}ClF_3N_4O_7S$ | | | | |
| C94 | 65-70 | $C_{19}H_{15}Cl_2F_3N_4O_5S$ | | | | |
| C95 | 110 | $C_{19}H_{15}BrClF_3N_4O_5S$ | C | 39.09 | 2.59 | 9.60 |
| | | | F | 38.75 | 2.66 | 9.64 |
| C97 | Solid | $C_{20}H_{22}ClF_3N_4O_5$ | | | | |
| C98 | Solid | $C_{21}H_{17}ClF_3N_4O_7SNa$ | | | | |
| C99 | Solid | $C_{20}H_{17}BrClF_3N_4O_6S$ | | | | |
| C100 | Solid | $C_{20}H_{16}BrClF_3N_4O_6SNa$ | | | | |

TABLE 6-continued

| Cmpd. No. | Melting Point (°C.) | Identifying Properties Empirical Formula | | Elemental Analysis C | H | N |
|---|---|---|---|---|---|---|
| C101 | Solid | $C_{20}H_{15}ClF_3N_5O_5S$ | C | 45.33 | 2.85 | 13.22 |
| | | | F | 44.83 | 2.42 | 13.06 |
| C102 | 60–70 | $C_{18}H_{18}ClF_3N_4O_5S$ | C | 43.69 | 3.67 | 11.32 |
| | | | F | 43.24 | 4.01 | 10.71 |
| C103 | 80–95 | $C_{18}H_{18}ClF_3N_4O_7S$ | | | | |
| C104 | Oil | $C_{21}H_{24}ClF_3N_4O_5$ | | | | |
| C105 | Solid | $C_{21}H_{20}ClF_3N_4O_7S$ | | | | |
| C106 | Solid | $C_{21}H_{19}ClF_3N_4O_7SNa$ | | | | |
| C107 | 170 | $C_{19}H_{15}ClF_3N_5O_7S$ | | | | |
| C108 | Solid | $C_{18}H_{19}ClF_3N_5O_4$ | | | | |
| C109 | Oil | $C_{22}H_{22}ClF_3N_4O_6S$ | | | | |
| C110 | 85–90 | $C_{22}H_{21}ClF_3N_4O_6SNa$ | | | | |
| C111 | Oil | $C_{19}H_{16}ClF_3N_4O_6S$ | | | | |
| C112 | 174–176 | $C_{20}H_{18}ClF_3N_4O_7S$ | | | | |
| C113 | Oil | $C_{20}H_{17}Cl_2F_3N_4O_5S$ | | | | |
| C114 | 60–70 | $C_{20}H_{16}Cl_2F_3N_4O_5SNa$ | | | | |
| C115 | Solid | $C_{19}H_{15}BrClF_3N_4O_5S$ | | | | |
| C116 | 188–191 | $C_{20}H_{16}ClF_3N_4O_7S$ | | | | |
| C117 | >230 | $C_{23}H_{18}ClF_3N_4O_5S$ | | | | |
| C118 | 144–147 | $C_{21}H_{19}Cl_3F_2N_4O_7S$ | | | | |
| C119 | 211–212 | $C_{20}H_{18}ClF_3N_4O_7S$ | | | | |
| C120 | Solid | $C_{20}H_{17}ClF_3N_4O_7SNa$ | | | | |
| C121 | Solid | $C_{20}H_{17}ClF_3N_4O_7SNa$ | | | | |
| C122 | 105–110 | $C_{21}H_{20}Cl_2F_2N_4O_7S$ | | | | |
| C123 | 163–166 | $C_{21}H_{20}BrF_3N_4SO_7$ | | | | |
| C124 | Solid | $C_{21}H_{21}ClF_3N_5O_5S$ | | | | |
| C125 | Solid | $C_{20}H_{15}ClF_6N_4O_6S$ | | | | |
| C126 | Solid | $C_{20}H_{17}ClF_3N_5O_7S$ | | | | |
| C127 | Solid | $C_{28}H_{34}ClF_3N_4F_3O_5S$ | | | | |
| C128 | Solid | $C_{28}H_{33}ClF_3N_4O_5SNa$ | | | | |
| C129 | 147–149 | $C_{19}H_{16}ClF_3N_4O_6S$ | C | 43.81 | 3.10 | 10.76 |
| | | | F | 44.31 | 3.26 | 10.54 |
| C130 | Solid | $C_{19}H_{15}ClF_3N_4O_6SNa$ | | | | |
| C131 | 198–201 | $C_{23}H_{22}ClF_3N_4O_6S$ | C | 48.05 | 3.86 | 9.74 |
| | | | F | 47.11 | 3.89 | 9.34 |
| C132 | Solid | $C_{20}H_{14}ClF_6N_4O_6SNa$ | | | | |
| C133 | Solid | $C_{20}H_{15}BrF_6N_4O_6S$ | | | | |
| C134 | 65–68 | $C_{20}H_{17}ClF_4N_4O_6S$ | | | | |
| C135 | 68–72 | $C_{20}H_{17}ClF_4N_4O_6S$ | | | | |
| C136 | Solid | $C_{21}H_{20}ClF_3N_4O_6S$ | | | | |
| C137 | 130–134 | $C_{20}H_{17}ClF_4N_4O_3$ | | | | |
| C138 | 136–140 | $C_{23}H_{18}ClF_3N_4O_5S$ | | | | |
| C139 | Solid | $C_{21}H_{19}ClF_3N_4O_6SNa$ | | | | |

TABLE 7

Preemergence Herbicidal Activity

| Compound No. | 1 | | 2 | | 3 | | 4 | | 6 | | 7 | | 8 | | 9 | | 10 | | 11 | | 12 | | 13 | | 14 | |
|---|---|---|---|---|---|---|---|---|---|---|---|---|---|---|---|---|---|---|---|---|---|---|---|---|---|---|
| Rate (kg/ha) | 2.0 | | 4.0 | | 2.0 | | 2.0 | | 2.0 | | 2.0 | | 2.0 | | 2.0 | | 2.0 | | 2.0 | | 2.0 | | 2.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 100 | 100 | | | 100 | 50 | | | 100 | | 60 | | 70 | | 100 | | 100 | | 40 | | 100 | | 30 | | 90 |
| Soybean | | 0 | 90 | | | 30 | 0 | | | 10 | | 30 | | 20 | | 20 | | 20 | | 100 | | 30 | | 20 | | 0 |
| Field Corn | | 80 | 100 | | | 100 | 30 | | | 70 | | 30 | | 20 | | 80 | | 100 | | 40 | | 20 | | 20 | | 60 |
| Rice | | 50 | 100 | | | 90 | 30 | | | 80 | | 50 | | 60 | | 90 | | 90 | | 90 | | 70 | | 10 | | 30 |
| Wheat | | 0 | 100 | | | 100 | 30 | | | 100 | | 80 | | 40 | | 90 | | 90 | | 70 | | 50 | | 10 | | 20 |
| Field Bindweed | | 100 | 100 | | | 100 | 100 | | | 100 | | 60 | | 80 | | 100 | | 100 | | 100 | | 90 | | 20 | | 100 |
| Morningglory | | 100 | 100 | | | 60 | 0 | | | 100 | | 70 | | 90 | | 100 | | 100 | | 100 | | 100 | | 50 | | 90 |
| Velvetleaf | | 100 | 100 | | | ND | 100 | | | 100 | | 100 | | 100 | | 100 | | 100 | | 100 | | 100 | | 80 | | 100 |
| Barnyardgrass | | 90 | 100 | | | 100 | 100 | | | 100 | | 100 | | 100 | | 100 | | 100 | | 100 | | 100 | | 40 | | 50 |
| Green Foxtail | | 100 | 100 | | | 100 | ND | | | 100 | | 100 | | 100 | | 100 | | 100 | | 100 | | 100 | | 40 | | 10 |
| Johnsongrass | | 80 | 100 | | | 100 | 95 | | | 90 | | 90 | | 90 | | 100 | | 100 | | 100 | | 90 | | 40 | | 60 |
| Yellow Nutsedge | | 70 | 100 | | | 100 | 0 | | | 100 | | 50 | | 80 | | 100 | | 100 | | 90 | | 90 | | 10 | | 100 |

| Compound No. | 15 | | 16 | | 17 | | 18 | | 19 | | 20 | | 21 | | 51 | | 52 | | A1 | | A2 | | A3 | | A4 | |
|---|---|---|---|---|---|---|---|---|---|---|---|---|---|---|---|---|---|---|---|---|---|---|---|---|---|---|
| Rate (kg/ha) | 1.0 | | 1.0 | | 2.0 | | 0.5 | | 2.0 | | 0.5 | | 2.0 | | 2.0 | | 2.0 | | 4.0 | | 2.0 | | 2.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 100 | | 100 | | 100 | | 10 | | 80 | | 30 | | 80 | | 70 | | 100 | 100 | | | 10 | 80 | | | 90 |
| Soybean | | 40 | | 30 | | 0 | | 20 | | 100 | | 0 | | 20 | | 10 | | 70 | 0 | | | 0 | 20 | | | 10 |
| Field Corn | | 40 | | 100 | | 30 | | 10 | | 80 | | 0 | | 80 | | 30 | | 100 | 0 | | | 0 | 0 | | | 40 |
| Rice | | 80 | | 90 | | 30 | | 0 | | 90 | | 20 | | 30 | | 40 | | 95 | 80 | | | 10 | 70 | | | 80 |
| Wheat | | 100 | | 100 | | 10 | | 0 | | 50 | | 0 | | 0 | | 0 | | 100 | 80 | | | 20 | 100 | | | 80 |
| Field Bindweed | | 90 | | 100 | | 90 | | 0 | | 100 | | 90 | | 100 | | 90 | | 100 | 100 | | | 30 | 50 | | | 70 |
| Morningglory | | 100 | | 90 | | 90 | | 0 | | 90 | | 90 | | 90 | | 80 | | 95 | 100 | | | 10 | 0 | | | 90 |
| Velvetleaf | | 100 | | 100 | | 90 | | 30 | | 100 | | 100 | | 100 | | 100 | | 100 | 100 | | | ND | 100 | | | 100 |
| Barnyardgrass | | 100 | | 100 | | 90 | | 0 | | 100 | | 50 | | 100 | | 30 | | 100 | 100 | | | 40 | 100 | | | 100 |
| Green Foxtail | | 100 | | 100 | | 10 | | 90 | | 100 | | 100 | | 100 | | 20 | | 100 | 100 | | | 100 | ND | | | 100 |
| Johnsongrass | | 90 | | 90 | | 80 | | 0 | | 90 | | 30 | | 90 | | 80 | | 100 | 80 | | | 30 | 95 | | | 90 |
| Yellow Nutsedge | | 90 | | 100 | | 60 | | 0 | | 100 | | 10 | | 70 | | 40 | | 100 | 90 | | | 20 | 0 | | | 90 |

| Compound No. | A6 | | B1 | | B2 | | B3 | | B4 | | B5 | | B6 | | B7 | | B8 | | B9 | | B10 | | B11 | | B12 | |
|---|---|---|---|---|---|---|---|---|---|---|---|---|---|---|---|---|---|---|---|---|---|---|---|---|---|---|
| Rate (kg/ha) | 0.5 | | 2.0 | | 2.0 | | 2.0 | | 1.0 | | 2.0 | | 1.0 | | 1.0 | | 2.0 | | 0.5 | | 1.0 | | 1.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 80 | | 100 | | 100 | | 100 | | 90 | | 100 | | 100 | | 100 | | 100 | | 100 | | 20 | | 100 | | 100 |
| Soybean | | 30 | | 10 | | 10 | | 0 | | 40 | | 20 | | 10 | | 30 | | 50 | | 20 | | 0 | | 10 | | 10 |
| Field Corn | | 30 | | 30 | | 90 | | 30 | | 80 | | 50 | | 40 | | 80 | | 100 | | 30 | | 30 | | 60 | | 20 |
| Rice | | 30 | | 90 | | 90 | | 70 | | 80 | | 90 | | 90 | | 90 | | 90 | | 60 | | 30 | | 60 | | 60 |
| Wheat | | 30 | | 70 | | 90 | | 80 | | 90 | | 90 | | 90 | | 80 | | 90 | | 40 | | 70 | | 90 | | 50 |
| Field Bindweed | | 70 | | 100 | | 100 | | 90 | | 100 | | 100 | | 90 | | 100 | | 100 | | 80 | | 100 | | 100 | | 70 |
| Morningglory | | 90 | | 100 | | 100 | | 100 | | 90 | | 90 | | 100 | | 100 | | 100 | | 60 | | 90 | | 90 | | 90 |
| Velvetleaf | | 90 | | 100 | | 100 | | 100 | | 100 | | 100 | | 100 | | 100 | | 100 | | 100 | | 100 | | 100 | | 100 |
| Barnyardgrass | | 100 | | 100 | | 100 | | 100 | | 100 | | 100 | | 100 | | 100 | | 100 | | 100 | | 100 | | 100 | | 100 |
| Green Foxtail | | 100 | | 100 | | 100 | | 100 | | 100 | | 100 | | 100 | | 100 | | 100 | | 100 | | 100 | | 100 | | 100 |
| Johnsongrass | | 80 | | 90 | | 100 | | 100 | | 90 | | 100 | | 90 | | 80 | | 100 | | 50 | | 80 | | 90 | | 80 |
| Yellow Nutsedge | | 80 | | 100 | | 100 | | 100 | | 90 | | 100 | | 100 | | 100 | | 100 | | 100 | | 70 | | 100 | | 90 |

| Compound No. | B13 | B14 | B15 | B16 | B17 | B18 | B21 | B22 | B23 | B25 | B30 | B31 | B32 |
|---|---|---|---|---|---|---|---|---|---|---|---|---|---|
| Rate (kg/ha) | 1.0 | 1.0 | 2.0 | 1.0 | 1.0 | 2.0 | 1.0 | 0.5 | 1.0 | 1.0 | 0.5 | 1.0 | 0.5 |

TABLE 7-continued

Preemergence Herbicidal Activity

| Species | % K | % C | % K | % C | % K | % C | % K | % C | % K | % C | % K | % C | % K | % C | % K | % C | % K | % C | % K | % C | % K | % C | % K | % C | % K | % C |
|---|---|---|---|---|---|---|---|---|---|---|---|---|---|---|---|---|---|---|---|---|---|---|---|---|---|---|
| Cotton | | 90 | | 100 | | 100 | | 80 | | 100 | | 100 | | 90 | | 60 | | 70 | | 70 | | 100 | | 100 | | 20 |
| Soybean | | 100 | | 20 | | 70 | | 20 | | 40 | | 30 | | 0 | | 0 | | 0 | | 50 | | 0 | | 10 | | 0 |
| Field Corn | | 90 | | 40 | | 90 | | 60 | | 80 | | 60 | | 50 | | 0 | | 30 | | 70 | | 10 | | 20 | | 20 |
| Rice | | 90 | | 80 | | 90 | | 60 | | 80 | | 80 | | 40 | | 40 | | 80 | | 60 | | 20 | | 50 | | 20 |
| Wheat | | 90 | | 90 | | 90 | | 50 | | 90 | | 90 | | 50 | | 10 | | 60 | | 50 | | 20 | | 30 | | 10 |
| Field Bindweed | | 100 | | 90 | | 100 | | 90 | | 80 | | 100 | | 90 | | 20 | | 90 | | 70 | | 20 | | 70 | | 30 |
| Morningglory | | 100 | | 100 | | 100 | | 100 | | 100 | | 100 | | 90 | | 40 | | 100 | | 100 | | 50 | | 80 | | 30 |
| Velvetleaf | | 100 | | 100 | | 100 | | 100 | | 100 | | 100 | | 100 | | 100 | | 100 | | 100 | | 100 | | 100 | | 90 |
| Barnyardgrass | | 100 | | 100 | | 100 | | 100 | | 100 | | 100 | | 100 | | 80 | | 90 | | 100 | | 100 | | 100 | | 100 |
| Green Foxtail | | 100 | | 100 | | 100 | | 100 | | 90 | | 100 | | 90 | | 80 | | 100 | | 100 | | 100 | | 100 | | 100 |
| Johnsongrass | | 90 | | 90 | | 100 | | 90 | | 90 | | 90 | | 40 | | 20 | | 70 | | 90 | | 50 | | 80 | | 50 |
| Yellow Nutsedge | | 90 | | 90 | | 100 | | 100 | | 100 | | 100 | | 90 | | 90 | | 80 | | 90 | | 100 | | 90 | | 90 |

| Compound No. | B33 | | B50 | | B57 | | C1 | | C2 | | C3 | | C4 | | C5 | | C6 | | C7 | | C8 | | C9 | | C10 | |
|---|---|---|---|---|---|---|---|---|---|---|---|---|---|---|---|---|---|---|---|---|---|---|---|---|---|---|
| Rate (kg/ha) | 1.0 | | 0.5 | | 0.5 | | 2.0 | | 1.0 | | 2.0 | | 2.0 | | 2.0 | | 2.0 | | 1.0 | | 2.0 | | 1.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 80 | | 50 | | 100 | | 70 | | 100 | | 100 | | 40 | | 100 | | 100 | | 100 | | 90 | | 80 | | 100 |
| Soybean | | 40 | | 20 | | 10 | | 40 | | 100 | | 40 | | 0 | | 100 | | 90 | | 10 | | 100 | | 90 | | 90 |
| Field Corn | | 90 | | 30 | | 40 | | 60 | | 100 | | 80 | | 0 | | 100 | | 100 | | 100 | | 100 | | 100 | | 20 |
| Rice | | 90 | | 40 | | 50 | | 20 | | 100 | | 80 | | 0 | | 100 | | 100 | | 40 | | 100 | | 90 | | 80 |
| Wheat | | 60 | | 60 | | 60 | | 20 | | 100 | | 90 | | 40 | | 100 | | 100 | | 30 | | 100 | | 100 | | 70 |
| Field Bindweed | | 90 | | 10 | | 90 | | 100 | | 100 | | 100 | | 80 | | 100 | | 100 | | 100 | | 100 | | 100 | | 100 |
| Morningglory | | 90 | | 50 | | 70 | | 100 | | 100 | | 100 | | 90 | | 100 | | 90 | | 100 | | 100 | | 100 | | 100 |
| Velvetleaf | | 100 | | 100 | | 100 | | 100 | | 100 | | 100 | | 100 | | 100 | | 100 | | 100 | | 100 | | 100 | | 100 |
| Barnyardgrass | | 100 | | 90 | | 100 | | 80 | | 100 | | 100 | | 90 | | 100 | | 100 | | 100 | | 100 | | 100 | | 100 |
| Green Foxtail | | 100 | | 100 | | 100 | | 90 | | 100 | | 100 | | 90 | | 100 | | 100 | | 90 | | 100 | | 100 | | 100 |
| Johnsongrass | | 70 | | 50 | | 70 | | 80 | | 100 | | 100 | | 50 | | 100 | | 100 | | 90 | | 100 | | 100 | | 90 |
| Yellow Nutsedge | | 90 | | 50 | | 90 | | 80 | | 100 | | 100 | | 50 | | 100 | | 100 | | 100 | | 90 | | 80 | | 60 |

| Compound No. | C11 | | C12 | | C13 | | C14 | | C15 | | C16 | | C17 | | C18 | | C19 | | C20 | | C21 | | C22 | | C23 | |
|---|---|---|---|---|---|---|---|---|---|---|---|---|---|---|---|---|---|---|---|---|---|---|---|---|---|---|
| Rate (kg/ha) | 1.0 | | 1.0 | | 2.0 | | 2.0 | | 2.0 | | 2.0 | | 2.0 | | 1.0 | | 1.0 | | 1.0 | | 1.0 | | 1.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 100 | | 100 | | 100 | | 100 | | 100 | | 100 | | 100 | | 100 | | 100 | | 100 | | 100 | | 100 | | 30 |
| Soybean | | 100 | | 100 | | 100 | | 100 | | 100 | | 100 | | 100 | | 0 | | 20 | | 80 | | 90 | | 100 | | 50 |
| Field Corn | | 100 | | 100 | | 90 | | 100 | | 100 | | 100 | | 100 | | 70 | | 100 | | 50 | | 100 | | 100 | | 90 |
| Rice | | 100 | | 100 | | 100 | | 100 | | 100 | | 100 | | 90 | | 80 | | 60 | | 30 | | 80 | | 100 | | 20 |
| Wheat | | 100 | | 100 | | 90 | | 100 | | 100 | | 100 | | 90 | | 50 | | 40 | | 10 | | 100 | | 100 | | 70 |
| Field Bindweed | | 100 | | 100 | | 100 | | 100 | | 100 | | 100 | | 100 | | 80 | | 80 | | 100 | | 100 | | 100 | | 100 |
| Morningglory | | 100 | | 100 | | 100 | | 100 | | 100 | | 100 | | 100 | | 100 | | 100 | | 100 | | 100 | | 100 | | 100 |
| Velvetleaf | | 100 | | 100 | | 100 | | 100 | | 100 | | 100 | | 100 | | 100 | | 100 | | 100 | | 100 | | 100 | | 100 |
| Barnyardgrass | | 100 | | 100 | | 100 | | 100 | | 100 | | 100 | | 100 | | 100 | | 100 | | 100 | | 100 | | 100 | | 100 |
| Green Foxtail | | 100 | | 100 | | 100 | | 100 | | 100 | | 100 | | 100 | | 100 | | 100 | | 100 | | 100 | | 100 | | 100 |
| Johnsongrass | | 100 | | 100 | | 100 | | 100 | | 100 | | 100 | | 100 | | 90 | | 90 | | 40 | | 100 | | 100 | | 100 |
| Yellow Nutsedge | | 100 | | 100 | | 100 | | 100 | | 100 | | 100 | | 100 | | 90 | | 80 | | 10 | | 80 | | 100 | | 40 |

| Compound No. | C24 | | C25 | | C26 | | C32 | | C38 | | C42 | | C43 | | C59 | | C69 | | C70 | | C71 | | C72 | | C73 | |
|---|---|---|---|---|---|---|---|---|---|---|---|---|---|---|---|---|---|---|---|---|---|---|---|---|---|---|
| Rate (kg/ha) | 1.0 | | 2.0 | | 1.0 | | 1.0 | | 1.0 | | 1.0 | | 1.0 | | 1.0 | | 0.5 | | 1.0 | | 1.0 | | 1.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 40 | | 100 | | 100 | | 100 | | 90 | | 90 | | 100 | | 100 | | 40 | | 100 | | 100 | | 100 | | 80 |
| Soybean | | 10 | | 30 | | 100 | | 40 | | 100 | | 70 | | 70 | | 50 | | 10 | | 20 | | 50 | | 50 | | 30 |

TABLE 7-continued

Preemergence Herbicidal Activity

| | | | | | | | | | | | | | |
|---|---|---|---|---|---|---|---|---|---|---|---|---|---|
| Field Corn | 80 | 70 | 100 | 20 | 100 | 40 | 70 | 70 | 30 | 30 | 50 | 60 | 30 |
| Rice | 30 | 60 | 90 | 50 | 100 | 60 | 90 | 80 | 30 | 70 | 40 | 30 | 40 |
| Wheat | 0 | 30 | 100 | 10 | 100 | 70 | 70 | 40 | 0 | 20 | 40 | 20 | 50 |
| Field Bindweed | 90 | 100 | 100 | 100 | 100 | 100 | 100 | 100 | 90 | 100 | 100 | 100 | 100 |
| Morningglory | 100 | 100 | 100 | 100 | 100 | 100 | 100 | 100 | 80 | 100 | 100 | 100 | 100 |
| Velvetleaf | 90 | 100 | 100 | 100 | 100 | 100 | 100 | 100 | 100 | 100 | 100 | 100 | 100 |
| Barnyardgrass | 80 | 100 | 100 | 100 | 100 | 100 | 100 | 100 | 20 | 20 | 90 | 100 | 90 |
| Green Foxtail | 100 | 90 | 100 | 80 | 100 | 100 | 100 | 100 | 20 | 0 | 40 | 95 | 100 |
| Johnsongrass | 70 | 70 | 100 | 80 | 100 | 60 | 95 | 100 | 40 | 80 | 60 | 90 | 80 |
| Yellow Nutsedge | 30 | 80 | 100 | 40 | ND | 70 | 100 | 70 | 70 | 90 | 40 | 60 | 20 |

| Compound No. | C74 | | C75 | | C76 | | C77 | | C78 | | C79 | | C80 | | C81 | | C82 | | C83 | | C84 | | C85 | | C86 | |
|---|---|---|---|---|---|---|---|---|---|---|---|---|---|---|---|---|---|---|---|---|---|---|---|---|---|---|
| Rate (kg/ha) | 1.0 | | 1.0 | | 1.0 | | 1.0 | | 1.0 | | 1.0 | | 1.0 | | 1.0 | | 1.0 | | 1.0 | | 1.0 | | 1.0 | | 2.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 100 | | 90 | | 60 | | 95 | | 80 | | 50 | | 60 | | 100 | | 100 | | 95 | | 10 | | 100 | | 100 |
| Soybean | | 80 | | 30 | | 30 | | 40 | | 40 | | 0 | | 20 | | 100 | | 10 | | 95 | | 0 | | 30 | | 70 |
| Field Corn | | 0 | | 50 | | 20 | | 30 | | 30 | | 10 | | 0 | | 50 | | 20 | | 20 | | 10 | | 95 | | 100 |
| Rice | | 40 | | 60 | | 30 | | 70 | | 50 | | 50 | | 20 | | 50 | | 30 | | 40 | | 20 | | 80 | | 90 |
| Wheat | | 30 | | 40 | | 20 | | 60 | | 40 | | 20 | | 30 | | 100 | | 20 | | 30 | | 0 | | 80 | | 90 |
| Field Bindweed | | 90 | | 100 | | 100 | | 100 | | 100 | | 80 | | 100 | | 100 | | 100 | | 100 | | 30 | | 100 | | 100 |
| Morningglory | | 100 | | 100 | | 100 | | 100 | | 100 | | 100 | | 100 | | 100 | | 100 | | 100 | | 100 | | 100 | | 100 |
| Velvetleaf | | 100 | | 100 | | 100 | | 100 | | 100 | | 100 | | 100 | | 100 | | 100 | | 100 | | 90 | | 100 | | 100 |
| Barnyardgrass | | 85 | | 95 | | 100 | | 100 | | 100 | | 80 | | 95 | | 100 | | 95 | | 95 | | 10 | | 100 | | 100 |
| Green Foxtail | | 100 | | 95 | | 70 | | 100 | | 90 | | 100 | | 100 | | 100 | | 100 | | 90 | | 30 | | 100 | | 100 |
| Johnsongrass | | 70 | | 80 | | 40 | | 95 | | 40 | | 80 | | 95 | | 100 | | 95 | | 80 | | 30 | | 100 | | 100 |
| Yellow Nutsedge | | 20 | | 30 | | 30 | | 30 | | 30 | | 20 | | 0 | | 80 | | 10 | | 20 | | ND | | ND | | ND |

| Compound No. | C87 | | C88 | | C89 | | C90 | | C91 | | C92 | | C93 | | C94 | | C95 | | C97 | | C98 | | C99 | | C100 | |
|---|---|---|---|---|---|---|---|---|---|---|---|---|---|---|---|---|---|---|---|---|---|---|---|---|---|---|
| Rate (kg/ha) | 1.0 | | 1.0 | | 1.0 | | 1.0 | | 1.0 | | 1.0 | | 1.0 | | 1.0 | | 1.0 | | 1.0 | | 0.5 | | 0.5 | | 0.5 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 30 | | 0 | | 90 | | 100 | | 100 | | 100 | | 20 | | 80 | | 100 | | 100 | | 100 | | 80 | | 80 |
| Soybean | | 20 | | 10 | | 30 | | 100 | | 90 | | 30 | | 0 | | 20 | | 60 | | 20 | | 30 | | 70 | | 50 |
| Field Corn | | 10 | | 10 | | 60 | | 80 | | 80 | | 20 | | 30 | | 20 | | 20 | | 70 | | 40 | | 30 | | 60 |
| Rice | | 40 | | 0 | | 90 | | 80 | | 90 | | 40 | | 50 | | 20 | | 30 | | 80 | | 20 | | 20 | | 60 |
| Wheat | | 10 | | 0 | | 80 | | 70 | | 50 | | 30 | | 10 | | 0 | | 10 | | 70 | | 20 | | 10 | | 20 |
| Field Bindweed | | 100 | | 0 | | 100 | | 100 | | 100 | | 100 | | 80 | | 100 | | 100 | | 100 | | 100 | | 100 | | 100 |
| Morningglory | | 100 | | 0 | | 100 | | 100 | | 100 | | 100 | | 80 | | 100 | | 100 | | 100 | | 100 | | 100 | | 100 |
| Velvetleaf | | 100 | | 10 | | 100 | | 100 | | 100 | | 100 | | 100 | | 100 | | 100 | | 100 | | 100 | | 100 | | 100 |
| Barnyardgrass | | 95 | | 40 | | 100 | | 100 | | 100 | | 100 | | 100 | | 60 | | 40 | | 100 | | 90 | | 10 | | 70 |
| Green Foxtail | | 0 | | 0 | | 100 | | 100 | | 100 | | 100 | | 0 | | 50 | | 50 | | 100 | | 80 | | 100 | | 80 |
| Johnsongrass | | 30 | | 10 | | 95 | | 100 | | 95 | | 80 | | 30 | | 60 | | 60 | | 90 | | 95 | | 80 | | 80 |
| Yellow Nutsedge | | ND | | ND | | ND | | ND | | ND | | ND | | ND | | ND | | ND | | ND | | ND | | ND | | ND |

| Compound No. | C101 | | C102 | | C103 | | C104 | | C105 | | C106 | | C107 | | C108 | | C109 | | C110 | | C111 | | C112 | | C113 | |
|---|---|---|---|---|---|---|---|---|---|---|---|---|---|---|---|---|---|---|---|---|---|---|---|---|---|---|
| Rate (kg/ha) | 0.5 | | 0.5 | | 0.5 | | 0.5 | | 0.5 | | 0.5 | | 0.5 | | 0.5 | | 0.5 | | 0.5 | | 0.5 | | 0.5 | | 0.5 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 95 | | 30 | | 30 | | 30 | | 100 | | 100 | | 90 | | 100 | | 70 | | 30 | | 20 | | 90 | | 50 |
| Soybean | | 30 | | 20 | | 10 | | 10 | | 95 | | 90 | | 10 | | 95 | | 90 | | 95 | | 40 | | 40 | | 0 |
| Field Corn | | 10 | | 50 | | 30 | | 90 | | 70 | | 30 | | 20 | | 100 | | 100 | | 100 | | 10 | | 0 | | 10 |
| Rice | | 20 | | 80 | | 50 | | 80 | | 95 | | 90 | | 40 | | 95 | | 95 | | 90 | | 70 | | 20 | | 20 |
| Wheat | | 10 | | 50 | | 30 | | 80 | | 50 | | 30 | | 0 | | 95 | | 100 | | 100 | | 50 | | 10 | | 10 |

TABLE 7-continued

Preemergence Herbicidal Activity

| | | | | | | | | | | | | | |
|---|---|---|---|---|---|---|---|---|---|---|---|---|---|
| Field Bindweed | 90 | 20 | 40 | 100 | 100 | 100 | 80 | 90 | 95 | 100 | 70 | 100 | 100 |
| Morningglory | 100 | 80 | 60 | 90 | 100 | 100 | 95 | 100 | 100 | 100 | 70 | 90 | 90 |
| Velvetleaf | 100 | 100 | 100 | 100 | 100 | 100 | 100 | 100 | 100 | 100 | 90 | 100 | 100 |
| Barnyardgrass | 60 | 100 | 95 | 95 | 100 | 100 | 40 | 80 | 100 | 100 | 100 | 40 | 50 |
| Green Foxtail | 40 | 100 | 100 | 100 | 100 | 100 | 0 | 100 | 100 | 100 | 100 | 80 | 30 |
| Johnsongrass | 50 | 80 | 80 | 95 | 100 | 100 | 50 | 100 | 100 | 100 | 70 | 95 | 30 |
| Yellow Nutsedge | ND | ND | ND | ND | ND | ND | ND | ND | ND | ND | ND | ND | ND |

| Compound No. | C114 | | C115 | | C116 | | C117 | | C118 | | C119 | | C120 | | C121 | | C122 | | C123 | | C124 | | C125 | |
|---|---|---|---|---|---|---|---|---|---|---|---|---|---|---|---|---|---|---|---|---|---|---|---|---|
| Rate (kg/ha) | 0.5 | | 0.5 | | 0.5 | | 0.5 | | 0.5 | | 0.5 | | 0.5 | | 0.5 | | 0.5 | | 0.25 | | 0.5 | | 0.5 | |
| Species | % K | % C | % K | % C | % K | % C | % K | % C | % K | % C | % K | % C | % K | % C | % K | % C | % K | % C | % K | % C | % K | % C | % K | % C |
| Cotton | | 30 | | 80 | | 95 | | 50 | | 20 | | 50 | | 70 | | 95 | | 70 | | 50 | | 20 | | 20 |
| Soybean | | 0 | | 30 | | 0 | | 95 | | 0 | | 30 | | 20 | | 20 | | 50 | | 50 | | 60 | | 30 |
| Field Corn | | 10 | | 10 | | 10 | | 10 | | 10 | | 10 | | 10 | | 20 | | 40 | | 0 | | 70 | | 10 |
| Rice | | 20 | | 10 | | 20 | | 30 | | 0 | | 30 | | 20 | | 30 | | 0 | | 60 | | 80 | | 10 |
| Wheat | | 10 | | 30 | | 10 | | 0 | | 10 | | 30 | | 10 | | 10 | | 10 | | 10 | | 60 | | 10 |
| Field Bindweed | | 90 | | 100 | | 90 | | 100 | | 80 | | 100 | | 100 | | 100 | | 100 | | 100 | | 100 | | 80 |
| Morningglory | | 95 | | 100 | | 95 | | 100 | | 50 | | 100 | | 90 | | 90 | | 80 | | 100 | | 95 | | 90 |
| Velvetleaf | | 100 | | 100 | | 100 | | 100 | | 50 | | 100 | | 100 | | 100 | | 100 | | 100 | | 100 | | 100 |
| Barnyardgrass | | 70 | | 50 | | 80 | | 40 | | 10 | | 50 | | 80 | | 70 | | 70 | | 100 | | 100 | | 30 |
| Green Foxtail | | 70 | | 90 | | 40 | | 80 | | 10 | | 0 | | 0 | | 20 | | 50 | | 10 | | 100 | | 50 |
| Johnsongrass | | 70 | | 90 | | 80 | | 20 | | 10 | | 70 | | 70 | | 90 | | 100 | | 100 | | 100 | | 10 |
| Yellow Nutsedge | | ND | | ND | | ND | | ND | | ND | | ND | | ND | | ND | | ND | | ND | | ND | | ND |

TABLE 8

Postemergence Herbicidal Activity

| Compound No. | 1 | | 2 | | 3 | | 4 | | 6 | | 7 | | 8 | | 9 | | 10 | | 11 | | 12 | | 13 | | 14 | |
|---|---|---|---|---|---|---|---|---|---|---|---|---|---|---|---|---|---|---|---|---|---|---|---|---|---|---|
| Rate (kg/ha) | 2.0 | | 4.0 | | 2.0 | | 2.0 | | 2.0 | | 2.0 | | 2.0 | | 2.0 | | 2.0 | | 2.0 | | 2.0 | | 2.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 100 | 100 | | | 100 | 90 | | | 100 | | 90 | | 100 | | 100 | | 100 | | 100 | | 100 | | 70 | | 100 |
| Soybean | | 40 | 0 | | | 60 | 0 | | | 50 | | 40 | | 50 | | 30 | | 30 | | 50 | | 30 | | 20 | | 60 |
| Field Corn | | 90 | 100 | | | 100 | 0 | | | 100 | | 40 | | 30 | | 100 | | 100 | | 60 | | 30 | | 10 | | 10 |
| Rice | | 80 | 100 | | | 100 | 80 | | | 100 | | 80 | | 90 | | 70 | | 90 | | 90 | | 50 | | 30 | | 30 |
| Wheat | | 10 | 100 | | | 90 | 90 | | | 100 | | 90 | | 30 | | 80 | | 100 | | 90 | | 70 | | 20 | | 10 |
| Field Bindweed | | 100 | 100 | | | 100 | 100 | | | 100 | | 100 | | 100 | | 100 | | 100 | | 100 | | 100 | | 50 | | 100 |
| Morningglory | | 100 | 100 | | | 100 | 70 | | | 100 | | 80 | | 100 | | 80 | | 30 | | 100 | | 100 | | 80 | | 100 |
| Velvetleaf | | 100 | 100 | | | ND | 100 | | | 100 | | 100 | | 100 | | 100 | | 100 | | 100 | | 100 | | 80 | | 100 |
| Barnyardgrass | | 100 | 100 | | | 100 | 90 | | | 100 | | 100 | | 100 | | 100 | | 90 | | 100 | | 100 | | 80 | | 100 |
| Green Foxtail | | 100 | 100 | | | ND | ND | | | 100 | | 100 | | 100 | | 100 | | 100 | | 100 | | 100 | | 40 | | 90 |
| Johnsongrass | | 90 | 95 | | | 100 | 70 | | | 100 | | 100 | | 70 | | 80 | | 80 | | 80 | | 90 | | 30 | | 80 |
| Yellow Nutsedge | | 50 | 50 | | | 100 | 0 | | | 100 | | 70 | | 30 | | 80 | | 90 | | 90 | | 50 | | 20 | | 30 |
| Compound No. | 15 | | 16 | | 17 | | 18 | | 19 | | 20 | | 21 | | 51 | | 52 | | A1 | | A2 | | A3 | | A4 | |
| Rate (kg/ha) | 1.0 | | 1.0 | | 2.0 | | 0.5 | | 2.0 | | 0.5 | | 2.0 | | 2.0 | | 2.0 | | 4.0 | | 2.0 | | 2.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 100 | | 100 | | 100 | | 100 | | 100 | | 90 | | 80 | | 70 | | 100 | 100 | | | 90 | 100 | | | 100 |
| Soybean | | 40 | | 30 | | 70 | | 30 | | 40 | | 40 | | 20 | | 50 | | 95 | 0 | | | 20 | 0 | | | 40 |
| Field Corn | | 30 | | 10 | | 70 | | 60 | | 50 | | 30 | | 20 | | 10 | | 100 | 0 | | | 30 | 0 | | | 40 |
| Rice | | 90 | | 30 | | 30 | | 20 | | 50 | | 20 | | 30 | | 30 | | 90 | 30 | | | 20 | 90 | | | 20 |
| Wheat | | 60 | | 40 | | 20 | | 20 | | 30 | | 30 | | 20 | | 10 | | 100 | 30 | | | 30 | 80 | | | 90 |
| Field Bindweed | | 100 | | 90 | | 90 | | 50 | | 80 | | 40 | | 90 | | 90 | | 100 | 100 | | | 80 | 100 | | | 90 |
| Morningglory | | 100 | | 100 | | 100 | | 50 | | 90 | | 80 | | 100 | | 100 | | 100 | 100 | | | 70 | 60 | | | 100 |
| Velvetleaf | | 100 | | 100 | | 100 | | 80 | | 100 | | 100 | | 100 | | 90 | | 100 | 100 | | | ND | 100 | | | 100 |
| Barnyardgrass | | 100 | | 100 | | 70 | | 10 | | 80 | | 80 | | 14 | | 70 | | 100 | 100 | | | 90 | 100 | | | 100 |
| Green Foxtail | | 100 | | 100 | | 20 | | 60 | | 80 | | 60 | | 30 | | 10 | | 100 | 100 | | | ND | ND | | | 100 |
| Johnsongrass | | 90 | | 80 | | 70 | | 30 | | 40 | | 10 | | 40 | | 40 | | 100 | 75 | | | 60 | 95 | | | 60 |
| Yellow Nutsedge | | 80 | | 90 | | 30 | | 10 | | 90 | | 10 | | 30 | | 30 | | 100 | 0 | | | 10 | 0 | | | 100 |
| Compound No. | A6 | | B1 | | B2 | | B3 | | B4 | | B5 | | B6 | | B7 | | B8 | | B10 | | B11 | | B12 | | B13 | |
| Rate (kg/ha) | 0.5 | | 2.0 | | 2.0 | | 2.0 | | 1.0 | | 2.0 | | 1.0 | | 1.0 | | 2.0 | | 1.0 | | 1.0 | | 1.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 90 | | 100 | | 100 | | 100 | | 100 | | 100 | | 100 | | 100 | | 100 | | 100 | | 100 | | 100 | | 100 |
| Soybean | | 20 | | 10 | | 30 | | 30 | | 40 | | 60 | | 60 | | 60 | | 80 | | 20 | | 30 | | 30 | | 100 |
| Field Corn | | 20 | | 40 | | 30 | | 70 | | 30 | | 20 | | 100 | | 100 | | 70 | | 0 | | 0 | | 10 | | 60 |
| Rice | | 30 | | 50 | | 80 | | 90 | | 90 | | 80 | | 100 | | 100 | | 100 | | 20 | | 30 | | 20 | | 50 |
| Wheat | | 90 | | 100 | | 100 | | 90 | | 100 | | 90 | | 100 | | 100 | | 100 | | 10 | | 100 | | 100 | | 90 |
| Field Bindweed | | 10 | | 100 | | 100 | | 100 | | 100 | | 100 | | 90 | | 100 | | 100 | | 100 | | 100 | | 100 | | 100 |
| Morningglory | | 90 | | 100 | | 40 | | 80 | | 90 | | 100 | | 100 | | 100 | | 100 | | 100 | | 100 | | 100 | | 100 |
| Velvetleaf | | 100 | | 100 | | 100 | | 100 | | 100 | | 100 | | 100 | | 100 | | 100 | | 100 | | 100 | | 100 | | 100 |
| Barnyardgrass | | 100 | | 100 | | 100 | | 100 | | 100 | | 100 | | 100 | | 100 | | 100 | | 100 | | 100 | | 100 | | 100 |
| Green Foxtail | | 90 | | 100 | | 100 | | 100 | | 100 | | 100 | | 100 | | 100 | | 100 | | 100 | | 100 | | 100 | | 100 |
| Johnsongrass | | 30 | | 80 | | 80 | | 90 | | 80 | | 90 | | 80 | | 80 | | 70 | | 90 | | 90 | | 30 | | 100 |
| Yellow Nutsedge | | 50 | | 40 | | 80 | | 30 | | 90 | | 60 | | 100 | | 80 | | 70 | | 20 | | 100 | | 90 | | 100 |
| Compound No. | B14 | | B15 | | B16 | | B17 | | B18 | | B21 | | B22 | | B23 | | B25 | | B30 | | B31 | | B32 | | B33 | |
| Rate (kg/ha) | 1.0 | | 2.0 | | 1.0 | | 1.0 | | 2.0 | | 1.0 | | 0.5 | | 1.0 | | 1.0 | | 0.5 | | 1.0 | | 0.5 | | 1.0 | |

TABLE 8-continued

Postemergence Herbicidal Activity

| Species | % K | % C | % K | % C | % K | % C | % K | % C | % K | % C | % K | % C | % K | % C | % K | % C | % K | % C | % K | % C | % K | % C | % K | % C | % K | % C |
|---|---|---|---|---|---|---|---|---|---|---|---|---|---|---|---|---|---|---|---|---|---|---|---|---|---|---|
| Cotton | | 100 | | 100 | | 100 | | 100 | | 100 | | 100 | | 80 | | 100 | | 80 | | 80 | | 100 | | 100 | | 100 |
| Soybean | | 90 | | 80 | | 40 | | 40 | | 50 | | 30 | | 30 | | 10 | | 30 | | 10 | | 20 | | 10 | | 30 |
| Field Corn | | 20 | | 60 | | 30 | | 30 | | 20 | | 30 | | 20 | | 40 | | 90 | | 10 | | 40 | | 0 | | 40 |
| Rice | | 80 | | 90 | | 50 | | 30 | | 90 | | 20 | | 70 | | 90 | | 50 | | 70 | | 40 | | 20 | | 40 |
| Wheat | | 80 | | 100 | | 100 | | 40 | | 70 | | 100 | | 90 | | 80 | | 90 | | 100 | | 80 | | 70 | | 100 |
| Field Bindweed | | 90 | | 100 | | 100 | | 100 | | 100 | | 100 | | 50 | | 100 | | 100 | | 50 | | 100 | | 80 | | 100 |
| Morningglory | | 90 | | 100 | | 80 | | 90 | | 100 | | 100 | | 100 | | 100 | | 100 | | 100 | | 90 | | 100 | | 100 |
| Velvetleaf | | 100 | | 100 | | 100 | | 100 | | 100 | | 90 | | 100 | | 100 | | 100 | | 100 | | 90 | | 100 | | 100 |
| Barnyardgrass | | 100 | | 100 | | 100 | | 70 | | 100 | | 100 | | 100 | | 60 | | 100 | | 100 | | 100 | | 100 | | 100 |
| Green Foxtail | | 100 | | 100 | | 100 | | 100 | | 100 | | 100 | | 100 | | 100 | | 100 | | 100 | | 100 | | 100 | | 100 |
| Johnsongrass | | 60 | | 100 | | 40 | | 30 | | 40 | | 10 | | 10 | | 100 | | 50 | | 10 | | 50 | | 0 | | 40 |
| Yellow Nutsedge | | 70 | | 90 | | 100 | | 60 | | 90 | | 80 | | 10 | | 90 | | 90 | | 10 | | 90 | | 0 | | 60 |

| Compound No. | B50 | | B57 | | C1 | | C2 | | C3 | | C4 | | C5 | | C6 | | C7 | | C8 | | C9 | | C10 | | C11 | |
|---|---|---|---|---|---|---|---|---|---|---|---|---|---|---|---|---|---|---|---|---|---|---|---|---|---|---|
| Rate (kg/ha) | 0.5 | | 0.5 | | 2.0 | | 1.0 | | 2.0 | | 2.0 | | 2.0 | | 2.0 | | 1.0 | | 2.0 | | 1.0 | | 1.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 100 | | 100 | | 100 | | 100 | | 100 | | 70 | | 100 | | 100 | | 100 | | 100 | | 90 | | 100 | | 100 |
| Soybean | | 30 | | 30 | | 30 | | 90 | | 40 | | 40 | | 90 | | 90 | | 60 | | 90 | | 80 | | 100 | | 90 |
| Field Corn | | 20 | | 30 | | 70 | | 100 | | 100 | | 40 | | 100 | | 100 | | 50 | | 90 | | 80 | | 60 | | 100 |
| Rice | | 40 | | 90 | | 20 | | 100 | | 70 | | 50 | | 100 | | 100 | | 80 | | 80 | | 50 | | 60 | | 100 |
| Wheat | | 40 | | 90 | | 0 | | 100 | | 40 | | 30 | | 100 | | 100 | | 10 | | 80 | | 60 | | 60 | | 100 |
| Field Bindweed | | 70 | | 80 | | 100 | | 100 | | 90 | | 100 | | 100 | | 100 | | 100 | | 100 | | 90 | | 60 | | 90 |
| Morningglory | | 100 | | 100 | | 100 | | 100 | | 100 | | 90 | | 100 | | 100 | | 100 | | 100 | | 80 | | 100 | | 100 |
| Velvetleaf | | 100 | | 100 | | 100 | | 100 | | 100 | | 100 | | 100 | | 100 | | 100 | | 100 | | 100 | | 100 | | 100 |
| Barnyardgrass | | 100 | | 100 | | 100 | | 100 | | 100 | | 90 | | 100 | | 100 | | 100 | | 60 | | 100 | | 100 | | 100 |
| Green Foxtail | | 100 | | 100 | | 100 | | 100 | | 100 | | 90 | | 100 | | 100 | | 100 | | 100 | | 100 | | 100 | | 100 |
| Johnsongrass | | 30 | | 40 | | 80 | | 100 | | 90 | | 40 | | 90 | | 100 | | 90 | | 80 | | 90 | | 80 | | 90 |
| Yellow Nutsedge | | 20 | | 60 | | 60 | | 100 | | 30 | | 20 | | 100 | | 100 | | 80 | | 60 | | 20 | | 10 | | 100 |

| Compound No. | C12 | | C13 | | C14 | | C15 | | C16 | | C17 | | C18 | | C19 | | C20 | | C21 | | C22 | | C23 | | C24 | |
|---|---|---|---|---|---|---|---|---|---|---|---|---|---|---|---|---|---|---|---|---|---|---|---|---|---|---|
| Rate (kg/ha) | 1.0 | | 2.0 | | 2.0 | | 2.0 | | 2.0 | | 2.0 | | 1.0 | | 1.0 | | 1.0 | | 1.0 | | 1.0 | | 1.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 100 | | 100 | | 100 | | 100 | | 100 | | 100 | | 100 | | 100 | | 100 | | 100 | | 100 | | 100 | | 50 |
| Soybean | | 90 | | 80 | | 100 | | 90 | | 100 | | 100 | | 40 | | 40 | | 100 | | 100 | | 100 | | 80 | | 20 |
| Field Corn | | 100 | | 100 | | 100 | | 90 | | 100 | | 100 | | 30 | | 20 | | 0 | | 100 | | 100 | | 80 | | 20 |
| Rice | | 100 | | 100 | | 70 | | 50 | | 90 | | 100 | | 10 | | 10 | | 20 | | 60 | | 80 | | 30 | | 10 |
| Wheat | | 100 | | 100 | | 100 | | 100 | | 100 | | 100 | | 100 | | 100 | | 100 | | 100 | | 100 | | 90 | | 10 |
| Field Bindweed | | 100 | | 100 | | 100 | | 100 | | 100 | | 90 | | 100 | | 100 | | 100 | | 100 | | 100 | | 100 | | 100 |
| Morningglory | | 100 | | 100 | | 100 | | 100 | | 100 | | 100 | | 100 | | 100 | | 100 | | 100 | | 100 | | 80 | | 90 |
| Velvetleaf | | 100 | | 100 | | 100 | | 100 | | 100 | | 100 | | 100 | | 100 | | 100 | | 100 | | 100 | | 100 | | 100 |
| Barnyardgrass | | 100 | | 100 | | 100 | | 100 | | 100 | | 100 | | 100 | | 100 | | 100 | | 100 | | 100 | | 100 | | 80 |
| Green Foxtail | | 100 | | 100 | | 100 | | 100 | | 100 | | 100 | | 100 | | 100 | | 100 | | 100 | | 100 | | 100 | | 100 |
| Johnsongrass | | 100 | | 100 | | 100 | | 90 | | 100 | | 50 | | 90 | | 100 | | 40 | | 100 | | 100 | | 100 | | 60 |
| Yellow Nutsedge | | 100 | | 100 | | 100 | | 90 | | 100 | | 100 | | 100 | | 60 | | 10 | | 80 | | 80 | | 40 | | 0 |

| Compound No. | C25 | | C26 | | C32 | | C38 | | C42 | | C43 | | C59 | | C69 | | C70 | | C71 | | C72 | | C73 | | C74 | |
|---|---|---|---|---|---|---|---|---|---|---|---|---|---|---|---|---|---|---|---|---|---|---|---|---|---|---|
| Rate (kg/ha) | 2.0 | | 1.0 | | 1.0 | | 1.0 | | 1.0 | | 1.0 | | 1.0 | | 0.5 | | 1.0 | | 1.0 | | 1.0 | | 1.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 100 | | 100 | | 100 | | 100 | | 100 | | 100 | | 100 | | 100 | | 90 | | 100 | | 100 | | 100 | | 85 |
| Soybean | | 70 | | 80 | | 80 | | 100 | | 100 | | 90 | | 80 | | 50 | | 60 | | 60 | | 70 | | 85 | | 90 |

TABLE 8-continued

Postemergence Herbicidal Activity

| | | | | | | | | | | | | | |
|---|---|---|---|---|---|---|---|---|---|---|---|---|---|
| Field Corn | 60 | 100 | 20 | 100 | 100 | 100 | 80 | 80 | 40 | 60 | 50 | 30 | 40 |
| Rice | 50 | 90 | 50 | 100 | 60 | 50 | 40 | 60 | 30 | 40 | 60 | 60 | 60 |
| Wheat | 60 | 90 | 50 | 100 | 90 | 95 | 80 | 90 | 40 | 95 | 30 | 80 | 50 |
| Field Bindweed | 100 | 100 | 100 | 70 | 100 | 100 | 100 | 100 | 100 | 100 | 100 | 100 | 95 |
| Morningglory | 100 | 100 | 100 | 100 | 95 | 100 | 100 | 100 | 100 | 100 | 100 | 100 | 100 |
| Velvetleaf | 100 | 100 | 100 | 100 | 100 | 100 | 100 | 100 | 100 | 100 | 100 | 100 | 100 |
| Barnyardgrass | 100 | 100 | 100 | 100 | 95 | 100 | 100 | 100 | 100 | 100 | 100 | 90 | 100 |
| Green Foxtail | 100 | 100 | 80 | 100 | 100 | 100 | 100 | 50 | 30 | 100 | 60 | 90 | 85 |
| Johnsongrass | 100 | 90 | 40 | 90 | 95 | 100 | 95 | 60 | 70 | 50 | 50 | 70 | 50 |
| Yellow Nutsedge | 70 | 90 | 20 | ND | 40 | 95 | 100 | 50 | 40 | 20 | 60 | 30 | 30 |

| Compound No. | C75 | | C76 | | C77 | | C78 | | C79 | | C80 | | C81 | | C82 | | C83 | | C84 | | C85 | | C86 | | C87 | |
|---|---|---|---|---|---|---|---|---|---|---|---|---|---|---|---|---|---|---|---|---|---|---|---|---|---|---|
| Rate (kg/ha) | 1.0 | | 1.0 | | 1.0 | | 1.0 | | 1.0 | | 1.0 | | 1.0 | | 1.0 | | 1.0 | | 1.0 | | 1.0 | | 2.0 | | 1.0 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 95 | | 95 | | 100 | | 100 | | 100 | | 100 | | 100 | | 100 | | 100 | | 80 | | 100 | | 100 | | 90 |
| Soybean | | 90 | | 80 | | 80 | | 100 | | 50 | | 80 | | 100 | | 80 | | 100 | | 40 | | 90 | | 80 | | 100 |
| Field Corn | | 100 | | 70 | | 100 | | 100 | | 20 | | 40 | | 80 | | 100 | | 95 | | 40 | | 95 | | 100 | | 100 |
| Rice | | 40 | | 40 | | 30 | | 30 | | 20 | | 10 | | 90 | | 70 | | 60 | | 20 | | 95 | | 100 | | 50 |
| Wheat | | 40 | | 30 | | 100 | | 90 | | 40 | | 40 | | 95 | | 90 | | 90 | | 30 | | 80 | | 100 | | 60 |
| Field Bindweed | | 100 | | 100 | | 100 | | 100 | | 50 | | 100 | | 100 | | 100 | | 100 | | 20 | | 95 | | 100 | | 100 |
| Morningglory | | 100 | | 95 | | 100 | | 100 | | 60 | | 100 | | 100 | | 100 | | 100 | | 90 | | 100 | | 100 | | 100 |
| Velvetleaf | | 100 | | 100 | | 100 | | 100 | | 100 | | 100 | | 100 | | 100 | | 100 | | 100 | | 100 | | 100 | | 100 |
| Barnyardgrass | | 95 | | 95 | | 95 | | 100 | | 100 | | 40 | | 100 | | 100 | | 100 | | 95 | | 100 | | 100 | | 100 |
| Green Foxtail | | 100 | | 95 | | 100 | | 90 | | 95 | | 100 | | 100 | | 100 | | 100 | | 30 | | 100 | | 100 | | 80 |
| Johnsongrass | | 80 | | 40 | | 70 | | 60 | | 80 | | 40 | | 100 | | 100 | | 95 | | 20 | | 90 | | 100 | | 30 |
| Yellow Nutsedge | | 10 | | 20 | | 30 | | 20 | | 70 | | 20 | | 20 | | 0 | | 60 | | ND | | ND | | ND | | ND |

| Compound No. | C88 | | C89 | | C90 | | C91 | | C92 | | C93 | | C94 | | C95 | | C97 | | C98 | | C99 | | C100 | | C101 | |
|---|---|---|---|---|---|---|---|---|---|---|---|---|---|---|---|---|---|---|---|---|---|---|---|---|---|---|
| Rate (kg/ha) | 1.0 | | 1.0 | | 1.0 | | 1.0 | | 1.0 | | 1.0 | | 1.0 | | 1.0 | | 1.0 | | 0.5 | | 0.5 | | 0.5 | | 0.5 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 10 | | 90 | | 100 | | 100 | | 100 | | 100 | | 100 | | 100 | | 95 | | 90 | | 90 | | 100 | | 100 |
| Soybean | | 30 | | 90 | | 100 | | 100 | | 90 | | 70 | | 80 | | 95 | | 95 | | 70 | | 100 | | 100 | | 60 |
| Field Corn | | 20 | | 100 | | 95 | | 100 | | 100 | | 70 | | 50 | | 95 | | 100 | | 70 | | 100 | | 100 | | 50 |
| Rice | | 10 | | 70 | | 60 | | 90 | | 70 | | 30 | | 30 | | 70 | | 95 | | 70 | | 40 | | 40 | | 20 |
| Wheat | | 10 | | 100 | | 100 | | 100 | | 80 | | 80 | | 40 | | 100 | | 100 | | 90 | | 100 | | 100 | | 40 |
| Field Bindweed | | 10 | | 95 | | 100 | | 100 | | 100 | | 70 | | 95 | | 100 | | 95 | | 100 | | 100 | | 100 | | 90 |
| Morningglory | | 20 | | 100 | | 100 | | 100 | | 100 | | 95 | | 100 | | 100 | | 100 | | 100 | | 100 | | 100 | | 90 |
| Velvetleaf | | 20 | | 100 | | 100 | | 100 | | 100 | | 100 | | 100 | | 100 | | 100 | | 100 | | 100 | | 100 | | 100 |
| Barnyardgrass | | 20 | | 100 | | 100 | | 100 | | 100 | | 100 | | 80 | | 90 | | 95 | | 95 | | 100 | | 100 | | 30 |
| Green Foxtail | | 50 | | 100 | | 100 | | 100 | | 80 | | 95 | | 95 | | 100 | | 100 | | 70 | | 90 | | 100 | | 10 |
| Johnsongrass | | 30 | | 80 | | 100 | | 100 | | 70 | | 30 | | 60 | | 70 | | 95 | | 90 | | 100 | | 90 | | 50 |
| Yellow Nutsedge | | ND | | ND | | ND | | ND | | ND | | ND | | ND | | ND | | ND | | ND | | ND | | ND | | ND |

| Compound No. | C102 | | C103 | | C104 | | C105 | | C106 | | C107 | | C108 | | C109 | | C110 | | C111 | | C112 | | C113 | | C114 | |
|---|---|---|---|---|---|---|---|---|---|---|---|---|---|---|---|---|---|---|---|---|---|---|---|---|---|---|
| Rate (kg/ha) | 0.5 | | 0.5 | | 0.5 | | 0.5 | | 0.5 | | 0.5 | | 0.5 | | 0.5 | | 0.5 | | 0.5 | | 0.5 | | 0.5 | | 0.5 | |
| Species | % K | % C | % K | % C | % K | % C | % K | % C | % K | % C | % K | % C | % K | % C | % K | % C | % K | % C | % K | % C | % K | % C | % K | % C | % K | % C |
| Cotton | | 100 | | 100 | | 80 | | 100 | | 100 | | 100 | | 100 | | 95 | | 80 | | 40 | | 90 | | 80 | | 95 |
| Soybean | | 50 | | 30 | | 80 | | 100 | | 100 | | 60 | | 100 | | 95 | | 100 | | 50 | | 90 | | 40 | | 50 |
| Field Corn | | 60 | | 30 | | 90 | | 95 | | 100 | | 60 | | 100 | | 80 | | 90 | | 20 | | 40 | | 30 | | 30 |
| Rice | | 70 | | 40 | | 70 | | 95 | | 95 | | 20 | | 95 | | 80 | | 80 | | 20 | | 20 | | 30 | | 80 |
| Wheat | | 95 | | 30 | | 90 | | 100 | | 100 | | 20 | | 100 | | 95 | | 95 | | 70 | | 90 | | 30 | | 30 |

TABLE 8-continued

Postemergence Herbicidal Activity

| | | | | | | | | | | | | | |
|---|---|---|---|---|---|---|---|---|---|---|---|---|---|
| Field Bindweed | 90 | 95 | 50 | 100 | 100 | 100 | 100 | 100 | 100 | 60 | 100 | 100 | 100 |
| Morningglory | 100 | 95 | 90 | 100 | 100 | 100 | 100 | 100 | 100 | 100 | 100 | 100 | 100 |
| Velvetleaf | 95 | 100 | 100 | 100 | 100 | 100 | 100 | 100 | 100 | 100 | 100 | 100 | 100 |
| Barnyardgrass | 60 | 60 | 95 | 100 | 100 | 95 | 100 | 100 | 100 | 100 | 95 | 30 | 70 |
| Green Foxtail | 100 | 100 | 95 | 100 | 100 | 90 | 100 | 100 | 100 | 100 | 100 | 80 | 90 |
| Johnsongrass | 70 | 70 | 80 | 100 | 100 | 60 | 100 | 100 | 100 | 95 | 95 | 40 | 30 |
| Yellow Nutsedge | ND | ND | ND | ND | ND | ND | ND | ND | ND | ND | ND | ND | ND |

| Compound No. | C115 | | C116 | | C117 | | C118 | | C119 | | C120 | | C121 | | C122 | | C123 | | C124 | | C125 | |
|---|---|---|---|---|---|---|---|---|---|---|---|---|---|---|---|---|---|---|---|---|---|---|
| Rate (kg/ha) | 0.5 | | 0.5 | | 0.5 | | 0.5 | | 0.5 | | 0.5 | | 0.5 | | 0.5 | | 0.25 | | 0.5 | | 0.5 | |
| Species | % K | % C | % K | % C | % K | % C | % K | % C | % K | % C | % K | % C | % K | % C | % K | % C | % K | % C | % K | % C | % K | % C |
| Cotton | | 20 | | 100 | | 100 | | 40 | | 95 | | 80 | | 100 | | 95 | | 100 | | 100 | | 100 |
| Soybean | | 30 | | 60 | | 100 | | 95 | | 95 | | 95 | | 80 | | 80 | | 100 | | 100 | | 100 |
| Field Corn | | 30 | | 40 | | 100 | | 100 | | 40 | | 60 | | 10 | | 60 | | 90 | | 100 | | 100 |
| Rice | | 10 | | 20 | | 0 | | 10 | | 10 | | 10 | | 20 | | 10 | | 90 | | 70 | | 0 |
| Wheat | | 30 | | 60 | | 95 | | 60 | | 90 | | 100 | | 100 | | 100 | | 100 | | 100 | | 100 |
| Field Bindweed | | 10 | | 80 | | 100 | | 95 | | 100 | | 100 | | 100 | | 95 | | 100 | | 100 | | 100 |
| Morningglory | | 30 | | 100 | | 100 | | 80 | | 100 | | 100 | | 100 | | 100 | | 100 | | 100 | | 100 |
| Velvetleaf | | 20 | | 100 | | 100 | | 100 | | 100 | | 100 | | 100 | | 100 | | 100 | | 100 | | 100 |
| Barnyardgrass | | 20 | | 70 | | 100 | | 60 | | 50 | | 50 | | 80 | | 100 | | 95 | | 100 | | 95 |
| Green Foxtail | | 30 | | 70 | | 100 | | 40 | | 70 | | 20 | | 30 | | 80 | | 95 | | 100 | | 95 |
| Johnsongrass | | 30 | | 80 | | 70 | | 20 | | 60 | | 40 | | 80 | | 80 | | 95 | | 95 | | 90 |
| Yellow Nutsedge | | ND | | ND | | ND | | ND | | ND | | ND | | ND | | ND | | ND | | ND | | ND |

I claim:

1. An herbicidal compound of the formula:

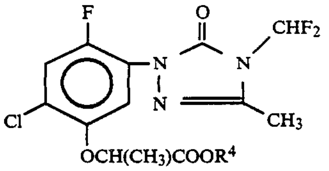

wherein $R^4$ is ethyl.

2. An herbicidal composition comprising an herbicidally effective amount of the compound of claim 1 in admixture with a suitable carrier.

3. A method for controlling undesired plant growth which comprises applying to the locus where control is desired an herbicidally effective amount of the composition of claim 2.

* * * * *